US009582645B2

(12) United States Patent
Yu et al.

(10) Patent No.: US 9,582,645 B2
(45) Date of Patent: Feb. 28, 2017

(54) NETWORKED DIALYSIS SYSTEM

(71) Applicants: Baxter International Inc., Deerfield, IL (US); Baxter Healthcare S.A., Glattpark (Opfikon) (CH)

(72) Inventors: Anping Yu, Safety Harbor, FL (US); Robert W. Childers, New Port Richey, FL (US); Borut Cizman, Highwood, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 650 days.

(21) Appl. No.: 14/012,093

(22) Filed: Aug. 28, 2013

(65) Prior Publication Data
US 2013/0346099 A1 Dec. 26, 2013

Related U.S. Application Data

(63) Continuation of application No. 13/947,771, filed on Jul. 22, 2013, now Pat. No. 9,141,760, which is a
(Continued)

(51) Int. Cl.
*A61M 1/16* (2006.01)
*A61M 1/28* (2006.01)
(Continued)

(52) U.S. Cl.
CPC ....... *G06F 19/3418* (2013.01); *A61M 1/1601* (2014.02); *A61M 1/28* (2013.01);
(Continued)

(58) Field of Classification Search
CPC ........ A61M 1/28; A61M 1/281; A61M 1/282; A61M 1/1601; A61M 1/1603;
(Continued)

(56) References Cited

U.S. PATENT DOCUMENTS 3,268,441 A    8/1966   Lindstrom
3,327,115 A    6/1967   Bartlett
(Continued)

FOREIGN PATENT DOCUMENTS

DE    1226740    10/1966
DE    1964735    7/1971
(Continued)

OTHER PUBLICATIONS

Notification of Transmittal of International Preliminary Report on Patentability for International Application No. PCT/US2009/050073 dated Oct. 12, 2010.
(Continued)

*Primary Examiner* — Joseph Drodge
(74) *Attorney, Agent, or Firm* — K&L Gates LLP

(57) ABSTRACT

A dialysis system includes (i) a first home dialysis machine located at a first patient's home; (ii) a second home dialysis machine located at a second patient's home; (iii) a first modem in data communication with the first home dialysis machine; (iv) a second modem in data communication with the second home dialysis machine; (v) a clinician server associated with a dialysis center; (vi) a first clinician computer in data communication with the clinician server; (vii) a second clinician computer in data communication with the clinician server; (viii) a dialysis center modem in data communication with the clinician server; and (ix) a network in data communication with the first modem, the second modem and the dialysis center modem.

28 Claims, 42 Drawing Sheets

Related U.S. Application Data continuation of application No. 12/797,322, filed on Jun. 9, 2010, now Pat. No. 8,529,496, and a continuation of application No. 13/251,901, filed on Oct. 3, 2011, now Pat. No. 8,257,582, which is a continuation of application No. 12/170,230, filed on Jul. 9, 2008, now Pat. No. 8,062,513.

(51) Int. Cl.
 *B01D 61/32* (2006.01)
 *G06F 19/00* (2011.01)

(52) U.S. Cl.
 CPC ............ *A61M 1/281* (2014.02); *A61M 1/282* (2014.02); *B01D 61/32* (2013.01); *A61M 2205/502* (2013.01); *A61M 2209/01* (2013.01)

(58) Field of Classification Search
 CPC ........ A61M 2205/50; A61M 2205/502; A61M 2205/3553; A61M 2205/60; A61M 2205/6009; A61M 2205/6063; A61M 2209/01; A61M 2001/1601; A61M 2001/1603; A61M 2001/1611; A61M 2001/28; A61M 2001/281; A61M 2001/282; B01D 61/30; B01D 61/32; B01D 2311/24; G06F 19/3418
 USPC ............ 210/85, 96.1, 96.2, 141, 143, 321.6, 210/321.65, 321.71, 645–647; 604/4.01, 604/5.01, 6.01, 6.05, 6.09, 29, 65, 67; 600/300; 700/273; 702/19; 705/2, 3; 706/45–48, 61, 924
 See application file for complete search history.

(56) References Cited

U.S. PATENT DOCUMENTS

| | | |
|---|---|---|
| 3,375,716 A | 4/1968 | Hersch |
| 3,388,803 A | 6/1968 | Scott |
| 3,428,828 A | 2/1969 | Korzekwa et al. |
| 3,485,245 A | 12/1969 | Lahr et al. |
| 3,507,708 A | 4/1970 | Vignaud |
| 3,617,545 A | 11/1971 | Dubois et al. |
| 3,619,423 A | 11/1971 | Galletti et al. |
| 3,626,670 A | 12/1971 | Pecker |
| 3,656,873 A | 4/1972 | Schiff |
| 3,667,612 A | 6/1972 | Leonard |
| 3,689,204 A | 9/1972 | Prisk |
| 3,703,959 A | 11/1972 | Raymond |
| 3,707,967 A | 1/1973 | Kitrilakis et al. |
| 3,709,222 A | 1/1973 | DeVries |
| 3,727,612 A | 4/1973 | Sayers et al. |
| 3,730,183 A | 5/1973 | Goldsmith et al. |
| 3,792,643 A | 2/1974 | Scheafer |
| 3,799,873 A | 3/1974 | Brown |
| 3,809,241 A | 5/1974 | Alvine |
| 3,820,661 A | 6/1974 | Pages |
| 3,823,724 A | 7/1974 | Davis |
| 3,825,493 A | 7/1974 | Brown et al. |
| 3,839,200 A | 10/1974 | Gigou |
| 3,882,899 A | 5/1975 | Ginsberg |
| 3,884,808 A | 5/1975 | Scott |
| 3,902,490 A | 9/1975 | Jacobsen |
| 3,903,478 A | 9/1975 | Stuart |
| 3,926,797 A | 12/1975 | Gigou |
| 3,929,314 A | 12/1975 | Stratynski |
| 3,939,069 A | 2/1976 | Granger |
| 3,955,901 A | 5/1976 | Hamilton |
| 3,966,358 A | 6/1976 | Heimes et al. |
| 3,967,809 A | 7/1976 | Skantar |
| 3,976,574 A | 8/1976 | White |
| 3,979,284 A | 9/1976 | Granger |
| 4,008,712 A | 2/1977 | Nyboer et al. |
| 4,016,868 A | 4/1977 | Allison et al. |
| 4,071,040 A | 1/1978 | Moriarty |
| 4,079,007 A | 3/1978 | Hutchisson |
| 4,083,777 A | 4/1978 | Hutchisson |
| 4,086,653 A | 4/1978 | Gernes |
| 4,096,859 A | 6/1978 | Agarwal et al. |
| 4,118,314 A | 10/1978 | Yoshida |
| 4,126,132 A | 11/1978 | Portner et al. |
| 4,142,524 A | 3/1979 | Jassawalla et al. |
| 4,158,530 A | 6/1979 | Bernstein |
| 4,180,460 A | 12/1979 | Calari |
| 4,181,245 A | 1/1980 | Garrett et al. |
| 4,190,047 A | 2/1980 | Jacobsen et al. |
| 4,191,646 A | 3/1980 | Larsson et al. |
| 4,192,748 A | 3/1980 | Hyden |
| 4,194,536 A | 3/1980 | Stine et al. |
| 4,199,307 A | 4/1980 | Jassawalla |
| 4,204,545 A | 5/1980 | Yamakoshi |
| 4,212,738 A | 7/1980 | Henne |
| 4,235,231 A | 11/1980 | Schindler et al. |
| 4,236,880 A | 12/1980 | Archibald |
| 4,240,408 A | 12/1980 | Schael |
| 4,252,115 A | 2/1981 | Schael |
| 4,252,651 A | 2/1981 | Soderstrom |
| 4,265,601 A | 5/1981 | Mandoian |
| 4,269,708 A | 5/1981 | Bonomini et al. |
| 4,273,121 A | 6/1981 | Jassawalla |
| 4,276,175 A | 6/1981 | Bower |
| 4,277,226 A | 7/1981 | Archibald |
| 4,293,762 A | 10/1981 | Ogawa |
| 4,301,879 A | 11/1981 | Dubow |
| 4,303,376 A | 12/1981 | Siekmann |
| 4,310,141 A | 1/1982 | Tamura |
| 4,318,447 A | 3/1982 | Northcutt |
| 4,338,190 A | 7/1982 | Kraus et al. |
| 4,351,333 A | 9/1982 | Lazarus et al. |
| 4,370,983 A | 2/1983 | Lichtenstein |
| 4,375,346 A | 3/1983 | Kraus et al. |
| 4,381,003 A | 4/1983 | Buoncristiani |
| 4,381,005 A | 4/1983 | Bujan |
| 4,391,600 A | 7/1983 | Archibald |
| 4,396,382 A | 8/1983 | Goldhaber |
| 4,413,988 A | 11/1983 | Handt et al. |
| 4,430,048 A | 2/1984 | Fritsch |
| 4,456,218 A | 6/1984 | Kawabata et al. |
| 4,464,172 A | 8/1984 | Lichtenstein |
| 4,464,563 A | 8/1984 | Jewett |
| 4,468,222 A | 8/1984 | Lundquist |
| 4,475,900 A | 10/1984 | Popovich et al. |
| 4,476,005 A | 10/1984 | Tokinaga et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,482,584 A | 11/1984 | Hess et al. |
| 4,488,961 A | 12/1984 | Spencer |
| 4,498,900 A | 2/1985 | Buoncristiani |
| 4,504,038 A | 3/1985 | King |
| 4,530,759 A | 7/1985 | Schal |
| 4,532,414 A | 7/1985 | Shah et al. |
| 4,552,552 A | 11/1985 | Polaschegg et al. |
| 4,559,036 A | 12/1985 | Wunsch |
| 4,559,044 A | 12/1985 | Robinson et al. |
| 4,560,472 A | 12/1985 | Granmzow et al. |
| 4,574,876 A | 3/1986 | Aid |
| 4,579,642 A | 4/1986 | Niiyama et al. |
| 4,584,061 A | 4/1986 | Shelton |
| 4,586,920 A | 5/1986 | Peabody |
| 4,613,327 A | 9/1986 | Tegrarian et al. |
| 4,618,343 A | 10/1986 | Polaschegg |
| 4,620,846 A | 11/1986 | Goldberg et al. |
| RE32,303 E | 12/1986 | Lasker et al. |
| 4,629,015 A | 12/1986 | Fried et al. |
| 4,634,430 A | 1/1987 | Polaschegg |
| 4,639,245 A | 1/1987 | Pastrone et al. |
| 4,642,098 A | 2/1987 | Lundquist |
| 4,648,810 A | 3/1987 | Schippers et al. |
| 4,655,753 A | 4/1987 | Bellotti et al. |
| 4,657,490 A | 4/1987 | Abbott |
| 4,661,246 A | 4/1987 | Ash |
| 4,678,460 A | 7/1987 | Rosner |

(56) References Cited

U.S. PATENT DOCUMENTS

| | | |
|---|---|---|
| 4,680,445 A | 7/1987 | Ogawa |
| 4,694,848 A | 9/1987 | Jorgensen et al. |
| 4,696,671 A | 9/1987 | Epstein et al. |
| 4,703,773 A | 11/1987 | Hansen et al. |
| 4,710,166 A | 12/1987 | Thompson et al. |
| 4,717,117 A | 1/1988 | Cook |
| 4,718,890 A | 1/1988 | Peabody |
| 4,735,609 A | 4/1988 | Comeau et al. |
| 4,742,870 A | 5/1988 | Darone et al. |
| 4,747,822 A | 5/1988 | Peabody |
| 4,747,828 A | 5/1988 | Tseo |
| 4,765,907 A | 8/1988 | Scott |
| 4,769,151 A | 9/1988 | Shouldice |
| 4,778,356 A | 10/1988 | Hicks |
| 4,778,451 A | 10/1988 | Kamen |
| 4,784,576 A | 11/1988 | Bloom et al. |
| 4,794,942 A | 1/1989 | Yasuda et al. |
| 4,798,580 A | 1/1989 | DeMeo et al. |
| 4,804,360 A | 2/1989 | Kamen |
| 4,804,474 A | 2/1989 | Blum |
| 4,808,161 A | 2/1989 | Kamen |
| 4,816,019 A | 3/1989 | Kamen |
| 4,818,186 A | 4/1989 | Pastrone et al. |
| 4,818,190 A | 4/1989 | Pelmulder et al. |
| 4,823,552 A | 4/1989 | Ezell et al. |
| 4,826,482 A | 5/1989 | Kamen |
| 4,828,545 A | 5/1989 | Epstein et al. |
| 4,830,586 A | 5/1989 | Herter et al. |
| 4,842,584 A | 6/1989 | Pastrone |
| 4,844,074 A | 7/1989 | Kurucz |
| 4,847,470 A | 7/1989 | Bakke |
| 4,848,722 A | 7/1989 | Webster |
| 4,850,805 A | 7/1989 | Madsen et al. |
| 4,852,851 A | 8/1989 | Webster |
| 4,858,883 A | 8/1989 | Webster |
| 4,859,319 A | 8/1989 | Borsari |
| 4,865,584 A | 9/1989 | Epstein et al. |
| 4,869,286 A | 9/1989 | Williams et al. |
| 4,872,813 A | 10/1989 | Gorton et al. |
| 4,886,432 A | 12/1989 | Kimberlin |
| 4,889,812 A | 12/1989 | Guinn et al. |
| 4,895,657 A | 1/1990 | Polaschegg |
| 4,906,816 A | 3/1990 | Van Leerdam |
| 4,915,688 A | 4/1990 | Bischof et al. |
| 4,918,019 A | 4/1990 | Guinn |
| 4,923,598 A | 5/1990 | Schal |
| 4,925,152 A | 5/1990 | Huber |
| 4,927,411 A | 5/1990 | Pastrone et al. |
| 4,941,519 A | 7/1990 | Sestak et al. |
| 4,942,735 A | 7/1990 | Mushika et al. |
| 4,956,996 A | 9/1990 | Morris |
| 4,976,162 A | 12/1990 | Kamen |
| 4,976,683 A | 12/1990 | Gauthier et al. |
| 4,990,054 A | 2/1991 | Janocko |
| 5,000,664 A | 3/1991 | Lawless et al. |
| 5,002,471 A | 3/1991 | Perlov |
| 5,004,459 A | 4/1991 | Peabody et al. |
| 5,006,050 A | 4/1991 | Cooke et al. |
| 5,006,997 A | 4/1991 | Reich |
| 5,019,140 A | 5/1991 | Bowser et al. |
| 5,037,385 A | 8/1991 | O'Byrne |
| 5,043,201 A | 8/1991 | Cote |
| 5,053,003 A | 10/1991 | Dadson et al. |
| 5,062,774 A | 11/1991 | Kramer et al. |
| 5,063,937 A | 11/1991 | Ezenwa et al. |
| 5,073,167 A | 12/1991 | Carr et al. |
| 5,083,872 A | 1/1992 | Farling et al. |
| 5,088,515 A | 2/1992 | Kamen |
| 5,091,094 A | 2/1992 | Veech |
| 5,098,262 A | 3/1992 | Wecker et al. |
| 5,106,366 A | 4/1992 | Steppe |
| 5,108,367 A | 4/1992 | Epstein et al. |
| 5,116,203 A | 5/1992 | Natwick et al. |
| 5,125,069 A | 6/1992 | O'Boyle |
| 5,127,907 A | 7/1992 | Coutre et al. |
| 5,135,485 A | 8/1992 | Cohen et al. |
| 5,141,492 A | 8/1992 | Dadson et al. |
| 5,141,493 A | 8/1992 | Jacobsen et al. |
| 5,151,082 A | 9/1992 | Gorsuch et al. |
| 5,152,743 A | 10/1992 | Gorsuch et al. |
| 5,163,900 A | 11/1992 | Wortrich |
| 5,176,956 A | 1/1993 | Jevne et al. |
| 5,178,182 A | 1/1993 | Kamen |
| 5,180,896 A | 1/1993 | Gibby et al. |
| 5,194,157 A | 3/1993 | Ghezzi et al. |
| 5,211,849 A | 5/1993 | Kitaevich et al. |
| 5,215,312 A | 6/1993 | Knappe et al. |
| 5,240,614 A | 8/1993 | Ofsthun et al. |
| 5,245,693 A | 9/1993 | Ford et al. |
| 5,247,434 A | 9/1993 | Peterson et al. |
| 5,252,044 A | 10/1993 | Raines et al. |
| 5,261,876 A | 11/1993 | Popovich et al. |
| 5,277,820 A | 1/1994 | Ash |
| 5,284,470 A | 2/1994 | Beltz |
| 5,292,306 A | 3/1994 | Wynkoop et al. |
| 5,295,964 A | 3/1994 | Gautheir |
| 5,302,093 A | 4/1994 | Owens et al. |
| 5,311,899 A | 5/1994 | Isayama et al. |
| 5,316,452 A | 5/1994 | Bogen et al. |
| 5,324,422 A | 6/1994 | Colleran et al. |
| 5,326,476 A | 7/1994 | Grogan et al. |
| 5,332,372 A | 7/1994 | Reynolds |
| 5,334,139 A | 8/1994 | Jeppsson et al. |
| 5,338,293 A | 8/1994 | Jeppsson et al. |
| 5,344,292 A | 9/1994 | Rabenau et al. |
| 5,344,392 A | 9/1994 | Senniger et al. |
| 5,350,357 A | 9/1994 | Kamen et al. |
| 5,352,364 A | 10/1994 | Kruger et al. |
| 5,364,342 A | 11/1994 | Beuchat et al. |
| 5,370,674 A | 12/1994 | Farrell |
| 5,374,813 A | 12/1994 | Shipp |
| 5,378,126 A | 1/1995 | Abrahamson et al. |
| 5,381,510 A | 1/1995 | Ford et al. |
| 5,385,540 A | 1/1995 | Abbott et al. |
| 5,389,243 A | 2/1995 | Kaplan |
| 5,401,238 A | 3/1995 | Pirazzoli |
| 5,408,576 A | 4/1995 | Bishop |
| 5,409,355 A | 4/1995 | Brooke |
| 5,415,528 A | 5/1995 | Ogden et al. |
| 5,420,962 A | 5/1995 | Bakke |
| 5,421,208 A | 6/1995 | Packard et al. |
| 5,421,823 A | 6/1995 | Kamen et al. |
| 5,429,485 A | 7/1995 | Dodge |
| 5,431,626 A | 7/1995 | Bryant et al. |
| 5,438,510 A | 8/1995 | Bryant et al. |
| 5,439,587 A | 8/1995 | Stankowski et al. |
| 5,441,606 A | 8/1995 | Schlesinger et al. |
| 5,449,000 A | 9/1995 | Libke et al. |
| 5,458,468 A | 10/1995 | Ye et al. |
| 5,474,683 A | 12/1995 | Bryant et al. |
| 5,476,368 A | 12/1995 | Rabenau et al. |
| 5,482,438 A | 1/1996 | Anderson et al. |
| 5,482,440 A | 1/1996 | Dennehey et al. |
| 5,487,649 A | 1/1996 | Dorsey, III et al. |
| 5,508,912 A | 4/1996 | Schneiderman |
| 5,522,769 A | 6/1996 | DeGuiseppi |
| 5,536,412 A | 7/1996 | Ash |
| 5,540,265 A | 7/1996 | Polaschegg et al. |
| 5,540,568 A | 7/1996 | Rosen et al. |
| 5,542,919 A | 8/1996 | Simon et al. |
| 5,554,013 A | 9/1996 | Owens et al. |
| 5,556,263 A | 9/1996 | Jacobsen et al. |
| 5,563,584 A | 10/1996 | Rader et al. |
| 5,572,992 A | 11/1996 | Kankkunen et al. |
| 5,580,460 A | 12/1996 | Polaschegg |
| 5,582,732 A | 12/1996 | Mao et al. |
| 5,583,948 A | 12/1996 | Shibayama |
| 5,586,868 A | 12/1996 | Lawless et al. |
| 5,588,816 A | 12/1996 | Abbott et al. |
| 5,601,420 A | 2/1997 | Warner et al. |
| 5,603,354 A | 2/1997 | Jacobsen et al. |
| 5,608,193 A | 3/1997 | Almogaibil |
| 5,609,572 A | 3/1997 | Lang |
| 5,620,312 A | 4/1997 | Hyman et al. |

(56) References Cited

U.S. PATENT DOCUMENTS

| | | |
|---|---|---|
| 5,628,908 A | 5/1997 | Kamen et al. |
| 5,632,606 A | 5/1997 | Jacobsen et al. |
| 5,634,896 A | 6/1997 | Bryant et al. |
| 5,636,653 A | 6/1997 | Titus |
| 5,641,405 A | 6/1997 | Keshaviah et al. |
| 5,643,201 A | 7/1997 | Peabody et al. |
| 5,645,734 A | 7/1997 | Kenley et al. |
| 5,654,537 A | 8/1997 | Prater |
| 5,669,764 A | 9/1997 | Behringer et al. |
| 5,670,057 A | 9/1997 | Chen et al. |
| 5,671,362 A | 9/1997 | Cowe et al. |
| 5,676,530 A | 10/1997 | Nazarifar |
| 5,683,381 A | 11/1997 | Carr et al. |
| 5,685,988 A | 11/1997 | Malchesky |
| 5,690,160 A | 11/1997 | Sutton et al. |
| 5,690,614 A | 11/1997 | Carr et al. |
| 5,698,083 A | 12/1997 | Glass |
| 5,718,569 A | 2/1998 | Holst |
| 5,720,313 A | 2/1998 | Grobbel |
| 5,722,947 A | 3/1998 | Jeppsson et al. |
| 5,724,478 A | 3/1998 | Thweatt |
| 5,729,653 A | 3/1998 | Magliochetti et al. |
| 5,735,284 A | 4/1998 | Tsoglin et al. |
| 5,752,234 A | 5/1998 | Withers |
| 5,758,563 A | 6/1998 | Robinson |
| 5,778,643 A | 7/1998 | Tacchini |
| 5,788,851 A | 8/1998 | Kenley et al. |
| 5,790,752 A | 8/1998 | Anglin et al. |
| 5,792,367 A | 8/1998 | Mattisson et al. |
| 5,800,397 A | 9/1998 | Wilson et al. |
| 5,807,075 A | 9/1998 | Jacobsen et al. |
| 5,816,779 A | 10/1998 | Lawless et al. |
| 5,836,908 A | 11/1998 | Beden et al. |
| 5,843,474 A | 12/1998 | Williams |
| 5,858,186 A | 1/1999 | Glass |
| 5,858,238 A | 1/1999 | McRea et al. |
| 5,867,821 A | 2/1999 | Ballantyne et al. |
| 5,871,566 A | 2/1999 | Rutz |
| 5,875,282 A | 2/1999 | Jordan et al. |
| 5,912,818 A | 6/1999 | McGrady et al. |
| 5,919,154 A | 7/1999 | Toavs et al. |
| 5,919,369 A | 7/1999 | Ash |
| 5,921,951 A | 7/1999 | Morris |
| 5,924,975 A | 7/1999 | Goldowsky |
| 5,925,011 A | 7/1999 | Faict et al. |
| 5,925,014 A | 7/1999 | Teeple, Jr. |
| 5,928,196 A | 7/1999 | Johnson et al. |
| 5,931,647 A | 8/1999 | Jacobsen et al. |
| 5,938,634 A | 8/1999 | Packard |
| 5,944,495 A | 8/1999 | Jacobsen et al. |
| 5,944,684 A | 8/1999 | Roberts et al. |
| 5,945,831 A | 8/1999 | Sargent et al. |
| 5,951,863 A | 9/1999 | Kruger et al. |
| 5,960,160 A | 9/1999 | Clark et al. |
| 5,965,433 A | 10/1999 | Gardetto et al. |
| 5,980,481 A | 11/1999 | Gorsuch |
| 5,989,238 A | 11/1999 | Ginsburg |
| 5,989,423 A | 11/1999 | Kamen et al. |
| 5,997,502 A | 12/1999 | Reilly et al. |
| 6,007,310 A | 12/1999 | Jacobsen et al. |
| 6,017,194 A | 1/2000 | North, Jr. |
| 6,017,198 A | 1/2000 | Traylor et al. |
| 6,017,318 A | 1/2000 | Gauthier et al. |
| 6,036,668 A | 3/2000 | Mathis |
| 6,041,801 A | 3/2000 | Gray et al. |
| 6,065,941 A | 5/2000 | Gray et al. |
| 6,069,343 A | 5/2000 | Kolowich |
| 6,109,254 A | 8/2000 | Reinke et al. |
| 6,110,617 A | 8/2000 | Feres |
| 6,122,972 A | 9/2000 | Crider |
| 6,126,403 A | 10/2000 | Yamada |
| 6,129,699 A | 10/2000 | Haight et al. |
| 6,133,547 A | 10/2000 | Maynard |
| 6,139,528 A | 10/2000 | Kistner et al. |
| 6,142,974 A | 11/2000 | Kistner et al. |
| 6,146,359 A | 11/2000 | Carr et al. |
| 6,165,154 A | 12/2000 | Gray et al. |
| 6,175,688 B1 | 1/2001 | Cassidy et al. |
| 6,208,107 B1 | 3/2001 | Maske et al. |
| 6,223,130 B1 | 4/2001 | Gray et al. |
| 6,228,033 B1 | 5/2001 | Kööbi et al. |
| 6,228,047 B1 | 5/2001 | Dadson |
| 6,229,957 B1 | 5/2001 | Baker |
| 6,231,320 B1 | 5/2001 | Lawless et al. |
| 6,234,992 B1 | 5/2001 | Haight et al. |
| 6,236,809 B1 | 5/2001 | Cassidy et al. |
| 6,246,831 B1 | 6/2001 | Seitz et al. |
| 6,246,894 B1 | 6/2001 | Steuer et al. |
| 6,248,093 B1 | 6/2001 | Moberg |
| 6,254,567 B1 | 7/2001 | Treu et al. |
| 6,257,265 B1 | 7/2001 | Brunner et al. |
| 6,259,074 B1 | 7/2001 | Brunner et al. |
| 6,261,261 B1 | 7/2001 | Gordon |
| 6,270,673 B1 | 8/2001 | Belt et al. |
| 6,278,084 B1 | 8/2001 | Maynard |
| 6,283,719 B1 | 9/2001 | Frantz et al. |
| 6,293,921 B1 | 9/2001 | Shinmoto et al. |
| 6,293,926 B1 | 9/2001 | Sorensen et al. |
| 6,302,653 B1 | 10/2001 | Bryant et al. |
| 6,343,614 B1 | 2/2002 | Gray et al. |
| 6,364,857 B1 | 4/2002 | Gray et al. |
| 6,385,593 B2 | 5/2002 | Linberg |
| 6,416,293 B1 | 7/2002 | Bouchard et al. |
| 6,463,394 B1 | 10/2002 | Von Bahr |
| 6,484,383 B1 | 11/2002 | Herklotz |
| 6,595,948 B2 | 7/2003 | Suzuki et al. |
| 6,615,077 B1 | 9/2003 | Zhu et al. |
| 6,672,841 B1 | 1/2004 | Herklotz et al. |
| 6,673,314 B1 | 1/2004 | Burbank et al. |
| 6,685,831 B2 | 2/2004 | Dönig et al. |
| 6,733,676 B2 | 5/2004 | Takai |
| 6,743,201 B1 | 6/2004 | Dönig |
| 6,752,172 B2 | 6/2004 | Lauer |
| 6,764,761 B2 | 7/2004 | Eu et al. |
| 6,814,547 B2 | 11/2004 | Childers et al. |
| 6,835,175 B1 | 12/2004 | Porumbescu |
| 6,869,538 B2 | 3/2005 | Yu et al. |
| 6,881,344 B2 | 4/2005 | Vasta et al. |
| 6,882,982 B2 | 4/2005 | McMenimen et al. |
| 6,925,447 B2 | 8/2005 | McMenimen et al. |
| 6,929,751 B2 | 8/2005 | Bowman, Jr. et al. |
| 6,939,111 B2 | 9/2005 | Huitt et al. |
| 6,948,918 B2 | 9/2005 | Hansen |
| 6,953,323 B2 | 10/2005 | Childers et al. |
| 7,029,456 B2 | 4/2006 | Ware et al. |
| 7,033,539 B2 | 4/2006 | Krensky et al. |
| 7,076,303 B2 | 7/2006 | Linberg |
| 7,087,036 B2 | 8/2006 | Busby et al. |
| 7,115,228 B2 | 10/2006 | Lundtveit et al. |
| 7,142,118 B2 | 11/2006 | Hamilton et al. |
| 7,153,286 B2 | 12/2006 | Busby et al. |
| 7,175,606 B2 | 2/2007 | Bowman, Jr. et al. |
| 7,208,092 B2 | 4/2007 | Micheli |
| 7,214,210 B2 | 5/2007 | Kamen et al. |
| 7,225,030 B2 | 5/2007 | Kroll et al. |
| 7,228,170 B2 | 6/2007 | Zhu et al. |
| 7,230,521 B2 | 6/2007 | Terenna |
| 7,252,230 B1 | 8/2007 | Sheikh et al. |
| 8,062,513 B2 * | 11/2011 | Yu .............. A61M 1/28 210/143 |
| 8,257,582 B2 * | 9/2012 | Yu .............. A61M 1/28 210/138 |
| 8,512,554 B2 * | 8/2013 | Yu .............. A61M 1/28 210/138 |
| 9,141,760 B2 * | 9/2015 | Yu .............. A61M 1/28 |
| 2001/0018937 A1 | 9/2001 | Nemoto |
| 2001/0034502 A1 | 10/2001 | Moberg et al. |
| 2002/0045851 A1 | 4/2002 | Suzuki et al. |
| 2002/0062109 A1 | 5/2002 | Lauer |
| 2002/0077598 A1 | 6/2002 | Yap et al. |
| 2002/0081109 A1 | 6/2002 | Mitsunaga et al. |
| 2002/0082728 A1 | 6/2002 | Mueller et al. |
| 2002/0103453 A1 | 8/2002 | Burbank et al. |
| 2003/0208113 A1 | 11/2003 | Mault et al. |

(56) References Cited

U.S. PATENT DOCUMENTS

| | | | |
|---|---|---|---|
| 2003/0220598 A1 | 11/2003 | Busby et al. | |
| 2004/0092841 A1 | 5/2004 | Singer | |
| 2004/0111293 A1 | 6/2004 | Firanek et al. | |
| 2004/0111294 A1 | 6/2004 | McNally et al. | |
| 2004/0122705 A1* | 6/2004 | Sabol | G06F 19/324 705/2 |
| 2004/0167465 A1* | 8/2004 | Mihai | A61B 5/0002 604/67 |
| 2004/0181528 A1 | 9/2004 | Tirinato et al. | |
| 2005/0020960 A1 | 1/2005 | Brugger et al. | |
| 2005/0055242 A1 | 3/2005 | Bello et al. | |
| 2005/0131332 A1 | 6/2005 | Kelly et al. | |
| 2005/0256745 A1 | 11/2005 | Dalton | |
| 2006/0113249 A1 | 6/2006 | Childers et al. | |
| 2007/0007208 A1 | 1/2007 | Brugger et al. | |
| 2007/0228068 A1 | 10/2007 | Schneider et al. | |
| 2008/0015493 A1 | 1/2008 | Childers et al. | |
| 2008/0125693 A1 | 5/2008 | Gavin et al. | |
| 2008/0149563 A1* | 6/2008 | Ash | A61M 1/16 210/646 |
| 2008/0161751 A1 | 7/2008 | Plahey et al. | |
| 2008/0296226 A1 | 12/2008 | Gotch | |
| 2009/0275881 A1 | 11/2009 | Lo et al. | |
| 2009/0275883 A1 | 11/2009 | Chapman et al. | |
| 2011/0004351 A1 | 1/2011 | Kelly et al. | |
| 2013/0150780 A1 | 6/2013 | Childers et al. | |

FOREIGN PATENT DOCUMENTS

| | | |
|---|---|---|
| DE | 19919572 | 11/2000 |
| EP | 0 011 935 | 6/1980 |
| EP | 0 013 334 | 7/1980 |
| EP | 0 028 371 | 5/1981 |
| EP | 0 033 096 | 8/1981 |
| EP | 0 052 004 | 5/1982 |
| EP | 0 097 432 | 1/1984 |
| EP | 0 121 085 | 10/1984 |
| EP | 0 157 024 | 10/1985 |
| EP | 0 204 260 | 12/1986 |
| EP | 0 206 195 | 12/1986 |
| EP | 0 248 632 | 12/1987 |
| EP | 0 258 424 | 3/1988 |
| EP | 0 311 848 | 4/1989 |
| EP | 0 319 272 | 6/1989 |
| EP | 0 402 505 | 12/1990 |
| EP | 0403294 | 12/1990 |
| EP | 0 410 125 | 1/1991 |
| EP | 0 575 970 | 12/1993 |
| EP | 0 650 739 | 5/1995 |
| EP | 0 660 725 | 7/1995 |
| EP | 0 847 769 | 6/1998 |
| EP | 0 856 320 | 8/1998 |
| EP | 0 856 321 | 8/1998 |
| EP | 0 856 322 | 8/1998 |
| EP | 0 928 615 | 7/1999 |
| EP | 0 947 814 | 10/1999 |
| EP | 0 956 876 | 11/1999 |
| EP | 1 110 564 | 6/2001 |
| EP | 1 110 565 | 6/2001 |
| EP | 1 205 144 | 5/2002 |
| EP | 1235614 | 9/2002 |
| EP | 0 957 954 | 5/2003 |
| EP | 1 403 519 | 3/2004 |
| EP | 1535576 A1 | 6/2005 |
| EP | 1 546 556 | 12/2006 |
| EP | 1 754 890 | 2/2007 |
| EP | 1 938 849 | 2/2008 |
| FR | 2 371 931 | 6/1978 |
| FR | 2 440 740 | 6/1980 |
| GB | 1 326 236 | 8/1973 |
| GB | 2 053 378 | 2/1981 |
| GB | 2 069 706 | 8/1981 |
| GB | 2 122 509 | 1/1984 |
| GB | 2 124 511 | 2/1984 |
| GB | 2 135 598 | 9/1984 |
| JP | 57161511 | 10/1982 |
| JP | H03-96850 | 10/1991 |
| JP | 6-106033 | 4/1994 |
| JP | 10234849 | 9/1998 |
| JP | 11347115 | 12/1999 |
| JP | 2002-113096 | 4/2002 |
| JP | 2002-291879 | 10/2002 |
| JP | 2003-047657 | 2/2003 |
| JP | 2003/275301 | 9/2003 |
| JP | 2003-275301 | 9/2003 |
| JP | 2003/533243 | 11/2003 |
| JP | 2003533243 | 11/2003 |
| JP | 2006-520037 | 8/2006 |
| JP | 2007/029705 | 2/2007 |
| JP | 2007-029705 | 2/2007 |
| JP | 2008-045955 | 2/2008 |
| JP | 2008/045955 | 2/2008 |
| SE | 331736 | 1/1971 |
| WO | WO 84/02473 | 7/1984 |
| WO | WO 85/01879 | 5/1985 |
| WO | WO 85/04813 | 11/1985 |
| WO | WO 86/01115 | 2/1986 |
| WO | WO 87/05223 | 9/1987 |
| WO | WO 89/01795 | 3/1989 |
| WO | WO 90/13795 | 11/1990 |
| WO | WO 91/02484 | 3/1991 |
| WO | WO 92/11046 | 7/1992 |
| WO | WO 92/15349 | 9/1992 |
| WO | WO 92/19153 | 11/1992 |
| WO | WO 93/00938 | 1/1993 |
| WO | WO 93/01845 | 2/1993 |
| WO | WO 94/20154 | 9/1994 |
| WO | WO 94/20158 | 9/1994 |
| WO | 94/24929 | 11/1994 |
| WO | WO 95/02559 | 1/1995 |
| WO | WO 95/35124 | 12/1995 |
| WO | WO 96/25214 | 8/1996 |
| WO | WO 96/32883 | 10/1996 |
| WO | WO 98/17333 | 4/1998 |
| WO | WO 98/22167 | 5/1998 |
| WO | 98/35747 | 8/1998 |
| WO | WO 98/51211 | 11/1998 |
| WO | WO 99/06082 | 2/1999 |
| WO | 99/36657 | 7/1999 |
| WO | WO 99/37335 | 7/1999 |
| WO | 99/46657 | 9/1999 |
| WO | 99/52025 | 10/1999 |
| WO | WO 00/20050 | 4/2000 |
| WO | WO 00/31553 | 6/2000 |
| WO | WO 00/44018 | 7/2000 |
| WO | WO 00/57928 | 10/2000 |
| WO | WO 01/37786 | 5/2001 |
| WO | 01/41831 | 6/2001 |
| WO | WO 01/91829 | 12/2001 |
| WO | WO 02/13691 | 2/2002 |
| WO | 2004/006776 | 1/2004 |
| WO | WO 2004/029457 | 4/2004 |
| WO | 2008/008281 | 1/2008 |

OTHER PUBLICATIONS

Tsavdaris et al., "Monitoring and Supporting Home Haemodialysis using Telematic Services," distributed at 8th Proceedings of the Mediterranean Conference on Biological Engineering and Computing, Jun. 14th to 17th, 1998 in Lemesos, Cyprus.
Office Action for Mexican Patent Application No. Mx/a/2011/000325 dated Apr. 4, 2013.
Office Action for Japanese Patent Application No. 2011-517612 dated Aug. 14, 2013.
International Search Report and the Written Opinion for International Application No. PCT/US2009/050073 dated May 3, 2010.
European Office Action mailed Jul. 30, 2014 for related European Appln. No. 09790207.6 (4 pages).
Japanese Office Action issued Sep. 17, 2013 for related Japanese Appln. No. 2011-517606.
U.S. Appl. No. 10/155,660, filed May 24, 2002, Bowman, Jr. et al.

(56) References Cited

OTHER PUBLICATIONS

U.S. Appl. No. 10/155,752, filed May 24, 2002, Busby et al.
U.S. Appl. No. 10/155,753, filed May 24, 2002, Hopping.
U.S. Appl. No. 10/155,787, filed May 24, 2002, Busby et al.
U.S. Appl. No. 11/187,515, filed Jul. 22, 2005, Childers et al.
U.S. Appl. No. 11/614,858, filed Dec. 21, 2006, Busby et al.
Action Closing Prosecution (nonfinal) Jan. 15, 2010.
Appendix A: U.S. Pat. No. 3,620,215 Alone and in Combination with Other Prior Art References.
Appendix B: Pericycle Product and References Describing the Pericycle in Combination with Other Prior Art References.
Appendix C: U.S. Pat. No. 4,412,917 in Combination with Other Prior Art References.
Appendix D: U.S. Pat. No. 4,498,900 in Combination with Other Prior Art References.
Appendix E: U.S. Pat. No. 3,545,438 in Combination with Other Prior Art References.
Appendix F: U.S. Pat. No. 5,004,459 in Combination with Other Prior Art References.
Appendix G: Bilstad and Kruger References Together or in Combination with Other Prior Art References.
Appendix H: Combination of 90/2 and Bilstad Together, or in Combination with Other References.
Appendix I: French Patent Nos. 2,371,931 and 2,240,740 in Combination with Other Prior Art References.
Appendix J: AP Hauni References in Combination with Other Prior Art References.
Appendix K: The SIF 901 References in Combination with Other Prior Art References.
Appendix L: "PD in the 90s" in Combination with Other Prior Art References.
Article entitled: "A Practicle Solution for Clinical and Quality Assurance"; written by Gambro (article undated). Date Unknown.
Assorted Photos of dialysis machine with and without casing on.
Baxter Renalsoft Patient Management Software Suite description [online] [retrieved Aug. 21, 2008, available prior to Jul. 9, 2008]. Retrieved from the Internet at <URL: http://www.baxter.com/products/renal/software/renalsoft.html>. Publication Date Unknown.
Bergstrom et al., An Automated Apparatus for Peritoneal Dialysis with Volumetric Fluid Balance Measurement, reprinted from Dialysis & Transplantation, Jun./Jul. 1976.
Blumenkrantz and Roberts, Progress in Peritoneal Dialysis: a Historical Prospective, Contributions to Nephrology, vol. 17, pp. 101-110 (1979).
Blumenkrantz et al., Applications of the Redy Sorbent System to Hemodialysis and Peritoneal Dialysis, Artificial Organs, vol. 3, No. 3 (Aug. 1979).
Blumenkrantz et al., Development of a Sorbent Peritoneal Dialysate Regeneration System—A Progress Report, European Dialysis and Transplant Association 1978.
Bran & Luebbe GmbH, Diaphragm Metering Pumps, Chem. Eng'g Progress, Apr. 1987, at 18-24.
Brighton, Pierce, Landis & Rosenberg, Measuring Cardiac Output of Pneumatically Driven Total Artificial Hearts, published in 30th Anniversary Conference on Engineering in Medicine and Biology: Proceedings, vol. 19 (Nov. 5-9, 1977).
Brochure entitled Fresenius Delivers 90/2 Peritoneal Therapy Cycler (Apr. 2001).
Brochure entitled, AP Hauni: Automatisches Peritonealdialyse-Great (1970).
Brochure entitled, for Volume Measurement, Temperature Control and Cycling of Dialysing Fluid, Peritoneal Dialyser PD700, 1970.
Brochure entitled, Peritoneal Dialyser PD700, May 1979.
Brochure entitled, REDY Universal Re-circulating Dialysate System.
Brochure entitled, SIF 901 Perugia.
Callsen, U., Peritoneal-Dialysator PD700, Prakt. Anasth. 9 (1974).
CMS 08—Handbook, published by Fresenius AG, 4 Edition 1988.

Defendants' Final Invalidity Contentions for U.S. Pat. No. 6,814,547, *Baxter Healthcare Corporation v. Fresenius Medical Care Holdings*, Case No. C 07-01359 PJH (JL), filed Apr. 1, 2009.
Defendants' Preliminary Invalidity Contentions for U.S. Pat. No. 5,421,823, *Baxter Healthcare Corporation v. Fresenius Medical Care Holdings*, Case No. C 07-01359 PJH (JL), filed Aug. 24, 2007.
Defendants' Preliminary Invalidity Contentions for U.S. Pat. No. 6,503,062, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Pat. No. 6,808,369, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Pat. No. 5,324,422, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Pat. No. 5,438,510, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Pat. No. 6,814,547, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Pat. No. 5,431,626, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Pat. No. 6,929,751, *Baxter Healthcare Corporation v. Fresenius Medical Care Holdings*, Case No. C 07-01359 PJH (JL), filed Jan. 31, 2008.
Defendants' Preliminary Invalidity Contentions for U.S. Pat. No. 7,083,719, *Baxter Healthcare Corporation v. Fresenius Medical Care Holdings*, Case No. C 07-01359 PJH (JL), filed Jan. 31, 2008.
Defendants' Supplemental Invalidity Contentions for U.S. Pat. No. 5,421,823, *Baxter Healthcare Corporation v. Fresenius Medical Care Holdings*, Case No. C 07-01359 PJH (JL), filed Jan. 31, 2008.
Diaz-Buxo, CCPD is even better than CAPD, Kidney International, vol. 28, Suppl. 17, pp. S-26-S-28 (1985).
Diaz-Buxo, CCPD Technique and Current Clinical Experience (1982).
Diaz-Buxo, Current Status of Continuous Cyclic Peritoneal Dialysis (CCPD), Peritoneal Dialysis International, vol. 9, pp. 9-14 (1989).
Diaz-Buxo, et al., Continuous Cyclic Peritoneal Dialysis: A Preliminary Report, Artificial Organs, vol. 5, No. 2, pp. 157-161 (May 1981).
Diaz-Buxo, Issues in Nephrology: Continuous Cyclic Peritoneal Dialysis, NAPHT News, Feb. 1983, pp. 12-14.
Diaz-Buxo, Peritoneal Dialysis Reverse Osmosis Machines and Cyclers, Dialysis Therapy, pp. 41-48 (1986).
Drukker et al., Replacement of Renal Function by Dialysis, 2nd Ed., Ch. 21, 1983.
Elsevier Science Ltd., Air-Operated Diaphragm Pumps, World Pumps, Jan. 1996, at 38.
European Search Report issued Jan. 12, 2009, for corresponding International Application No. PCT/US2009/050062.
Exhibit A, Credentials of Ronald J. Adrian.
Exhibit B, Materials Considered by Ronald J. Adrian.
Expert Report on Development of the PD700 and Motivation to Combine the PD700 and U.S. Pat. No. 5,088,515, Sven Olofsson, Apr. 24, 2009.
Expert Witness Report of Fred K. Forster: Analysis of Obviousness of Certain Asserted Claims of U.S. Pat. Nos. 5,431,626; 5,324,422; and 5,438,510, Apr. 24, 2009.
Expert Witness Report of Juan G. Santiago Regarding Lack of Written Description, Non-Enablement, and Indefiniteness of the Asserted Claims of U.S. Pat. Nos. 5,421,823; 5,324,422; 5,438,510; and 5,431,626, Apr. 24, 2009.
Expert Witness Report of Ronald J. Adrian Regarding Lack of Written Description, Lack of Enablement, and Indefiniteness of the Asserted Claim (Claim 12) of U.S. Pat. No. 6,814,547, Apr. 24, 2009.
Final Office Action for U.S. Appl. No. 11/617,527 dated May 5, 2009.
Final Office Action for U.S. Appl. No. 11/617,543 dated Jul. 22, 2009.

(56) References Cited

OTHER PUBLICATIONS

Final Office Action for U.S. Appl. No. 11/617,543 dated May 30, 2008.
Flessner, Michael F. article entitled: "Computerized Kinetic Modeling: A New Tool in the Quest for Adequacy in Peritoneal Dialysis"; Peritoneal Dialyssi International, vol. 17, pp. 581-585 (1997).
Freedom Cycler Document Index.
Fresenius 90/2 Brochure (Apr. 2001).
Fresenius 90/2 Brochure (Jul. 1993).
Fresenius 90/2 Cycler Box Contents.
Fresenius 90/2 Cycler Parts List (Nov. 6, 1997).
Fresenius 90/2 Cycler Software, Version 3.96 (Jan. 24, 1992).
Fresenius 90/2 Directions for Use.
Fresenius 90/2 Document Index.
Fresenius 90/2 PD Cycler Set Patient Information Card.
Fresenius 90/2 Peritoneal Therapy Cycler (on information and belief, on sale in United States by 1991).
Fresenius 90/2 Peritoneal Therapy Cycler Operator's Instructions, dated 2000.
Fresenius 90/2 Quick Reference.
Fresenius Freedom Cycler Operating Instructions. undated.
Fresenius Medical Care Acute Dialysis Machine Operating Instructions for acu-men, Software Version 1.0.
Fresenius Medical Care Operating Instructions for sleep-safeTM, Software Version 1.0, Part No. 677 805 1.
Fresenius Medical Care Slide Presentation for sleep-safeTM.
Fresenius Medical Care Technical Manual for sleep-safeTM, Part No. 677 807 1.
Fresenius USA/Delmed 90/2 Peritoneal Dialysis System Operators Manual, dated Feb. 6, 1991.
Gambro Laboratoriesvar APD written by Gambro Lundia AB, Lundia AB, Lund, Sweden, Jan. 1999, printed by Elanders Skogs Grafiska AB, Rev. 2, May 2001.
Gambro PDC—Personal Dialysis Capacity [online] [retrieved Nov. 10, 2006]. Retrieved from the Internet at <URL: http://www.em.gambro.com/Pages/InfoPage.aspx?id=4788.html>. Publication Date Unknown.
Gambro PDC Measuting in APD Patient Manual written by Gambro Lundia AB, Lund, Sweden, Oct. 1998, printed by Elanders Skogs Grafiska AB, Rev. 3, Jan. 2001.
International Preliminary Report on Patentability for International Application No. PCT/US2009/050062 mailed on Oct. 5, 2010.
Japanese Office Action for 2011-231549 dated Mar. 21, 2013.
Japanese Office Action for Application No. 2009-165169 mailed Mar. 8, 2012.
Lewin and Maxwell, Sorbent-Based Regenerating Peritoneal Dialysis, Sorbents and Their Clinical Applications, pp. 353-374 (1980).
Lewin et al., Sorbent for Application in the Treatment of ESRD Patients, Annual Progress Report re Contract #N01-AM-9-2215, submitted Jun. 22, 1982.
Mexican Office Action received May 20, 2013 for related Appln. No. MX/A/2011/000326.
Mrava, Gene, L, Mock Circulation Systems for Artificial Hearts, published in Advances in Biomedical Engineering and Medical Physics: Cardiac Engineering, vol. 3.
Non-final Office Action for U.S. Appl. No. 11/617,527 dated Aug. 12, 2009.
Non-final Office Action for U.S. Appl. No. 11/617,527 dated Nov. 24, 2008.
Non-final Office Action for U.S. Appl. No. 11/617,543 dated Oct. 20, 2008.
Non-final Office Action for U.S. Appl. No. 11/617,543 dated Sep. 24, 2007.
Opening Expert Witness Report of Dr. Darrell Long Regarding Technical Features of the High Flow Peritoneal Dialysis and Personal Cycler Machines, Apr. 24, 2009.
Opening Expert Witness Report of Dr. Juan Santiago Regarding Anticipation and Obviousness of the Claims of U.S. Pat. Nos. 6,503,062 and 6,808,369 in view of the Prior Art and based on the Indefiniteness, Lack of Enablement, and Lack of Written Description of Certain Claims of U.S. Pat. Nos. 6,503,062 and 6,808,369, Apr. 24, 2009.
Opening Expert Witness Report of Dr. Martin Roberts Regarding a History of Peritoneal Dialysis and the Obviousness and Consequent Invalidity of the Asserted Claims of U.S. Pat. No. 5,421,823, Apr. 24, 2009.
Opening Expert Witness Report of William K. Durfee Regarding whether Certain Claims of U.S. Pat. Nos. 5,324,422, 5,421,823, 5,431,626 and U.S. Pat. No. 5,438,510 were Ready for Patenting, Apr. 24, 2009.
Operating Instructions, Peritoneal Dialyser PD700, For Ser. No. 300.
Operators Instructions for Fresenius 90/2 Peritoneal Therapy Cycler.
Operator's Instructions, Fresenius 90/2 Peritoneal Therapy Cycler (Rev. C. copyright 1991-2000).
PD700 Peritoneal Dialyser Users Hand-book, Dec. 1977.
Peritoneal Dialyser PD700 Instruction Manual.
Peritoneal Dialyser PD700 Service Manual, Jun. 1977.
Phillips, Brighton & Pierce, Artificial Heart Evaluation Using Flow Visualization Techniques, published in Transactions: American Society for Artificial Internal Organs, vol. XVIII (1972).
Photo of dialysis machine.
Photo of dialysis patient connected to machine.
Piazolo et al., Erfahrungen mit einem neuen vollautomatsischen Paritoneal-dialysegerat, Munchener Medizinische Wochenschrift, 1972.
Product Evaluation Reports: Peritoneal Dialysis Machine "Pac-X," Hospital Materials Management, vol. 12, No. 11, p. 16 (Nov. 1987).
Ratnu et al., A New Technique—Semicontinuous Rapid Flow, High Volume Exchange—for Effective Peritoneal Dialysis in Shorter Periods, Nephron, vol. 31, pp. 159-163 (1982).
Reexamination Certificate Issued Feb. 8, 2011.
Reexamination Non-Final Office Action Mar. 11, 2009.
Request for Inter Partes Reexamination Request Jan. 8, 2009.
Response after Non-Final Action—Owner Timely Jun. 11, 2009.
Ronco et al., "Evolution of Machines for Automated Peritoneal Dialysis", Technical Aspects and Solutions for ADP, 1999, pp. 142-161, vol. 129.
Schalbach, Bucherl & Franke, An Electronically Controlled Implantable Auxiliary Ventricle, published in Advances in Biomedical Engineering and Medical Physics: Cardiac Engineering, vol. 3.
Skotselanvisning for Peritoneal—Dialysapparat PD700.
Sleep-safeTM Brochure.
Software Change Requests (Jul. 8, 1991-Oct. 3, 1992).
Specification entitled Inpersol Cycler 3000 Operating Manual, List No. 21952-04, dated 1990.
Technical Note, PD700 Peritoneal Dialyser, Jan. 29, 1979.
Third Party Requester Comments after Non-Final Action Jul. 10, 2009.
Training aid entitled Learning to Use the Inpersol Cycler 3000, dated Jul. 1991.
Translation of brochure entitled, SIF 901 Perugia.
Translation of Certificate for translation of brochure entitled, SIF 901 Perugia.
Twardowski, Peritoneal Dialysis: Current Technology and techniques, Postgraduate Medicine, vol. 85, No. 5 (Apr. 1989).
Vaccarino, Donald X. Memorandum entitled 90/2 History File (1991-1992).
Final Office Action for Application No. 2011-517606 due date Jan. 17, 2014.
Mexican Office Action mailed Jul. 1, 2015 for Mexican Appln. No. MX/a/2014/008333.

\* cited by examiner

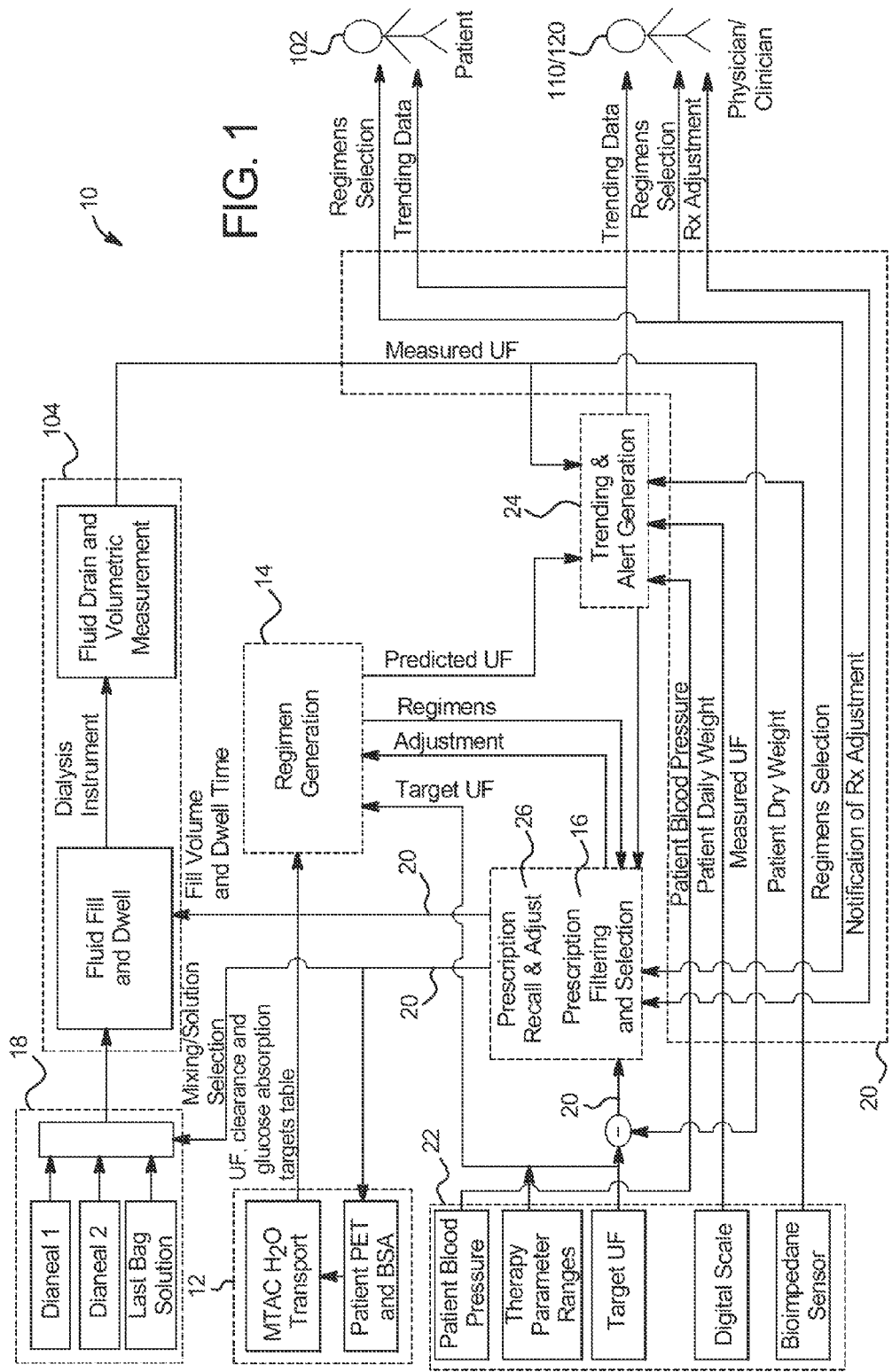

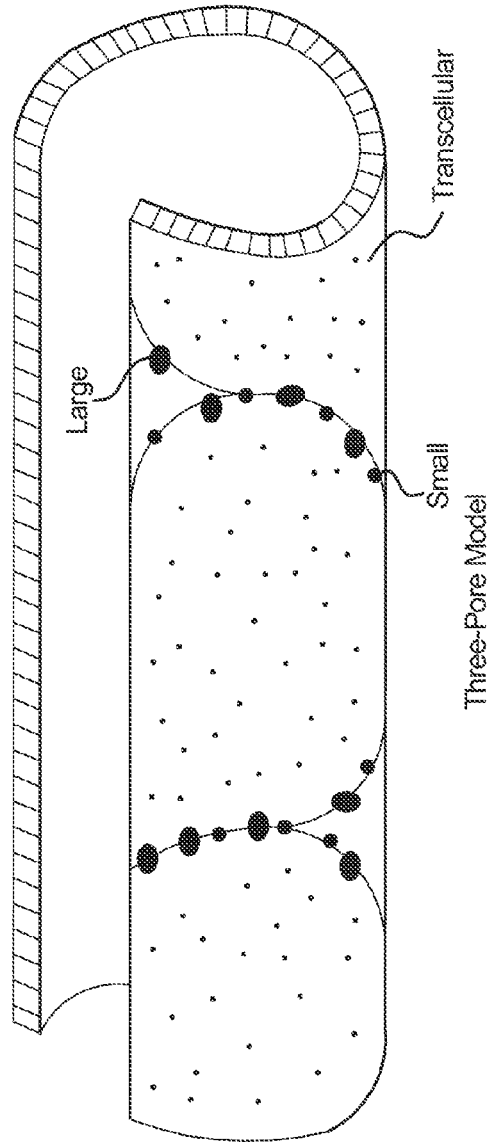

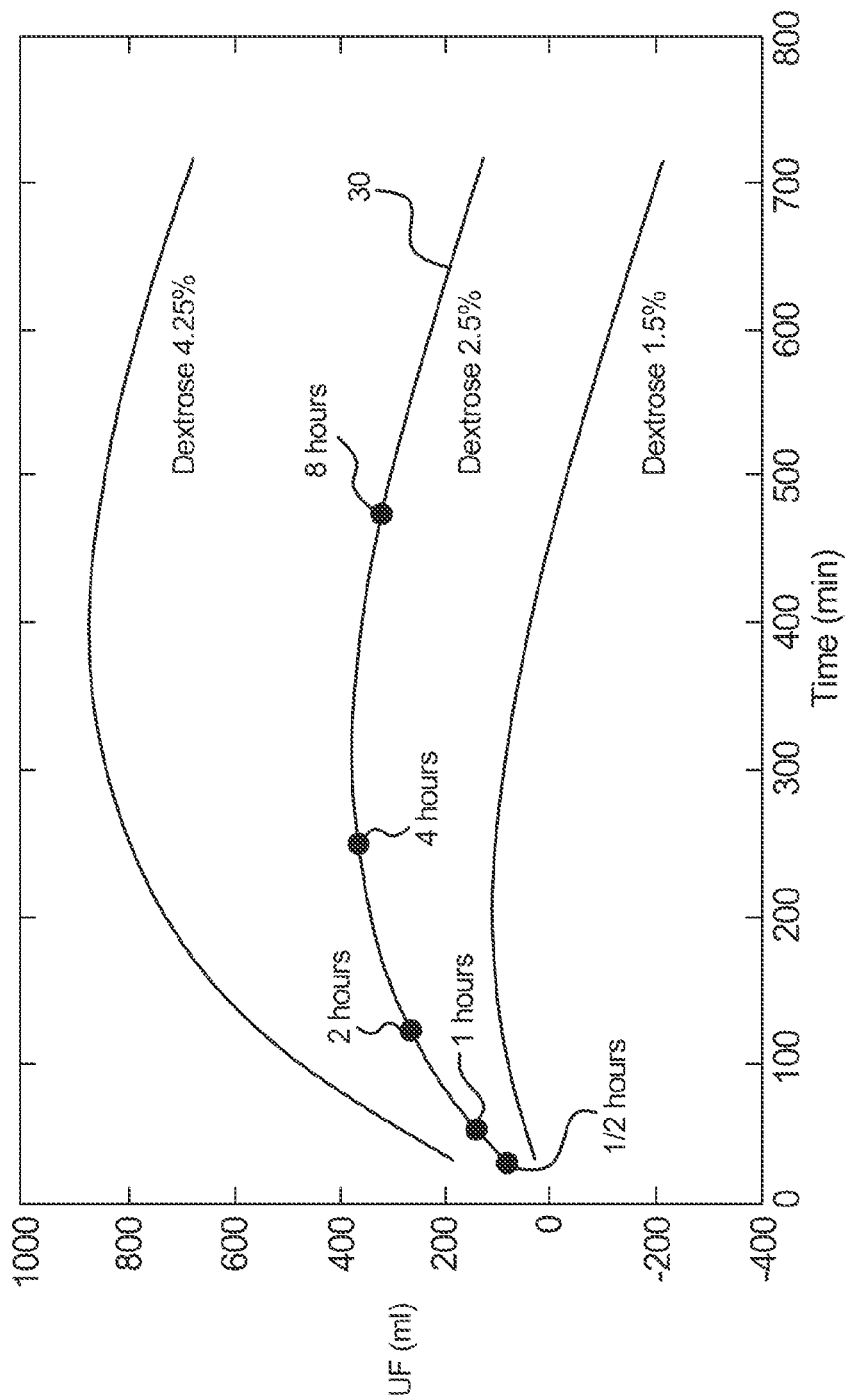

FIG. 4A

PET

Patient Name: BSA: <1.71 PET: High 1
Age: 37    Gender: F

Overnight Exchange
% Dextrose:         2.5
Solution Type:      Dianeal
Volume Infused:     2000 mLs
Volume Drained:     2200 mLs Four Hour Equilibration
% Dextrose:         2.5
Solution Type:      Dianeal
Volume Infused:     2000 mLs
Volume Drained:     2179 mLs Dwell Time:         510 min.
Dialysate Urea:     49 mg/dL
Dialysate Crt:      7.9 mg/dL Infusion Time:      10 min.
Drainage Time:      20 min.

Transport Type:
H
Correction Factor:  0
☑ Typical Values
   Calculate
Fluid Absorption (mL/min):  1.00
Residual Dialysate Volume (mLs):  200.00

PET Details...
Fluid Absorption...
MTAC...

Data
|             | Time | Urea | Creatinine | Glucose | Corrected Crt. | CRT D/P |
|-------------|------|------|------------|---------|----------------|---------|
| Serum #1:   | 120  | 54   | 8.7        | 165     | 8.70           |         |
| Dialysate #1: | 0  | 6    | 1.1        | 2016    | 1.10           | 0.13    |
| Dialysate #2: | 120 | 43  | 6          | 940     | 6.00           | 0.69    |
| Dialysate #3: | 240 | 49.8 | 7.3       | 583     | 7.30           | 0.84    |
|             | min  | mg/dL | mg/dL    | mg/dL   | mg/dL          |         |

✓ OK    ✗ Cancel    ? Help

FIG. 4C

Mass Transfer Area Coefficient

Patient Name: BSA: 1.71  PET: High  1

| Solute: | Starting Concentration (mmol/L) | Generation Rate (mmol/min) | MTAC* (mL/min) | Sieving Coefficient |
|---|---|---|---|---|
| Urea: | 19.24 | 0.104085 | 25.318723 | 0.759 |
| Creatinine: | 0.77 | 0.003077 | 17.654085 | 0.711 |
| Glucose: | 8.05 | 2.013367 | 14.826720 | 0.500 |

*(MTAC = Mass Transfer Area Coefficient)

Water Transport Parameters:

Hydraulic Permeability, LPA (mL/min/mmol/L): 0.501

Fluid Absorption, QL (mL/min): 1.000

Initial Total Body Water, V (Liters): 30.46

24-Hour Fluid Removal (L/day): 0.950

Other Parameters:

Residual Dialsate Volume, VDO (mLs): 301.3

Estimated GFR, KR (mL/min): 0.000

[Close]  [Help]

FIG. 4D

Fluid Absorption Details

Patient Name: BSA <1.71  PET: High  1

PD Rx Management has calculated the fluid absorption of 0.1 mL/min using the drain volumes from the overnight and four hour PET. Please review the overnight and four hour fill and drain volumes for accuracy. Using this calculated value, the following drain volumes would be observed.

––––––––––––––––– Volume Drained –––––––––––––––––

|  | Actual | Predicted | Difference |
|---|---|---|---|
| Overnight Exchange | 2200 | 2184 | 16 |
| Four Hour | 2179 | 2196 | -17 |

Hydraulic permeability: LPA = 0.501 (mL/min)(mmol/L)

Using a typical fluid absorption of: 1.0 mL/min., the following drain volumes would be observed.

––––––––––––––––– Volume Drained –––––––––––––––––

|  | Actual | Predicted | Difference |
|---|---|---|---|
| Overnight Exchange | 2200 | 2080 | 120 |
| Four Hour | 2179 | 2331 | -152 |

Hydraulic permeability: LPA = 1.403 (mL/min)(mmol/L)

Please enter the desired fluid absorption you wish PD Rx Management to use in modeling this patient: 1

✓ OK    ✗ Cancel    ? Help

Custom AutoFilter

Show rows where:
24 hr UF (L)

is greater than or equal to    1.5

● And    ○ Or

Use ? to represent any single character
Use * to represent any series of characters OK    Cancel

FIG. 6C

Custom AutoFilter

Show rows where:
24 hr UF (L)

is greater than or equal to ▼    1.1 ▼

⦿ And   ○ Or is less than or equal to ▼    1.3 ▼

Use ? to represent any single character
Use * to represent any series of characters OK    Cancel

FIG. 7A

| Regimen | Total Volume (L) | Vol Per Exchange | Number of Exchanges | Time (Hours) | % Dextrose | Total Night Volume (L) | Vol Per Exchange (L) | Number of Night Exchanges | Night therapy Time (Hr) | % Dextrose | Urea (L/week) | Creatinine Clearance (L/wk/1.73m2) | Urea Kt/V | 24 hr UF (L) | Glucose Absorbed (kcal) | Steady State Urea (mg/dL) | Steady State Creatinine (mg/dL) | Solution Cost | Solution Weight (lbs) |
|---|---|---|---|---|---|---|---|---|---|---|---|---|---|---|---|---|---|---|---|
| APD | 1.5 | 1.5 | 1 | 16 | 5 | 12 | 2 | 6 | 8 | 1.5 | 67.6 | 61 | 2.22 | 1.61 | 193 | 40.8 | 5.7 | $40 | 31 |
| APD | 1.5 | 1.5 | 1 | 16 | 5 | 12 | 3 | 4 | 8 | 1.5 | 69.1 | 62.5 | 2.27 | 1.62 | 202 | 40.5 | 5.64 | $40 | 31 |
| APD | 1.5 | 1.5 | 1 | 17 | 5 | 12 | 2.4 | 5 | 7 | 2 | 66.1 | 59.5 | 2.17 | 1.9 | 240 | 42 | 5.88 | $40 | 31 |
| APD | 1.5 | 1.5 | 1 | 17 | 5 | 12 | 2.4 | 5 | 8 | 1.5 | 68.4 | 61.9 | 2.25 | 1.61 | 198 | 40.5 | 5.66 | $40 | 31 |
| APD | 1.5 | 1.5 | 1 | 17 | 5 | 12 | 2 | 6 | 7 | 2 | 65.1 | 58.6 | 2.14 | 1.88 | 233 | 42.4 | 5.94 | $40 | 31 |
| APD | 1.5 | 1.5 | 1 | 16 | 5 | 10 | 3 | 4 | 7 | 1.5 | 66.8 | 60.2 | 2.19 | 1.92 | 245 | 41.8 | 5.85 | $40 | 31 |
| APD | 1.5 | 1.5 | 1 | 12 | 5 | 12 | 2 | 5 | 8 | 1.5 | 63.3 | 57.9 | 2.08 | 1.58 | 183 | 44 | 6.07 | $37 | 26 |
| APD | 2 | 2 | 1 | 8 | 5 | 12 | 2 | 6 | 7 | 1.5 | 62.9 | 56.7 | 2.07 | 1.5 | 173 | 43.9 | 6.14 | $40 | 31 |
| APD | 2 | 2 | 1 | 7 | 5 | 12 | 2.4 | 5 | 8 | 1.5 | 70.4 | 63.8 | 2.31 | 1.63 | 196 | 39.4 | 5.49 | $40 | 31 |
| APD | | | | | | 12 | 2.4 | 5 | 8 | 1.5 | 69.7 | 62.9 | 2.29 | 1.57 | 196 | 39.9 | 5.57 | $40 | 31 |

Patient Name: BSA: <1.71 PET: High
Potential Regimen Outcomes
ID Number: 1
Collection Date: 2/1/1996

FIG. 7B

| | A | B | C | D | E | F | G | H | I | J | K | L | M | N | O | P | Q | R | S | T |
|---|---|---|---|---|---|---|---|---|---|---|---|---|---|---|---|---|---|---|---|---|
| | Regimen | Total Volume (L) | Vol Per Exchange | Number of Exchanges | Time (Hours) | % Dextrose | Total Night Volume (L) | Vol Per Exchange (L) | Number of Night Exchanges | Night therapy Time (Hr) | % Dextrose | Urea (L/week) | Creatinine Clearance (L/wk/1.73m2) | Urea Kt/V | 24 hr UF (L) | Glucose Absorbed (kcal) | Steady State Urea (mg/dL) | Steady State Creatinine (mg/dL) | Solution Cost | Solution Weight (lbs) |
| 45 | APD | 1.5 | 1.5 | 1 | 8 | 2.5 | 12 | 2.4 | 5 | 8 | 1.5 | 63 | 56.3 | 2.07 | 1.12 | 322 | 44.2 | 6.24 | $31 | 26 |
| 49 | APD | 1.5 | 1.5 | 1 | 8 | 2.5 | 12 | 2.4 | 5 | 8 | 1.5 | 63 | 56.3 | 2.07 | 1.12 | 322 | 44.2 | 6.24 | $31 | 26 |
| 57 | Tidal | 0 | 0 | 0 | 0 | 0 | 15 | 2.5 | 11 | 9 | 1.7 | 63.8 | 56.7 | 2.09 | 1.15 | 316 | 46.4 | 6.61 | $31 | 33 |
| 58 | Tidal | 0 | 0 | 0 | 0 | 0 | 15 | 2.5 | 11 | 8.5 | 1.7 | 62.3 | 55.2 | 2.05 | 1.11 | 306 | 46.5 | 6.66 | $31 | 33 |

FIG. 8A

High Ultrafiltration

Patient Name: _____ BSA: <1.71  PET_High 1
Rx Date: _____                    ☐ Current Rx

Nighttime
Total Time (Hours): [7]
Total Volume Infused (mLs): [12000]     Note: To determine the
Fill Volume – Per Exchange (mLs): [2000] Home Choice Pro total
Percent Dextrose: [2]                   volume use nighttime
Number of Exchanges: [6]                volume plus first
Dwell Time Per Exchange (min): [40.6]   daytime exchange (and
                                        any additional
                                        exchanges performed
                                        using the cycler).

Daytime
Number of Daytime Exchanges: [1]   ☐ High Dose/OCPD
(0 if a Dry Day)
        Percent        Infused        Period Time
        Dextrose       Volume         (hours)
                       (mLs)
APD Day  [Extraneal ▼]  [1500]        [17]
Exchanges
[1]

[Patient Data...]  [Continue]  [Close]  [? Help]

FIG. 8B

Patient Name: _____
Rx Date: _____
BSA: <1.71    PET __ High 1

Nighttime
Total Time (Hours): 8
Total Volume Infused (mLs): 10000
Fill Volume - Per Exchange (mLs): 2000
Percent Dextrose: 1.5
Number of Exchanges: 5
Dwell Time Per Exchange (min): 66.6

Note. To determine the Home Choice Pro total volume use nighttime volume plus first daytime exchange (and any additional exchange performed using the cycler).

Daytime
Number of Daytime Exchanges: 1
(0 if a Dry Day)
Percent Dextrose: Extraneal
Infused Volume (mLs): 1500

☐ High Dose/OCPD
Period Time (hours): 16

APD Day Exchanges: 1

Standard UF
☐ Current Rx

[Patient Data...] [Continue] [Close] [? Help]

FIG. 8C

Patient Name:   BSA: <1.71   PET_High 1   Low Ultrafiltration
Rx Date: [▼]                                ☐ Current Rx

Nighttime

Total Time (Hours): [8.5]
Total Volume Infused (mLs): [15000]
Fill Volume - initial (mLs): [2500]                    Tide
Percent Dextrose: [1.7]                            (% of fill)
Number of Exchanges: [11]                              [50]

Daytime

Number of Daytime Exchanges: [0 ▲▼]   ☐ High Dose/OCPD
(0 if a Dry Day)

Tidal Day        Percent         Infused      Period Time
Exchanges        Dextrose        Volume         (hours)
   [ ]          [  ▶ ]          (mLs)            [ ]
                                 [ ]

[Patient Data...]  [Continue]  [Close]  [? Help]

FIG. 9A

Filter Generated Regimens

Filter the generated Regimens to identify an optimum Regimen:

| | | |
|---|---|---|
| 0 | <= Urea Kt/V <= | 5.0 |
| 52 | <= Creatinine Clearance (L/wk/1.73m2) <= | 100.0 |
| 1 | <= 24 Hour UF (Liters) <= | 5.0 |
| 0.0 | <= Glucose Absorbed (Kcal/day) <= | 600.0 |
| 7 | <= Night Therapy Time (Hours) <= | 7 |
| 8 | <= Night Total Volume (Liters) <= | 8 |
| 0 | <= Last Fill Volume (Liters) <= | 1 |
| 1.5 | <=Day Fill Volume (Liters)<= | 3 |
| Y | Y / N - Allow Dry Day | |
| Y | Y / N - Allow Last Fill | |
| N | Y / N - Allow Last Fill plus 1 Day Exchange | |
| N | Y / N - Allow Last Fill plus 2 Day Exchanges | |
| N | Y / N - Allow Last Fill plus 3 Day Exchanges | |

[ Filter ]

Filtered Results

Regimens with predicted results that meet the specified generation requirements and filtering criteria:

| | | |
|---|---|---|
| 1.89 | <= Urea Kt/V <= | 2.62 |
| 52.13 | <= Creatinine Clearance (L/wk/1.73m2) <= | 70.85 |
| 1.00 | <= 24 Hour UF (Liters) <= | 1.63 |
| 288.61 | <= Glucose Absorbed (Kcal/day) <= | 599.16 |
| 7.00 | <= Night Therapy Time (Hours) <= | 7.00 |
| 8.00 | <= Night Total Volume (Liters) <= | 8.00 |
| 1.00 | <= Last Fill Volume (Liters) <= | 1.00 |
| 1.50 | <=Day Fill Volume (Liters)<= | 3.00 |
| | Regimens with Dry Day | 0 |
| | Regimens with last Fill plus 0 Day Exchange | 0 |
| | Regimens with last Fill plus 1 Day Exchange | 135 |
| | Regimens with last Fill plus 2 Day Exchanges | 88 |
| | Regimens with last Fill plus 3 Day Exchanges | 0 |

Count of Regimens with predicted results that meet the specified requirements: 223

Parameter [ ▶ ] Minimum [ ] Maximum [ ]

[ Delete Filtered Regimens ]  [ Close ]

Filter Generated Regimens

Filter the generated Regimens to identify an optimum Regimen:

| | | |
|---|---|---|
| 0 | <= Urea Kt/V <= | 5.0 |
| 52 | <= Creatinine Clearance (L/wk/1.73m2) <= | 100.0 |
| 1.25 | <= 24 Hour UF (Liters) <= | 5.0 |
| 0.0 | <= Glucose Absorbed (Kcal/day) <= | 500.0 |
| 7 | <= Night Therapy Time (Hours) <= | 7 |
| 8 | <= Night Total Volume (Liters) <= | 8 |
| 0 | <= Last Fill Volume (Liters) <= | 1 |
| 1.5 | <=Day Fill Volume (Liters)<= | 1.5 |
| Y | Y / N - Allow Dry Day | |
| Y | Y / N - Allow Last Fill | |
| N | Y / N - Allow Last Fill plus 1 Day Exchange | |
| N | Y / N - Allow Last Fill plus 2 Day Exchanges | |
| N | Y / N - Allow Last Fill plus 3 Day Exchanges | |

[Filter]

Filtered Results

Regimens with predicted results that meet the specified generation requirements and filtering criteria:

| | | |
|---|---|---|
| 2.02 | <= Urea Kt/V <= | 2.19 |
| 56.34 | <= Creatinine Clearance (L/wk/1.73m2) <= | 60.25 |
| 1.28 | <= 24 Hour UF (Liters) <= | 1.33 |
| 423.57 | <= Glucose Absorbed (Kcal/day) <= | 473.34 |
| 7.00 | <= Night Therapy Time (Hours) <= | 7.00 |
| 8.00 | <= Night Total Volume (Liters) <= | 8.00 |
| 1.00 | <= Last Fill Volume (Liters) <= | 1.00 |
| 1.50 | <=Day Fill Volume (Liters)<= | 1.50 |
| | Regimens with Dry Day | 0 |
| | Regimens with last Fill plus 0 Day Exchange | 0 |
| | Regimens with last Fill plus 1 Day Exchange | 2 |
| | Regimens with last Fill plus 2 Day Exchanges | 1 |
| | Regimens with last Fill plus 3 Day Exchanges | 0 |

Count of Regimens with predicted results that meet the specified requirements: 3

[Delete Filtered Regimens] [Close]

Parameter [ ▶ ]   Minimum [ ]   Maximum [ ]

```
               1. Standard UF - 8 Hour with Wet Day
1. Dianeal, 1.5% 6-liter                                    2
    Alternate Dianeal, 1.5% 3-liter                         4
2. Extraneal, 2 liter                                                1
               2. High UF - 7 Hour with Wet Day
1. Dianeal, 1.5% 6-liter                                    2
    Alternate Dianeal, 1.5% 3-liter                         4
2. Dianeal, 1.5% 3-liter                                    1
    Alternate Dianeal, 1.5% 6-liter                         1
3. Extraneal, 2 liter                                                1
               3. Low UF - 8-1/2 Hour with Dry Day
1. Dianeal, 1.5% 6-liter                                    2
    Alternate Dianeal, 1.5% 3-liter                         4
2. Dianeal, 2.5% 3-liter                                    1
```

FIG. 11

Patient's Minimum Base Supply Inventory

- Standard UF - 8 Hour with Wet Day         32 Days
- High UF - 7 Hour with Wet Day             6 Days
- Low UF - 8-1/2 Hour with Dry Day          6 Days
- Disposable Set - 4 Prong w/22" Patient Line   45 Sets
- Ultrabag 1.5%, 2-1/2 liter (case of 6)    1 Case
- Flexicaps                                 45 Caps

FIG. 12

```
                Actual Patient in House Inventory

1. Dianeal, 1.5% 6-liter bag (case of 2)              5     5B9710
2. Dianeal, 2.5% 3-liter bag (case of 4)              1     5B5169
3. Extraneal, 2 liter bag    (case of 6)              1     5B4974
4. 4 Prong Set w/22" Patient & Drain Lines (case of 30)  0  5C4531P
      Qty Left in Opened Cases                       24
5. Ultrabag 1.5%, 2-1/2 liter (case of 6)             0     5B9868P
      Qty Left in Opened Cases                        2
6. Flexicap (case of 30)                              1     5C4456
      Qty Left in Opened Cases                        6
```

FIG. 13

| Item Description | Code No. | Item Base Inventory | On Hand | Case Order Amount |
|---|---|---|---|---|
| Dianeal, 1.5% 6-liter bag | 5B9710 | 88 | 10 | 78/2 = 39 |
| Dianeal, 2.5% 3-liter bag | 5B5169 | 6 | 4 | 2/4 = 1 |
| Extraneal, 2-liter bag | 5B4974 | 38 | 6 | 32/6 = 6 |
| 4 Prong Set w/22" Patient & Drain Lines | 5C4531P | 45 | 24 | 21/30 = 1 |
| Ultrabag 1.5%, 2-1/2-liter | 5B9868P | 6 | 2 | 4/6 = 1 |
| Flexicap | 5C4456 | 45 | 36 | 9/36 = 1 |
| | | | | |
| | | | | |

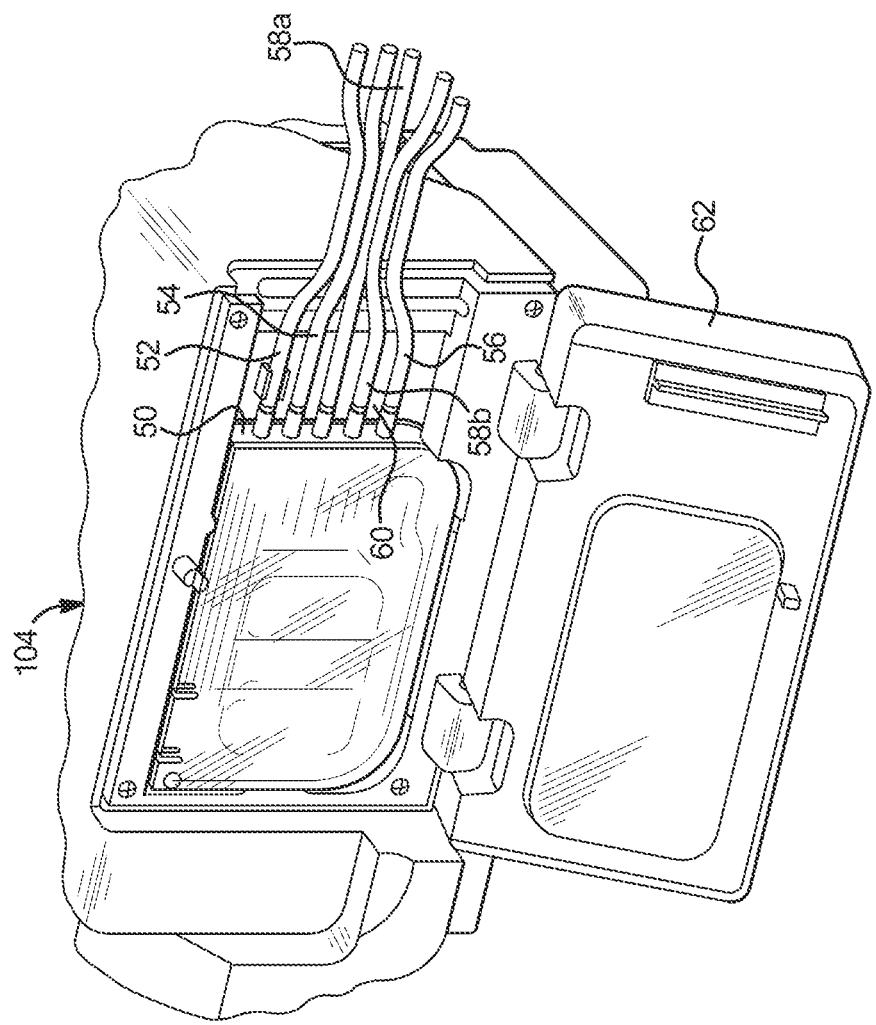

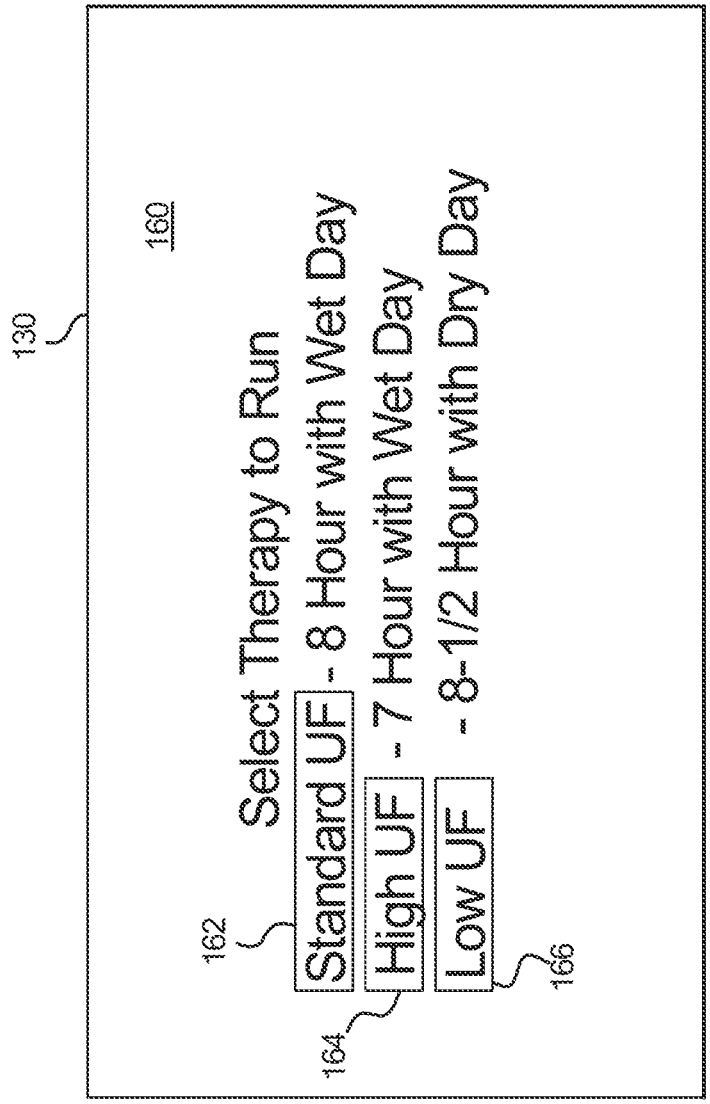

NETWORKED DIALYSIS SYSTEM

PRIORITY CLAIM

This application claims priority to and the benefit as a continuation application of U.S. patent application Ser. No. 13/947,771, entitled "System and Method For Selection of Stored Dialysis Therapy Prescriptions," filed Jul. 22, 2013, issued as U.S. Pat. No. 9,141,760 on Sep. 22, 2015, which in turn claims priority to and the benefit of U.S. patent application Ser. No. 13/563,327, entitled "Dialysis System and Machine Having Therapy Prescription Recall," filed Jul. 31, 2012, issued as U.S. Pat. No. 8,512,554 on Aug. 20, 2013, which in turn claims priority to and the benefit of U.S. patent application Ser. No. 13/251,901, entitled "Dialysis System and Machine Having Therapy Prescription Recall," filed Oct. 3, 2011, issued as U.S. Pat. No. 8,257,582 on Sep. 4, 2012, which in turn claims priority to and the benefit of U.S. patent application Ser. No. 12/170,230, entitled "Dialysis System and Machine Having Therapy Prescription Recall," filed Jul. 9, 2008, issued as U.S. Pat. No. 8,062,513 on Nov. 22, 2011, each of which are incorporated herein by reference in their entireties and for all purposes.

CROSS-REFERENCE TO RELATED APPLICATION

This application is related by subject matter to U.S. patent application Ser. No. 14/012,598, entitled, "Dialysis Treatment Prescription System And Method", filed on the same day as this application.

BACKGROUND

The proportion of patients performing automated peritoneal dialysis ("APD") is increasing worldwide, which is due in part to the ability of APD to be adapted to the patient's particular needs regarding the patient's private life and the patient's therapy needs. The two primary goals of dialysis, solute clearance and ultrafiltration ("UF") depend on the modality or type of APD performed (e.g., nocturnal intermittent peritoneal dialysis ("NIPD"), continuous cycling peritoneal dialysis ("CCPD") and hi-dose CCPD, solution type, therapy time and fill volume. Prescribing an APD therapy constitutes selecting one of each of these. Thus there are many combinations and possibilities from which to choose.

APD devices typically do not have the capability to provide feedback to the patient regarding the effectiveness of his/her recent therapies. Also, APD devices typically run open loop such that they do not adjust therapy parameters (e.g., modality, solution type, therapy time and fill volume) based on the actual measured daily clearance and UF. Accordingly, some patients underachieve their targets and develop adverse conditions such as fluid overload and in some cases hypertension. Current methods for adjusting treatment typically involve the patient reporting to a center every so often to be evaluated. These methods place the burden of therapy adjustment solely on the doctor or clinician and do not occur frequently enough to adjust properly to the patient's weekly, monthly, seasonal or other lifestyle change.

The systems and methods of the present disclosure attempt to remedy the above problems.

SUMMARY

The system of the present disclosure includes a plurality of prescription optimization modules. One of the modules is an advanced peritoneal equilibration test or ("PET"). The PET allows the patient to perform an ultrafiltration ("UF") portion of the PET at home automatically using the patient's automated peritoneal dialysis ("APD") machine. The automated test collects more UF data point samples than in the past, which helps to establish a more accurate UF patient-characteristic curve. The UF samples and blood work are then used to generate physiological data for the patient.

A second module of the prescription optimization system of the present disclosure is to use the above patient physiological data in continuation with specified therapy targets (e.g., UF, clearance) and ranges of therapy inputs (e.g., number of exchanges, cycle times, solution choices) to calculate or deliver all possible regimens that fit within the provided ranges.

A third aspect or module of the present disclosure is to use one or more filter specifying a patient's preference or doctor's performance requirement to narrow the number of regimens to a manageable few. The doctor or patient agree upon a certain number of the regimens, e.g. three to five regimens, to be prescribed by the doctor for treatment.

Another feature of the present disclosure is an inventory tracking module that tracks different solutions and other supplies used over a delivery cycle in performing the different prescriptions selected by the patient. The APD machine has the ability to mix dialysis solutions of different dextrose levels to produce hybrid dextrose dialysate blends, which further enables the patient's treatment to be optimized. The inventory tracking feature records dextrose levels used and replaces the associated dialysate concentrations consumed.

A fifth module of the present disclosure is a trending of the prescriptions that the patients are performing. The trends can track any one or more of UF removed, body weight blood pressure and prescription used. A sixth module controls how the different prescriptions are recalled for use and adjusted or replaced if needed. The trends can also trend and show averages such as a seven day moving average UF and/or a thirty day moving average.

In one embodiment, the patient at the beginning of treatment weighs himself/herself (e.g. after initial drain) and takes the patient's blood pressure. As discussed in detail herein, the present system includes a scale and blood pressure taker that output weight and blood pressure information, respectively, wirelessly to the APD machine using a wireless technology such as Bluetooth™, WiFi™, Zigbee™ technology. The wireless link is provided via radio frequency transmission in one embodiment. In an alternative embodiment, the weight and blood pressure information are provided via a wired connection between the scale and blood pressure taker and the APD machine. The patient alternatively types in the weight and blood data.

The APD machine provides multiple therapy prescriptions from which either the patient or the APD machine chooses one for that day's treatment. For example, the APD machine can provide five physician-approved prescriptions for the patient, one of which is chosen based on the patient's weight, blood pressure and UF removed over the last twenty-four hours. The prescription does not need to be selected before the initial drain (initial drain is done in any of the possible treatments), so that the patient or machine can obtain the final UF information from the previous day's treatment before determining which prescription to select. The machine in one embodiment provides prompts at the beginning of treatment to remind the patient to obtain the patient's weight and blood pressure.

The five possible prescriptions are determined analytically. One possibility is to develop and store an algorithm either in the APD machine itself or in a server computer that communicates with the APD machine, e.g., via an internet connection. The algorithm can employ a three-pore model, for example, which adds predicted clearances across three different sized pores in the patient's peritoneal membrane. Flow of toxins through large pores, small pores and micropores in the blood vessels of the peritoneal membrane are summed Urea and creatinine for example are removed from the patient's blood through the small pores. The large pores allow larger protein molecules to pass from the patient's blood to the dialysate. In each case, an osmotic gradient drives the toxins from the patient's blood to the dialysate. Using the predicted clearances and the three-pore model, the system of the present disclosure outputs a plurality of acceptable regimens for the patient. From these regimens five prescriptions can be selected, for example. The algorithm alternatively uses a two-pool model as discussed in detail below.

In one embodiment, the regimen generation portion of the system is stored and used at a dialysis center or nephrologist's office. The patient enters the office or center, and the doctor or clinician examines the patient, enters patient data into regimen generation software located at the office or center, which outputs suitable regimens from which, e.g., five, different prescriptions are selected. These different prescriptions are expected to address the patient's varying APD needs for the foreseeable future, e.g., over the next six months to a year. New patients may have residual renal function ("RRF"), such that their kidneys are partially functional. These patients do not need treatments that are as aggressive as do patient's with no kidney function. The need for adjustment for these patients may be greater however as RRF degrades. Here, the plurality of prescriptions may need to be upgraded more frequently, e.g., every three months.

The three-pore model is very good at predicting clearance values, such as urea removed, Kt/V, pKt/V, creatinine removed, CCr, pCCr, glucose absorption and total effluent. The system of the present disclosure also uses an advanced peritoneal effectiveness test ("PET") to help predict UF removal accurately. The advanced PET also includes blood samples and chemical analysis performed on dialysate samples to accurately predict the patient's clearances for urea removed, Kt/V, pKt/v, creatinine removed, CCr, pCCr, glucose absorption and total effluent even better.

Regarding the advanced PET module of the present disclosure, the advanced PET includes samples taken over two therapies. In the first therapy, for example, UF is measured after a thirty minute dwell, sixty minute dwell, 120 minute dwell and 240 minute dwell, totaling 7.5 hours. In the second therapy, UF is measured after an eight hour dwell, providing a total of five data points. At each time interval, the patient is drained completely to determine UF accurately. The UF can be measured by the APD machine or alternatively or additionally via a weight scale if more accuracy is desired. Because the patient has to refill after draining completely each time, the actual UF time periods may differ slightly from the intended UF time periods. For example, the two hour UF time period may actually consume two hours and ten minutes. The system of the present invention records the actual time period and uses the actual time as an input to the kinetic modeling.

The blood and dialysate samples can be taken at certain intervals wherever and whenever blood can be drawn. The first and second therapies can be performed consecutively or over two nights. In one embodiment, the patient performs the half hour, one hour, and four hour fills/dwells/drains at night before bed. The patient then performs a last fill, sleeps and is awakened in time to perform the eight hour drain. UF and actual dwell times are recorded for each dwell period. The data can be recorded on a data card that the patient beings the next day to the lab or center. The data is transferred to the lab or center alternatively via an internet using a data communications module discussed herein.

The patient then travels to a dialysis center. The patient is filled an additional time. Blood and dialysate samples are taken at two hours and four hours, for example. A second four-hour drain UF data point can be taken and compared to the first four-hour drain UF data point for additional accuracy.

The five data UF points, blood testing and dialysate testing data are obtained using a particular dialysate concentrate, such as 2.5 percent dextrose. The data points are used to estimate kinetic parameters consisting of solute mass transfer area coefficients ("MTAC") and ultrafiltration parameters (a hydraulic permeability coefficient and a fluid absorption rate) and also to classify the patient's transport and UF characteristics. Based on the estimated kinetic parameters, kinetic modeling using a modified three-pore model can then be applied physiologically to other types of dialysate concentrate, such as 1.5 percent dextrose and Extraneal® dialysate.

Regarding the regimen generation module of the present disclosure, the prediction algorithms use the above calculated patient transport and UF characteristics, target information and other therapy input information to generate the regimens. The target and other therapy information include for example: (i) clinical targets such as (a) minimum urea clearance, (b) minimum urea Kt/V, (c) minimum creatinine clearance, (d) maximum glucose absorption, and (e) target UF; and (ii) therapy parameters such as (a) therapy time, (b) therapy volume, (c) fill volume, (d) percent dextrose, and (e) solution type; and (iii) available solutions. Many of these inputs are expressed in ranges, leading to many possible regimen outcomes. The software using the three-pore or two-pool model equations generates, in one embodiment, every possible regimen using (i) each input in each range and (ii) the patient's transport and UF characteristics, which meets the above-described target and therapy information.

Regarding the prescription filtering module, the system allows the user to specify certain filtering information to pair the regimen combinations down to a manageable number of combinations from which to select and approve as set of prescriptions. The filtering information can include for example filtering out all regimens with aKt/V, creatinine clearance and UF below a certain value, and a glucose absorbed above a certain value. The clinician and patient then agree on a few of the paired down prescription possibilities to be stored as prescriptions on the patient's APD machine or alternatively on a server computer having a communications link to the APD machine.

The prescriptions can be stored on the patient's data card and loaded physically into the APD machine when the patient returns home. Alternatively, a dialysis center downloads the prescriptions to the APD machine via a internet or other data communications network. One set of prescriptions can include for example: (i) a standard UF prescription; (ii) a high UF prescription; and (iii) a low UF prescription. If the patient is capable, the APD system can be set to allow the patient to run a prescription tailored to the day's activities. If the patient exercises heavily on certain days, losing large amounts of body fluids via sweat, the patient can run a lower UF treatment that evening, perhaps saving the patient from having to perform a day exchange the next day. If the patient is out to dinner on a given night and consumes more liquids than normal, the patient can run the high UF treatment. On all other days the patient runs the standard UF prescription.

One corollary component to the instant system is the inventory distribution and tracking module. If the selected prescriptions require different types of dialysate concentrates, the different dialysate types need to be delivered in the right quantity. In the present system, either the APD machine or the clinician's server tracks the patient's current inventory and ensures that a needed supply of the appropriate solutions is delivered to the patient's home.

As discussed herein, one of the therapy parameters is percent dextrose of the solution, which affects the amount of UF removed and the amount of calories absorbed by the patient. More dextrose results in more UF removed, which is generally desirable. More dextrose, however, results in more caloric intake and weight gain by the patient, which is not desirable. Dextrose profiling is therefore an important factor in selecting the patient's possible therapies. The different solutions are provided in different dextrose percentages, such as 1.5%, 2.5% and 4.25% dextrose. The APD machine described in connection with the present system has the ability to connect to multiple solution bags having different glucose percentages and pull solution from the different bags to form a mixed or blended solution, e.g., in a warmer bag or in the patient's peritoneum if inline heating is used, having a desired glucose percentage different from the rated percentages, e.g., 2.0%, 2.88%, 3.38% and 3.81% dextrose. If mixed in a warmer bag, the warmer bag can be fitted with one or more conductive strip, which allows a temperature compensated conductivity reading of the mixed solution to be taken to ensure that the solutions have been mixed properly.

In one embodiment, the APD machine tracks the different bags used during treatment over the course of a delivery cycle. Before the delivery person arrives with new solution bags, the inventory used is sent to the solution distribution facility. This inventory is subtracted from the patient's total home inventory, so that the solution distribution facility knows how much of which solution(s) to deliver to the patient's home. In one embodiment, when the delivery person arrives at the patient's home, the delivery person scans in the patient's remaining inventory for comparison with what is expected to be remaining. The APD machine does not automatically account for solution bags that are destroyed, lost or otherwise not used for treatment. It is contemplated however to allow the patient to enter a lost or destroyed bag amount (or actual total amount of bags remaining) into the APD machine tracking system if such procedure is found to provide more accurate advance inventory information. The delivery person's scan of the remaining product in any case resets the patient's inventory at each delivery so that errors do not accumulate.

Regarding the trending and alert generation module, the APD system of the present disclosure tracks or trends certain therapy parameters, such as daily UF, blood pressure and body weight. The trends in one embodiment can be seen on the display device of the APD machine between therapies, for example at the beginning of a therapy. The trends can also be viewed by the clinician and/or doctor. The patient at the beginning of therapy can for example view the patient's weight, blood pressure and UF removed over the last twenty-four hours. The patient can learn of a previous day's UF after the patient's initial drain, which is from the last fill of the previous night's therapy. That is, the end of a first initial drain to the end of a second initial drain sets a UF cycle that is recorded. The patient after the initial drain weighs himself/herself, providing data that is entered into the machine via cable or wirelessly or, alternatively, via patient entry. The trend data in combination with a set of filters or criterion are used to either allow treatment to be performed under a current set of prescriptions or to be run via a new prescription(s). The machine in one embodiment automatically alerts the clinician if an alarm condition occurs or if a prescription change is needed.

The trend screens can show for example a daily UF trend, a seven day moving average trend and a thirty day moving average trend. The moving average trends smooth the daily highs and lows and more readily indicate UF up and down trends. When the actual UF removed falls below a low threshold UF removed, e.g., over a predefined period of time, or in combination with the patient running a high UF prescription to avoid underperforming UF, the system of the present disclosure causes the APD machine to send an alarm or alert signal to the dialysis center and/or doctor. Different methods or algorithms are discussed herein for preventing the system from overreaction or being too sensitive. Besides the rolling UF averages, the system also uses algorithms that accumulate error and look for other physiological patient parameters, such as weight and blood pressure in an attempt to view the patient more generally instead of just looking at UF removal.

Regarding the prescription recall and adjustment module, the clinician or doctor responds to the prescription alarm in an appropriate manner, such as by calling the patient into the clinic, making suggestions via phone or email regarding the use of the currently existing prescriptions, ordering a new PET, and/or changing the patient's prescriptions. The system is thus configured to remove the burden of detecting a poor performing prescription(s) from the clinician or doctor and to alert of such poor performing prescription as soon as reasonably possible without overreacting to one or more underachieving day.

If an alert condition occurs and the APD machine is not able to communicate the alert condition to the clinic or center, e.g., no internet service is available or accessible, the system is configured to have the APD machine prompt the patient to contact the clinic or center. To that end, the system includes a handshaking procedure in which the clinician's server sends an electronic receipt-confirmed message to the APD machine, so that the APD knows that the alert has been received.

The APD system can be set to respond in a closed-loop manner to a consistent underperforming therapy. Here the APD machine stores a database of acceptable prescriptions, e.g., the five prescriptions prescribed above by the doctor. The machine automatically selects a prescription approved by the doctor in an attempt to improve results. For example, the machine could select a higher UF prescription if the patient's UF has been underperforming. Or, the machine presents a number of prescription options to the patient, who selects one or more prescription approval by the doctor. It should be appreciated that in one embodiment, the system only allows the patient to run a prescription approved by a doctor.

In another alternative embodiment, the plurality of, e.g., five, approved prescriptions are loaded onto the patient's APD machine but only a subset, e.g., three of five, prescriptions is enabled. When the enabled treatments are found to be underperforming, a doctor or clinician enables a previously non-enabled therapy that is, for example, capable of increasing the patient's UF. In this way, the doctor or clinician can select from a pre-approved set of prescriptions and not have to rerun the regimen generation and prescription filtering prescription sequence described above. The system can also provide the above-described alert responses for blood pressure and body weight alert conditions.

The system can respond to alerts in other ways besides changing the patient's prescription. The trends show which prescriptions have been run on which days, so the doctor or clinician can look to see if the patient is running enough therapies and/or the right therapies. The trends also show patient weight, allowing the doctor or clinician to recommend that the patient reduce his/her food and drink intake if the patient has gained too much weight. Patient blood pressure can also be trended and considered upon an alert. Discussed herein are a plurality of algorithms and examples illustrating possible repercussions from a patient alert.

When the patient's therapy is functioning properly, the system can operate to allow the patient to select a prescription to run on a given day. The machine or system can alternatively select the daily prescriptions to run, or some combination thereof. Discussed herein are a number of prescription adjustment algorithms or methods that attempt to balance patient flexibility and lifestyle concerns with therapy performance concerns.

It is accordingly an advantage of the present disclosure to provide an APD system that analyzes patient treatment data and communicates results to the doctor or clinician, who can then spend more time talking to the patient rather than performing the analysis manually.

It is another advantage of the present disclosure to provide a peritoneal dialysis system that attempts to optimize a therapy prescription for the patient.

Still further, it is an advantage of the system of the present disclosure to track or trend various patient PD physiological parameters, to provide rolling averages of same, and to react quickly but not overreact to an apparent underperforming therapy.

It is a further advantage of the system of the present disclosure to provide a closed-loop PD system that responds to underperforming UF, patient weight gain and/or high blood pressure.

It is yet another advantage of the system of the present disclosure to provide a system that tracks patient solution use to deliver multiple needed solutions to the patient efficiently.

It is still a further advantage of the system of the present disclosure to provide a dialysis system that mixes standard dextrose solutions to achieve a desired, blended dextrose level dialysate.

It is yet a further advantage of the system of the present disclosure to provide a dialysis system having a plurality of approved prescriptions from which the patient can choose to fit a patient's daily needs.

It is still another advantage of the system of the present disclosure to provide a dialysis system that uses a more accurate peritoneal equilibration test.

Additional features and advantages are described herein, and will be apparent from, the following Detailed Description and the figures.

BRIEF DESCRIPTION OF THE FIGURES

FIG. 1 is a schematic view of one embodiment of the prescription optimization system of the present disclosure including an improved peritoneal equilibration test ("PET") module, regimen generation module, prescription filtering and selection module, dialysis fluid inventory management module, communications module, data input module, trending and alert generation module, and a prescription recall and adjustment module.

FIG. 2A is a perspective view of a peritoneal blood vessel showing the different sizes of pores used in a three-pore model for predicting peritoneal dialysis therapy results.

FIG. 3 illustrates a sample plot of UF removed versus dwell time from data collected by the dialysis instrument at home for use with an improved peritoneal equilibration test ("PET") of the present disclosure.

FIGS. 4A to 4D are sample screens displayed on a clinician's or doctor's computer as part of the system of the present disclosure, illustrating additional data associated with the improved PET module.

FIG. 5 is a sample screen displayed on a clinician's or doctor's computer as part of the system of the present disclosure, illustrating data associated with the regimen generation module.

FIGS. 6A to 6C are sample screens displayed on a clinician's or doctor's computer as part of the system of the present disclosure, illustrating filtering criteria used to filter the generated regimens into possible prescriptions for therapy.

FIGS. 7A and 7B are sample screens displayed on a clinician's or doctor's computer as part of the system of the present disclosure, illustrating the selection of prescriptions from the list of filtered regimens.

FIGS. 8A to 8C are sample screens displayed on a clinician's or doctor's computer as part of the system of the present disclosure, illustrating the agreed upon high UF, standard UF and low UF prescriptions, respectively.

FIGS. 9A to 9E illustrate another example of a filtering process according to the present disclosure, which results in a final filter of three prescribed regimes for the patient.

FIGS. 10 to 13 are sample screens displayed on a clinician's or doctor's computer as part of the system of the present disclosure, illustrating one embodiment of an inventory management module.

FIG. 14 is a perspective view of one embodiment of a dialysis instrument and disposable pumping cassette illustrating one suitable apparatus for performing dextrose mixing used with the prescription optimization system of the present disclosure.

FIG. 29 is a sample screen displayed on a patient's dialysis instrument illustrating one possible prescription recall embodiment of the prescription recall and adjustment module of the prescription optimization system of the present disclosure.

DETAILED DESCRIPTION

Figure 2B:
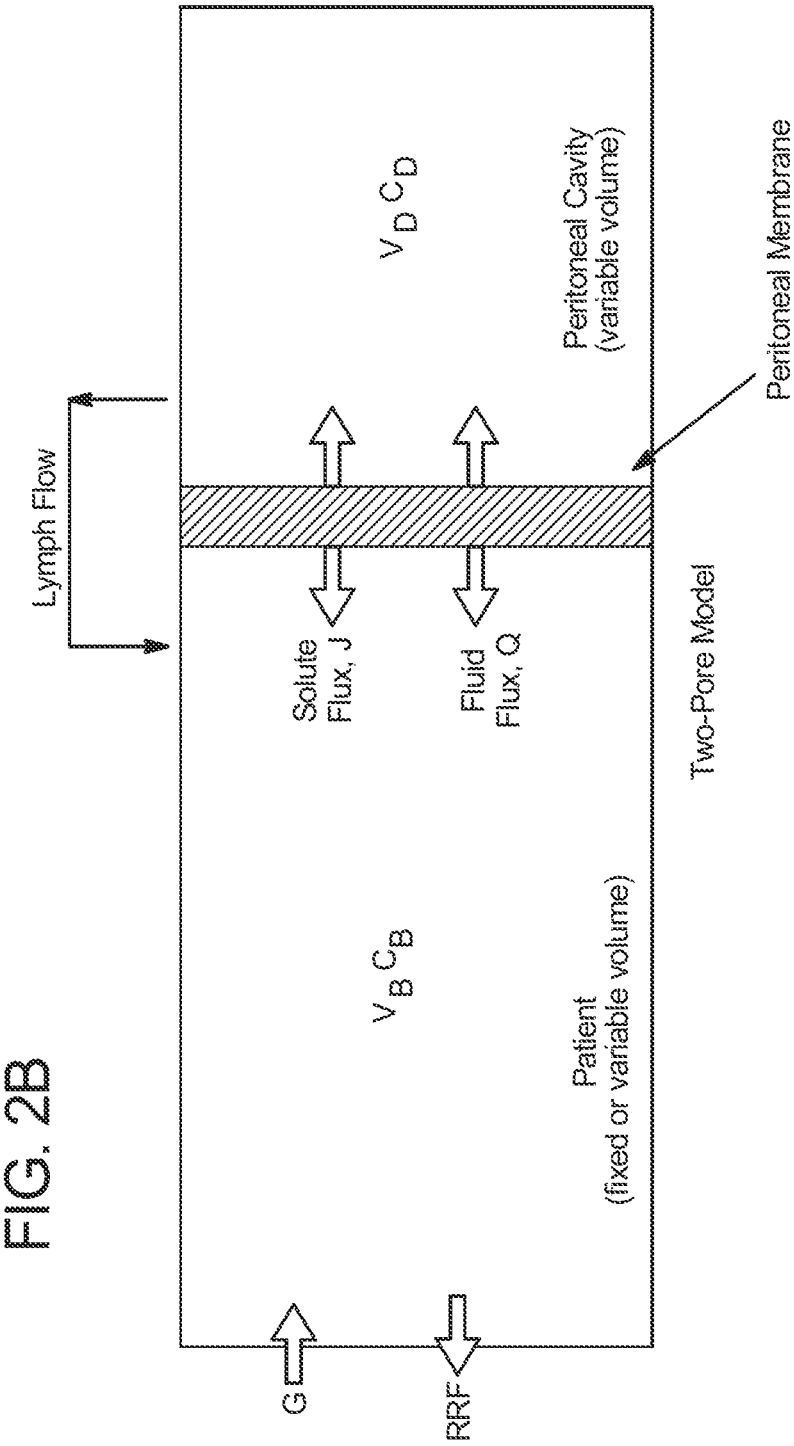
FIG. 2B is a schematic view of the kinetic transport properties of a two-pool model used for predicting peritoneal dialysis therapy results.

Referring now to the drawings and in particular to FIG. 1, a schematic view of peritoneal dialysis ("PD") system 10 having an automated peritoneal dialysis ("APD") machine 104 is illustrated. System 10 provides and uses an improved peritoneal equilibration test ("PET") 12, which samples and employs multiple data points for determining the patient's ultrafiltration ("UF") curve over the course of treatment. PET 12 improves UF prediction used to characterize an individual's response to PD therapies and helps the clinician to generate optimized prescriptions for patients. In one embodiment, PET 12 is performed as a fixed therapy using the APD machine 104 at home. PET 12 also requires lab testing and analysis as set forth below.

System 10 also performs automated regimen generation 14. Known regimen generation is performed manually by a physician 110 or clinician 120 using a hit or miss type strategy, which is time consuming and relies on scientific guessing by the nurse or physician. Automated regimen generation feature 14 uses the results of PET 12, therapy input parameters and inputted therapy target parameters to generate regimens for the physician 110 or clinician 120, which saves time and increases the likelihood that one or more regimen is generated that meets the therapy targets for clearance and UF, minimizes glucose exposure, and meets lifestyle needs.

System 10 further includes a prescription filtering module 16, which reduces the many regimens generated by automated regimen generation feature 14 to a manageable number of prescriptions, which are then selected by the patient and doctor/clinician to provide a set of approved prescriptions that are loaded onto the patient's APD machine 104 at home. In one embodiment, the APD machine 104 supports up to five prescriptions that are transferred to the APD machine 104 via a data card, the internet or other type of data communication. The different prescriptions can include for example: two primary (or standard) prescriptions, one volume depleted (low UF) prescription, and two fluid overloaded (high UF) prescriptions, totaling five. Not all of the prescriptions have to be enabled by the physician. However, once enabled by physician, the multiple prescriptions provide flexibility to the patient and allow the APD machine 104 and therapy to better fit the patient's life style needs, while providing a proper therapy.

Prescription filtering 16 naturally leads to an inventory tracking feature or module 18. Different prescriptions can require the patient to store different types of PD solutions at home. For example, one type of solution may be used for nighttime exchanges, while a second type of solution is used for a last fill or day exchange. Also, the same type of solution can be provided in different dextrose quantities. System 10 determines what types and varieties of type of solutions are needed, quantities of such types and varieties, and what related disposable components are needed to carry out the enabled prescriptions. The APD machine 104 tracks how many of which type and variety of solutions are used over the course of a delivery cycle and communicates the usage to the clinician's server. The clinician's server then determines how much of which supplies need to be delivered to the patient for the next delivery cycle. When the delivery person arrives at the patient's house, he or she can scan the patient's actual remaining inventory to compare against the clinician server's expected remaining inventory. The patient's delivery can be adjusted if needed. Here, the patient's post delivery inventory is known and sent to the clinician's server. Communication is performed using a communications module discussed below.

System 10 as mentioned includes a prescription download and therapy data upload communications module 20 that transfers data between the APD software and doctor/clinician's software, e.g., via any one or more of the internet, modem and cell phone. The dialysis center could use communications module 20 for example to send updated prescriptions to the patient's APD machine. Therapy data, logs and trending data can be uploaded to the doctor/clinician's data center, so that the physician or clinician can access patient information at any time and from anywhere.

System 10 also includes an automated, e.g., twenty-four hour UF, blood pressure and body weight data collection feature 22. The APD machine determines patient twenty-four hour UF, and obtains blood pressure and body weight daily and automatically in one embodiment. A remote exchange system ("RES") collects the patient's mid-day exchange data and feeds such data to the APD machine daily, e.g., via bluetooth or other wireless communication. Blood pressure and body weight devices can also communicate the patient's blood pressure and body weight to the APD machine, e.g., daily and wirelessly. Data collection feature 22 also includes the collection and input of therapy ranges and target information, e.g., into regimen generation feature 14.

System 10 further includes a trending and alert generation feature 24. The APD machine provides, for example, up to ninety days of trending of twenty-four hour UF, blood pressure, heart rate, body weight and prescription used. The patient, clinician and/or doctor can view these curves on the display of the APD machine, clinician computer or doctor's computer. The APD machine obtains the data necessary for the trends, sends the data to a server computer, which in turn generates and monitors the trends. The APD machine and/or clinical software monitors the patient therapy trending data and generates alerts when any of the vital parameters falls outside a physician's preset range (or outside of the range in combination with other alert filtering criteria described herein).

System 10 further includes a prescription recall and modification feature 26. Based on the data the from trend feature 24, patient 102, doctor 110 and/or dialysis center 120 may recall one approved prescription for daily use over another. For example, if the patient's UF results for the past few days have been less than expected, the patient 102, doctor 110 and/or dialysis center 120 may decide to use a higher UF prescription as opposed to a standard UF prescription. System 10 for example can store three or five different prescriptions, which have all been doctor approved. The five prescriptions may include, for example, (i) low UF, (ii) standard UF with shorter duration and higher dextrose, (iii) standard UF with longer duration and lower dextrose, (iv) high UF with shorter duration and higher dextrose, and (v) high UF with longer duration and lower dextrose.

If the patient 102, doctor 110 and/or dialysis center 120 knows that the patient has gained weight of late, a lower dextrose prescription may be selected to reduce the caloric input from the treatment. Otherwise the patient may wish to run a shorter therapy or one without a mid-day exchange for life style reasons. System 10 can be configured such that the patient chooses which prescription to run on a given day. Alternatively, the dialysis instrument 104 runs a prescription downloaded from the dialysis center 120. Further alternatively, the dialysis instrument 104 runs a prescription downloaded from the doctor 110. System 10 can run a hybrid control, which for example allows the patient to choose which prescription to run on a given day as long as the patient is making responsible choices, and if the patient does not make responsible choices, system 10 switches so that the prescription to run is set by the machine for the patient. Alternatively, if the patient does not make responsible choices, system 10 can, e.g., remove less aggressive options from the list of possible prescriptions but still allow the patient to choose from the remaining prescriptions.

Many PD patients lose residual renal function ("RRF") over time, so that the PD therapy needs to remove more UF. Also, the patient's transport characteristics may diminish due to a loss of RRF. When trending function 24 indicates that the patient's UF is underperforming no matter which prescription the patient runs, the patient is gaining too much weight, the patient's blood pressure is too high, or a combination of these conditions occurs, system 10 according to module 26 will automatically alert that the patient's prescriptions likely need to be modified. Discussed herein are a number of measures taken so that system 10 is not oversensitive and allows for natural fluctuations in patient UF, due for example to instrument error and residual volume of fluid left in the patient's peritoneum. However, when the patient shows a pattern of underperformance sufficient to indicate that it is not a result of normal fluctuation, system 10 institutes a number of procedures to improve the patient's PD performance. For example, system 10 can call for a new PET to be performed, new regimens to be generated accordingly, and new prescriptions to be filtered from the regimens generated. Or, perhaps as an initial attempt, system 10 calls for a new set of filtering criteria (e.g., more stringent therapy criteria) to be applied to the previously generated regimens to filter out a new set of prescriptions. The new prescriptions are downloaded to the patient's dialysis instrument 104 via either a data memory card or via an internet link from the doctor's office 110 or the dialysis clinic 120.

Peritoneal Equilibration Test ("PET")

Referring now to FIG. 2A, a cross-section from a peritoneal blood vessel illustrates the three-pores of the vessel. The three-pores each have their own toxin and UF clearance, leading to one kinetic model called the three-pore model. The three-pore model is a mathematical model that describes, correlates and predicts relationships among the time-course of solution removal, fluid transfer, treatment variables and physiological properties. The three-pore model is a predictive model that can be used for different types of dialysate, such as Dianeal®, Physioneal®, Nutrineal®, and Extraneal® dialysates marketed by the assignee of the present disclosure.

The three-pore model is based on an algorithm, which is described as follows:

$$\frac{dV_D}{dt} = J_{V_C} + J_{V_S} + J_{V_L} - L$$

in which:

$V_D$ is the peritoneal fluid volume;

$J_{VC}$ is the flow of fluid through transcellular pores or aquaporins shown in FIG. 2A;

$J_{VS}$ is the flow of fluid through small pores shown in FIG. 2A;

$J_{VL}$ is the flow of fluid through large pores shown in FIG. 2A; and

L is the peritoneal lymph flow.

Research has shown the three-pore model and a modified two-pool model are essentially equivalent in terms of UF and small solute clearance. The modified two-pool model is easier to implement than the three-pore model because it requires less computation, and thus less computer time. Research also has shown that the correlation between predicted results derived from the prediction software versus actual results measured from actual therapies have, for the most part, good correlation. Table 1 below shows results of one study (E. Vonesh et al., 1999). Correlations (rc) are accurate for urea removed, weekly urea clearance (pKt/V), total urea clearance (Kt/V), creatinine removed, weekly creatinnine clearance (pCCr), total creatinine clearance (CCr), glucose absorption and total effluent (drain volume). The UF correlation however is not as accurate due possibly to: APD device UF volumetric accuracy, residual solution volume in the patient, variation of patient's transport characteristics, and limited input points for estimating key kinetic parameters.

TABLE 1

Correlation Between Kinetic Software Model And Actual Measured Results

| | Three-Pore Model (PD Adequest 20 with APD, n = 63) | | | | |
|---|---|---|---|---|---|
| | Measured | | Predicted | | |
| Outcome measure | Mean | SD | Mean | SD | $r_c$ |
| Urea removed (g/day) | 5.33 | 1.86 | 5.35 | 1.88 | 0.93 |
| Kt/V | 2.25 | 0.44 | 2.23 | 0.49 | 0.83 |
| pKt/V | 1.93 | 0.56 | 1.94 | 0.59 | 0.89 |
| Creatinine removed (g/day) | 0.72 | 0.31 | 0.72 | 0.31 | 0.93 |
| CCr (L/week/1.73 m2) | 62.89 | 16.11 | 61.64 | 16.26 | 0.87 |
| pCCr (L/week/1.73 m2) | 47.38 | 15.56 | 47.32 | 15.03 | 0.86 |
| Glucose absorption (g/day) | 103.1 | 61.57 | 105.9 | 54.05 | 0.9 |
| Total effluent (L/day) | 14.47 | 4.83 | 14.57 | 0.509 | 0.98 |
| Net ultrafiltration (L/day) | 0.983 | 0.672 | 1.09 | 0.784 | 0.23 |

It has been found that the certain APD devices can measure fill and drain fluid volumes very accurately. For example, the HomeChoice®/HomeChoicePRO® APD machine provided by the assignee of the present disclosure has a reported total fill and drain volume accuracy of 1% or +/−10 mL. An APD machine employing multiple exchange cycles increases the data points needed to estimate key kinetic parameters, and at the same time, reduces the possibility of introducing errors due to the residual solution volume in the patient. A new PET is accordingly proposed to improve the UF prediction accuracy, while maintaining or improving the current good prediction of small solutes (or toxins).

FIG. 2B illustrates an alternative (two-pool PD) kinetic model that system 10 can use for PET 12. The two-pool PD kinetic model of FIG. 2B, like that of FIG. 2A, is used to predict fluid and solute removal in PD to: (i) aid clinicians in the care and management of patients; (ii) assist clinicians in the understanding of the physiological mechanisms that govern peritoneal transport; and (iii) simulate a therapy outcome. A set of differential equations that collectively describe both diffusive and convective mass transport in both the body and dialysate compartments for an "equivalent" membrane core are as follows:

Body Compartment $$d(V_B C_B)/dt = g - K_{PA}(C_B - C_D) - Q_U s \overline{C} - K_R C_B$$

Dialysate Compartment $$d(V_D C_D)/dt = K_{PA}(C_B - C_D) + Q_U s \overline{C}$$

The diffusive mass transfer rate is the product of the mass transfer area coefficient, $K_{PA}$, and the concentrate gradient, ($C_B - C_D$). $K_{PA}$ is in turn equal to the product of the solute membrane permeability (p) and transfer area (A). The convective mass transfer rate is the product of the net water removal (UF) rate, $Q_U$, the solute sieving coefficient, s, and the mean membrane solute concentration, $\overline{C}$. $K_R$ is the renal residual function coefficient.

Using an approximation to the above equations, an analytical solution was obtained for the ultrafiltration rate, $Q_U$, which in turn was solved analytically for the dialysis volume, $V_D$, at time t as follows:

Dialysate Volume $$V_D = V_D^1 \left\{ 1 + 1.5 \, L_{PA}' \sum_{i=1}^{m} K_i^{*-1}(1 - s_i)(C_{D,i}^1 - C_{B,i}^1)\left(e^{-K_i^* t/V_D^1}\right) \right\}^{2/3} e^{-Q_L^0 t/V_D^1}$$

in which (i) $V_D^1$ is the dialysate volume immediately after infusion (mL); (ii) $L_{PA}'$ is the hydraulic permeability transport rate (mL/min/mmol/L); (iii) $K_i^*$ is the ith solute's value of mass transfer area coefficient (mL/min) minus $1.5 Q_L^0$; (iv) $s_i$ is the ith solute's sieving coefficient; (v) $C_{D,i}^1$ is the ith solutes dialysate concentration immediately after infusion (mmol/L); (vi) $C_{B,i}^1$ is the ith solutes blood concentration immediately after infusion (mmol/L); (vii) t is the time (min); and (viii) $Q_L^0$ is the lymphatic absorption (ml/min) UF can accordingly be calculated from the above equation knowing infusion volume, solution concentration and dwell time. The above equations were all based initially on the Pyle-Popvich two-pool model (Vonesh et al., 1991) and were later modified by Vonesh et al. (1999) to incorporate key aspects of the three-pore model resulting in a modified two-pool model which is also referred to as a modified three-pore model (Vonesh et al., 1999). All subsequent references to a two-pool model or three-pore model refer to the modified model described by Vonesh et al. (1999).

To estimate hydraulic permeability ($L_{PA}$, mL/min/mmol/L) and lymphatic flow rate, ($Q_L$, mL/min) for the modified version of the above equation, two $V_D$ values at corresponding dwell time t1, and t2 are needed. The $V_D$ (fill volume+ UF) value is difficult to measure due to the incomplete drain (cycler) and resulting UF measurement errors. PET 12 as shown in FIG. 3 uses multiple, e.g., five, dwell volume ($V_D$) measurements at multiple (five) different corresponding dwell times, e.g., overnight, four-hour, two-hour, one-hour and half-hour, to improve the accuracy of $L_{PA}$ and $Q_L$ estimation and thus improve the UF prediction accuracy.

In one embodiment, the PET 12 of the present disclosure begins with a UF versus dwell time evaluation performed over the course of two treatments (e.g., two evenings or back to back) by directly estimating the patient's fluid transport parameters and correlating the measured parameters with other PET results. UF removed for a particular type of dialysate is measured by filling the patient with fresh dialysate, allowing the solution to dwell within the patient's peritoneum for a prescribed time, draining the patient, and subtracting the fill volume from the drain volume to determine a UF volume for that particular dwell time.

In one implementation, on a first night, using a standard dialysate, such as a 2.5% dextrose Dianeal® dialysate, the APD machine runs four separate two liter fill/drain cycles: a first cycle at a thirty minute dwell; second cycle at a sixty minute (one hour) dwell; third cycle at a 120 minute (two hour) dwell; and a fourth cycle at a 240 minute (four hour) dwell. Total of all dwell times is about seven hours, thirty minutes, which including the time needed for filling and draining consumes about a typical nine and one-half hour total therapy time. The APD machine records fill volume, drain volume and actual dwell time for each cycle. The fill volume may be slightly less or more than two liters depending for example on how much fresh dialysate is actually existing initially in the bag and how empty the APD machine is able to make the bag. In any case, the fill and drain volumes are recorded accurately so that the resulting calculated UF is also accurate.

In an alternative embodiment, to increase accuracy the patient weighs the dialysate bag before fill and after drain. The weight values can be sent wirelessly from the scale to the APD machine (as discussed in detail below). The patient alternatively enters weight data manually. The APD machine subtracts the pre-fill weight from the post-drain weight to accurately determine a UF value, which is matched with the actual dwell time.

The dwell time can be: (i) the time between the end of a fill and the beginning of the corresponding drain; (ii) the time between the beginning of a fill and the end of the corresponding drain; and (iii) in one preferred embodiment the time between the end of a fill and the end of the corresponding drain. In any of the scenarios, the actual dwell time will likely be slightly more or less than the prescribed dwell time. For example, in scenarios (ii) and (iii), a kinked line during drain will lengthen drain time and thus recorded dwell time. In scenario (ii) a kinked line during fill will lengthen fill time and thus recorded dwell time. The APD machine records the actual dwell times for use as shown below. The actual, not the prescribed times, are used so that any difference between actual and prescribed dwell times does not introduce error into the UF predictive model.

On the next or second night, using the standard (e.g., 2.5% dextrose Dianeal®) dialysate, the APD machine patient runs a single fill volume with a 480 minute or eight hour dwell. The APD machine records actual dwell time (according to any of the scenarios (i) to (iii) above) and matches the actual dwell time with the actual UF recorded (e.g., via the APD or weigh scale) in the APD machine.

At the end of two days, the APD machine has recorded five UF/dwell time data points (more or less data points could be achieved, however, the above five dwell times are acceptable and achievable over two standard eight hour therapies). In one embodiment, the APD machine sends the UF/dwell time data points to a server computer located at a dialysis clinic 120 or doctor's office 110 (FIGS. 15A, 15B, 16A and 16B) at which the remainder of the PET 12 is performed. Various embodiments for linking the APD machine to a server computer are shown herein, for example, an electronic mail link can be used to transport data. In another embodiment, the APD machine records the five (or other number) data points onto a patient data card that the patient inserts into the APD machine. The patient then brings the data card and accompanying data to the dialysis center 120 or doctor's office 110 to complete PET 12.

The patient then travels to the dialysis center or doctor's office, e.g., the next day. The patient is filled an additional time and drained typically after four hours. Blood and dialysate samples are taken for example at two hours and four hours. A second four-hour dwell UF data point can be taken and compared to the first four-hour dwell UF data point for additional accuracy. Alternatively, the second blood sample is taken at four hours but the patient is drained at, e.g., five hours, providing an additional UF dwell data point.

FIG. 3 illustrates a plot of the UF data points for the different actual dwell times. The server computer, or other clinical software computer is programmed to fit a curve 30 to the five data points. Curve 30 fills the gaps between the different recorded dwell periods (e.g., at 0.5 hour, one hour, two hours, four hours and eight hours) and thus predicts the UF that will be removed for any dwell period within the eight hour range and beyond, and for the particular dialysate and dextrose level used.

The osmotic gradient created by the dextrose in the dialysis solution decreases with time as dextrose is absorbed by the body. The patient's ultrafiltration rate accordingly begins at a high level and decreases over time to a point at which the rate actually becomes negative, such that the patient's body begins to reabsorb fluid. Thus UF volume as shown in the graph can actually decrease after a certain dwell time. One of the goals of the present disclosure is to learn the patient's optimal UF dwell time, which may be dextrose level dependent, and incorporate the optimal dwell time(s) into the prescriptions discussed in detail below.

In the illustrated embodiment, curve 30 predicts UF removed for 2.5 percent dextrose. Once the curve is fitted for a particular patient, the curve can then be calculated using the kinetic model to predict UF/dwell time values for other dialysates and other dextrose levels, e.g., for 1.5 percent and 4.25 percent dextrose levels. As shown in FIG. 3, for 2.5 percent dextrose, curve 30 has a maximum UF removed dwell time of about three hundred minutes or five hours. Five hours is likely too long a dwell time, however, UF for a dwell time of two hours or 2.5 hours comes fairly close to the maximum UF dwell time. A dwell time of two hours comes much closer to the maximum for 1.5 percent dextrose. 4.25 percent dextrose lends itself to longer dwells as seen in FIG. 3. For example, a single day exchange is a good application for 4.25 percent dextrose.

Besides predicting optimal UF, the five or six UF data points, blood testing and dialysate testing data are taken using a particular dialysate, such as 2.5 percent dextrose Dianeal® dialysate. Each of the UF, blood and dialysate the data are used to generate mass transfer area coefficient ("MTAC") data and hydraulic permeability data to classify the patient's transport and UF characteristics. The MTAC data and hydraulic permeability data can then also be applied physiologically to other types of dialysates, such as 1.5 or 4.5 percent dextrose solutions and for different formulations, such as Extraneal® and Nutrineal® dialysates provided by the assignee of the present disclosure. That is, curve 30 is shown for one concentration. However, once the kinetic model and $L_{PA}$ and $Q_L$ (from PET test results) are known, system 10 could calculate the $V_D$ according to the algorithm above, for each the solution type, dextrose concentration, dwell time, and fill volume. An $L_{PA}$ value of 1.0 (mL/min/mmol/L) and a $Q_L$ value of 0.8 ml/min were used in the simulation for curve 30 (2.5% dextrose) and the curves for 1.5% dextrose and 4.25% dextrose in FIG. 3.

A kinetic modeling simulation was conducted using the above algorithm for dialysate volume $V_D$, and the following data shown in Table 2 was generated, which shows a comparison of UF estimation and associated error using a known PET and PET 12. Data showed that the PET 12 improved the UF prediction accuracy significantly compared with a known PET.

TABLE 2

UF Prediction Accuracy Using PET 12

| Dwell Time (min) | True UF with Dextrose of 2.5% (mL) | UF Prediction Using Known PET (mL) | UF Prediction Error Using Known PET | UF Prediction Using PET 12 (mL) | UF Prediction Error Using PET 12 |
|---|---|---|---|---|---|
| 30 | 86.73 | 158.81 | 83.1% | 111.48 | 28.5% |
| 60 | 158.74 | 281.52 | 77.3% | 201.28 | 26.8% |
| 90 | 217.88 | 374.37 | 71.8% | 272.49 | 25.1% |
| 120 | 265.71 | 442.21 | 66.4% | 327.68 | 23.3% |
| 150 | 303.61 | 488.92 | 61.0% | 368.98 | 21.5% |
| 180 | 332.76 | 517.70 | 55.6% | 398.25 | 19.7% |
| 210 | 354.20 | 531.24 | 50.0% | 417.04 | 17.7% |
| 240 | 368.86 | 531.79 | 44.2% | 426.72 | 15.7% |
| 270 | 377.54 | 521.28 | 38.1% | 428.48 | 13.5% |
| 300 | 380.95 | 501.35 | 31.6% | 423.35 | 11.1% |
| 330 | 379.73 | 473.44 | 24.7% | 412.23 | 8.6% |
| 360 | 374.42 | 438.79 | 17.2% | 395.92 | 5.7% |
| 390 | 365.53 | 398.44 | 9.0% | 375.11 | 2.6% |
| 420 | 353.49 | 353.34 | 0.0% | 350.42 | −0.9% |
| 450 | 338.69 | 304.29 | −10.2% | 322.39 | −4.8% |
| 480 | 321.48 | 252.00 | −21.6% | 291.49 | −9.3% |
| 510 | 302.16 | 197.07 | −34.8% | 258.15 | −14.6% |
| 540 | 281.00 | 140.03 | −50.2% | 222.73 | −20.7% |

Automated Regimen Generation

As seen in FIG. 1, present system 10 includes a therapy regimen generation module 14. Regimen generation module 14 includes a plurality of prediction algorithms. The prediction algorithms use the above calculated patient transport and UF characteristics from PET 12, target information and other therapy input information to generate the regimens. Regimen generation module 14 in one embodiment generates all of the possible therapy regimens that meet entered target requirements using the therapy input information and calculated patient transport and UF characteristics. The regimens generated are many as shown below. The prescription generation module 16 then filters the regimens generated at module 14 to yield a finite number of optimized prescriptions that can be performed on the APD machine for the particular patient.

FIG. 4A shows one data entry screen for regimen generation module 14. Data entered into the screen of FIG. 4A is obtained from PET 12. FIG. 4A provides PET 12 data inputs for the dialysis center clinical nurse. The data includes the dialysate UF measurement, dialysate lab test results (urea, creatinine and glucose), and blood test results (serum urea, creatinine and glucose). Specifically, an "Overnight Exchange" module of FIG. 4A provides overnight exchange data input, including: (i) % dextrose, (ii) solution type, (iii) volume of solution infused, (iv) volume of solution drained, (v) dwell time(s), (vi) dialysate urea concentration (lab test result from drained dialysate), and (vii) dialysate creatinine concentration (lab test results from drained dialysate). A "Four-Hour Equilibration" module of FIG. 4A provides four-hour exchange data input, which is normally obtained from a patient blood sample taken in a clinic, the data including: (i) % dextrose, (ii) solution type, (iii) volume of solution infused, (iv) volume of solution drained, (v) infusion time, and (vi) drain time. A "Data" module of FIG. 4A provides four-hour exchange data input, including: (i) serum #1 sample time (normally 120 minutes after infusion of the dialysate), urea, creatinine, and glucose concentration, which are the clinician's inputs, "Corrected Crt" is a corrected creatinine concentration that the software algorithm calculates; (ii), (iii) and (iv) for dialysate #1, #2 and #3, sample time, urea, creatinine, and glucose concentration, which are clinician's inputs, "Corrected Crt" and "CRT DIP" (dialysate creatinine/plasma creatinine) which are calculated by software.

Figure 4B:

In FIG. 4B, the "serum concentration" module involves a blood test that is typically performed after the regular APD therapy, preferably in the morning, leading to result sent to the lab for analysis of creatinine, urea, glucose, and albumin. Serum concentration (sometimes called plasma concentration) is the lab test results of blood urea, creatinine and glucose concentration. A patient with end-stage kidney disease has blood urea and creatinine levels that are much higher than for people with functioning kidneys. The glucose concentration is important because it measures how much glucose the patient's body absorbs when using a dextrose-based solution. The "24-hour dialysate and urine collection" module of FIG. 4B shows that the patient has no residual renal function, thus produces no urine. The overnight collection data is used for patient residual renal function ("RRF") calculation, APD therapy results (fill, drain and lab test results), and for measuring the patient height and weight to calculate the patient's body surface area ("BSA"). As seen in the example for the second day of PET 12, (eight hour dwell), 8000 milliliters of dialysate was infused into the patient, 8950 milliliters of dialysate was removed from the patient, yielding a net UF volume of 950 milliliters. The dialysate is sent to the lab for analysis of urea, creatinine, and glucose. A "weekly clearances" module calculates the weekly Urea Kt/V and weekly creatinine clearance ("CCL"), which are parameters that doctors use to analyze if patient has adequate clearance.

FIG. 4C of regimen generation feature 14 shows a sample screen in which system 10 calculates mass transfer coefficients ("MTAC's") and water transport parameters using the data of screens 4A and 4B and stored algorithms. Renal-Soft™ software provided by the assignee of the present invention is one known software for calculating the data shown in FIG. 4C from the input data of FIGS. 4A and 4B. Some of the data calculated and shown in FIG. 4C is used in an algorithm for regimen generation feature 14. Specifically, the regimen generation algorithm uses the MTAC's for urea, creatinine and glucose, and the hydraulic permeability to generate the regimens FIG. 4D of regimen generation feature 14 shows the clinician or doctor the predicted drain volumes determined based on the hydraulic permeability of FIG. 4C versus the actual UF measured from PET 12. The results are shown for an overnight exchange (e.g., night one or night two of PET 12) and the four-hour dwell test performed at the dialysis center 120 or doctor's office 110. The difference between actual drain volume UF and predicted drain volume is calculated so that the clinician or doctor can view the accuracy of PET 12 and the prediction routines of FIGS. 4A to 4D for drain volume and UF. To generate the predicted drain volumes, the operator enters a fluid absorption index. The machine also calculates a fluid absorption value used in the prediction of drain volume. As seen in FIG. 4D, the software of system 10 has calculated the fluid absorption rate to be 0.1 ml/min based on values entered from the patient's PET. As seen at the top of FIG. 4D, the actual versus predicted drain volume for the overnight exchange was 2200 ml versus 2184 ml. The four hour (day) predicted drain versus the actual drain was 2179 ml versus 2186 ml. The bottom of FIG. 4D shows the actual versus predicted drain values for a more common fluid absorption rate of 1.0 ml/min, which are not as close to one another as those for the 0.1 ml/min fluid absorption rate. The system can then ask the clinician to enter a fluid absorption rate that he/she would like to use for this patient when predicting UF, which is normally somewhere between and including 0.1 ml/min and 1.0 ml/min.

Figure 5:
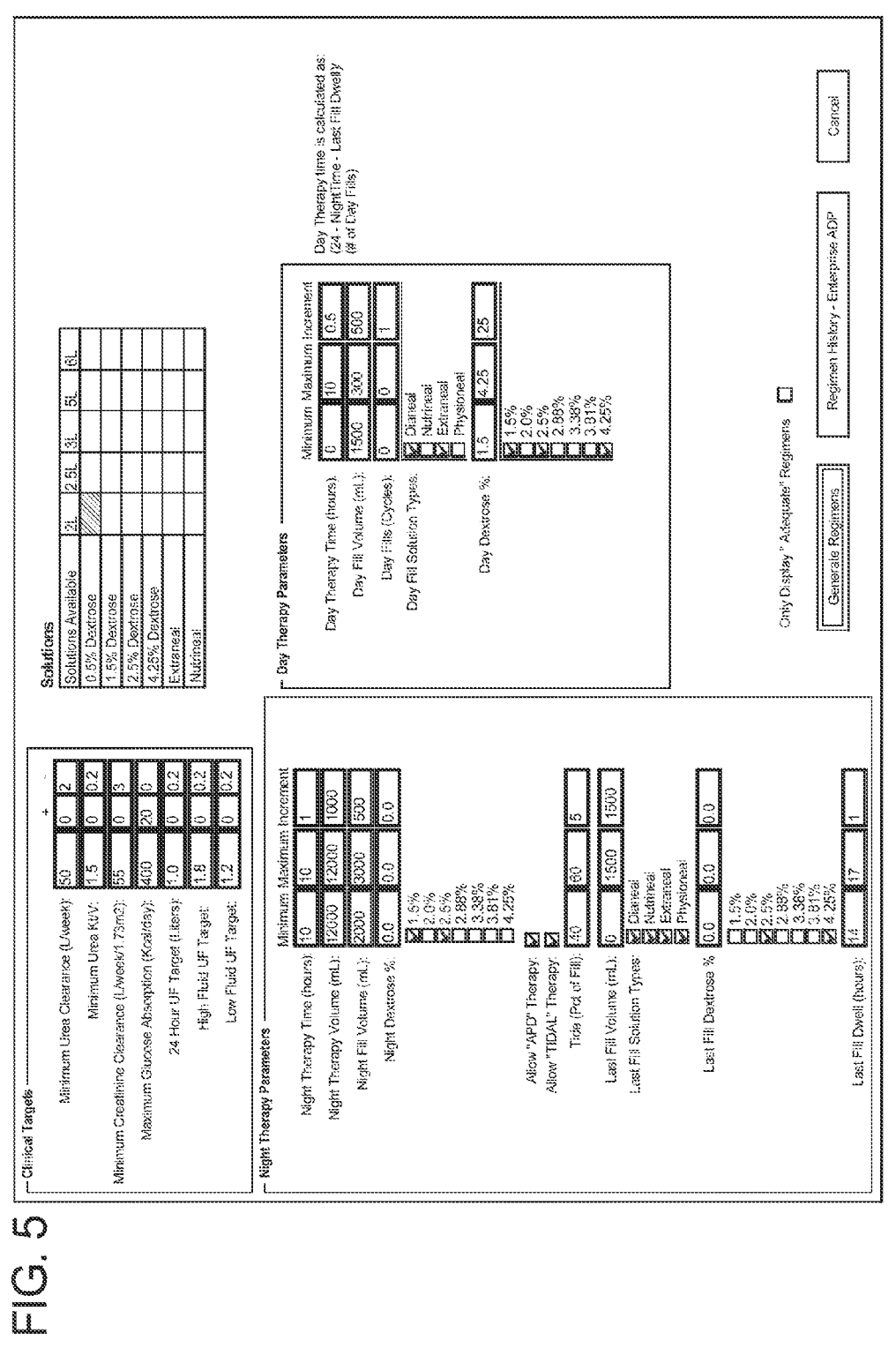

FIG. 5 illustrates one possible regimen calculation input table for regimen generation feature 14. The regimen calculation input table inputs Clinical Targets data including (a) minimum urea clearance, (b) minimum urea Kt/V, (c) minimum creatinine clearance, (d) maximum glucose absorption, and (e) target UF (e.g., over twenty-four hours).

The table of FIG. 5 also inputs Night Therapy Parameters data, such as (i) therapy time, (ii) total therapy volume, (iii) fill volume, (iv) percent dextrose for the chosen solution type, and possibly (v) solution type. Here, dwell times and number of exchanges are calculated from (ii) and (iii). Dwell time can alternatively be set according to the results of PET 12 as discussed above, which can be used in combination with at least one other input, such as, total time, total volume and fill volume to calculate the remainder of total time, total volume and fill volume inputs. For example, if dwell time, total volume and total time are set, system 10 can calculate the fill volume per exchange and the number of exchanges. The Night Therapy Parameters input also includes last fill inputs, such as (i) dwell time, (ii) last fill volume, and (iii) percent dextrose for the chosen solution type.

The table of FIG. 5 also inputs Day Therapy Parameters data, such as (i) therapy time, (ii) day fill volume, (iii) number of cycles, (iv) percent dextrose for the chosen solution type, and possibly (v) solution type. Day exchanges may or may not be performed.

Solution type for the night and day therapies is chosen from a Solutions portion of the input table of FIG. 5, which inputs available dextrose levels, solution formulation (e.g., Dianeal®, Physioneal®, Nutrineal®, and Extraneal® dialysates marketed by the assignee of the present disclosure) and bag size. Bag size can be a weight concern especially for elderly patients. Smaller bags may be needed for regimens that use a different last fill and/or day exchange solution or dextrose level. Smaller bags may also be needed for regimens that call for a dextrose level that requires a mix from two or more bags of standard dextrose level (e.g., dextrose level of 2.0%, 2.88%, 3.38%, or 3.81%) listed under the Solutions portion of the table of FIG. 5. Mixing to produce customized dextrose level is discussed below in connection with FIG. 14. Solution bag inventory management is also discussed below in connection with FIGS. 10 to 13.

The regimen calculation input table of FIG. 5 also illustrates that many of the inputs have ranges, such as plus/minus ranges for the Clinical Targets data and minimum/maximum/increment ranges for certain Night Therapy Parameters data and Day Therapy Parameters data. Once the clinician or doctor starts to complete the table of FIG. 5, system 10 automatically places suggested values in many of the other cells, minimizing the amount of entries. For example, the solutions available under Solutions data can be filled automatically based upon the solutions that have been indicated as available by the dialysis center, which is further based the available solution portfolio approved for a specific country. In another example, system 10 can adjust the fill volume increments for Night Therapy Parameters data automatically to use all of the available solutions (e.g., when a twelve liter therapy is being evaluated, the number of cycles and the fill volumes can range as follows: four-3000 mL fills, five-2400 mL fills, six-2000 mL fills, and seven-1710 mL fills). System 10 allows the operator to change any of the suggested values if desired.

The software of system 10 calculates the predicted outcomes for all of the possible combinations of parameters based upon the ranges that are entered for each parameter. As seen in FIG. 5, some regimens will have "adequate" predicted outcomes for urea clearance, creatinine clearance and UF that meet or exceed the minimum criteria selected by the clinician. Others will not. Selecting "Only Display Adequate Regimens" speeds the regimen generation process. Some patients may have hundreds of regimens that are adequate. Others may have only few, or possibly even none. When none are adequate, it may be necessary to display all regimens so that the regimens that are close to meeting the target requirements can be identified for filtering. Filtering when starting with all regimens displayed provides the clinician/doctor the most flexibility when trying to find the best prescription for the patient.

System 10 feeds all of the therapy combinations into outcome prediction software and tabulates the results in a table that system 10 can then filter through as shown below in connection with prescription filtering module 16. One suitable software is RenalSoft™ software provided by the assignee of the present disclosure. The combinations take into account the different ranges entered above in the regimen calculation input table of FIG. 5.

Table 3 below shows the first ten results (of a total of 270 results) for one set of data inputted into system software. Here, a 1.5% night dextrose solution is chosen. No day exchange is allowed. Results are shown generated for a standard PD therapy but could alternatively or additionally be generated for other types of PD therapies, such as a tidal therapy. FIG. 5 has check boxes that allow either one or both of continuous cycling peritoneal dialysis ("CCPD") or tidal therapies (both APD therapies) to be included in the regimen generation process.

TABLE 3

APD Therapy

| | Night Dex | Night Ther Time | Night Ther Volume | Night Fill Volume | Number of Night Exch | Last Fill Volume | Last Fill Solution | Last Fill Dwell Time | Number of Day Exch | Day Fill Volume | Day Fill Solution | Day Fill Dwell Time |
|---|---|---|---|---|---|---|---|---|---|---|---|---|
| 1 | 1.5 | 7 | 8 | 2 | 4 | 0 | 0 | 0 | 0 | 0 | 0 | 0 |
| 2 | 1.5 | 7 | 8 | 2.2 | 3 | 0 | 0 | 0 | 0 | 0 | 0 | 0 |
| 3 | 1.5 | 7 | 8 | 2.4 | 3 | 0 | 0 | 0 | 0 | 0 | 0 | 0 |
| 4 | 1.5 | 7 | 8 | 2.6 | 3 | 0 | 0 | 0 | 0 | 0 | 0 | 0 |
| 5 | 1.5 | 7 | 8 | 2.8 | 3 | 0 | 0 | 0 | 0 | 0 | 0 | 0 |
| 6 | 1.5 | 7 | 8 | 3 | 2 | 0 | 0 | 0 | 0 | 0 | 0 | 0 |
| 7 | 1.5 | 7 | 9 | 2 | 4 | 0 | 0 | 0 | 0 | 0 | 0 | 0 |
| 8 | 1.5 | 7 | 9 | 2.2 | 4 | 0 | 0 | 0 | 0 | 0 | 0 | 0 |
| 9 | 1.5 | 7 | 9 | 2.4 | 3 | 0 | 0 | 0 | 0 | 0 | 0 | 0 |
| 10 | 1.5 | 7 | 9 | 2.6 | 3 | 0 | 0 | 0 | 0 | 0 | 0 | 0 |

As stated, Table 3 illustrates ten of two-hundred seventy valid combinations possible with a 1.5% night dextrose level. The same two-hundred seventy combinations will also exist for 2% dextrose level, 2.5%, etc., night dextrose level. An equal number of valid combinations is created for each possible dextrose level when a day fill is added. Further, the last fill dwell time can be varied to create even more valid combinations.

Prescription Filtering

As shown above, system 10 allows the doctor/clinician to prescribe values for clinical targets and therapy inputs, such as patient fill volume, total therapy volume, total therapy time, etc., and generates a table, such as Table 3, containing all therapies that meet all of the clinical requirements. The table of therapies that meet all of the clinical requirements can then be automatically filtered and sorted based upon parameters such as total night therapy time, therapy solution cost, therapy weight, etc.

The software uses one or more algorithm in combination with the therapy combinations (e.g., of Table 3) and the patient physiologic data generated via PET 12 as shown in connection with FIGS. 4A to 4D to determine predicted therapy results. Therapy combinations (e.g., of Table 3) that meet the Clinical Targets of FIG. 5 are filtered and presented to the clinician, nurse or doctor as candidates to become prescribed regimens.

Figure 6A:
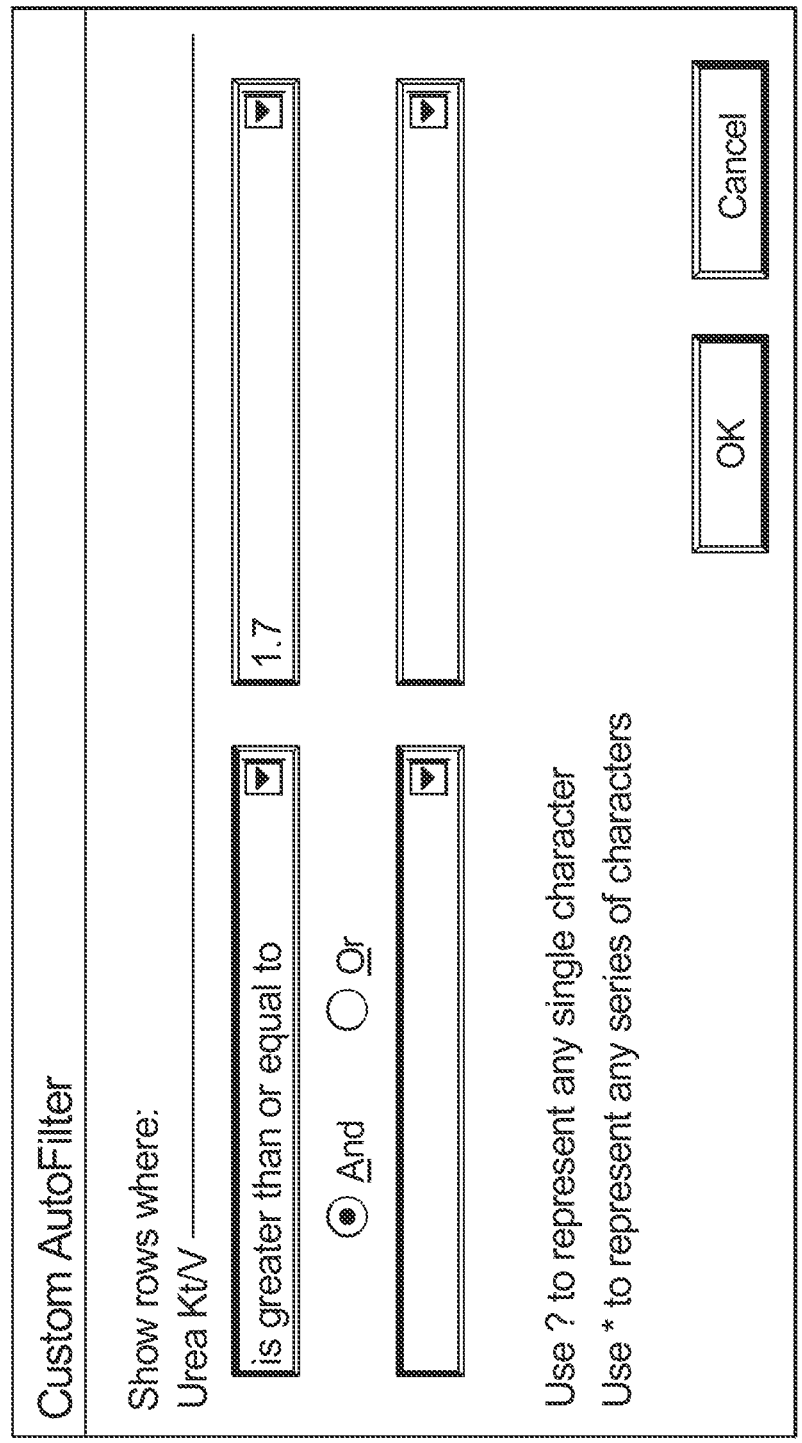

FIGS. 6A and 6B illustrate examples of filters that the doctor or clinician can use to eliminate regimens. In FIG. 6A, minimum Urea Kt/V removal is increased from 1.5 in FIG. 5 to 1.7 in FIG. 6A. In one embodiment, the range of +0 to −0.2 in FIG. 5 is applied automatically to the new minimum value set in FIG. 6A. Alternatively, system 10 prompts the user to enter a new range or keep the same range. A Boolean "And" operator is applied to the new minimum Urea Kt/V to specify that the value must be met, subject to the applied range, in combination with the other clinical targets.

In FIG. 6B, minimum twenty-four hour UF removal is increased from 1.0 in FIG. 5 to 1.5 in FIG. 6B. In one embodiment, the range of +0 to −0.2 in FIG. 5 is again applied automatically to the new minimum value set in FIG. 6B. Alternatively, system 10 prompts the user to enter a new daily UF range or keep the same UF range. Again, a Boolean "And" operator is applied to the new minimum twenty-four hour UF to specify that the value must be met, subject to the applied range, in combination with the other clinical targets. The clinician and patient are free to impose additional, clinical and non clinical requirements, such as: solution cost, solution bag weight, glucose absorbed, night therapy time, day fill volume, night fill volume.

Referring now to FIG. 7A, the regimens that meet the Clinical Targets and other inputs of FIG. 5 and the additional filtering of FIGS. 6A and 6B are shown. As seen, each of the regimens is predicted to remove at least 1.5 liters of UF per day and has a minimum Urea Kt/V removal of greater than 1.5.

Regimen 36 is highlighted because it has the smallest day fill volume (patient comfort), the lowest solution weight (patient convenience), and the next to lowest glucose absorption value (least dietary impact). Thus, regimen 36 is chosen and prescribed by a doctor as a standard UF regimen.

The patient, clinician and/or doctor can also pick one or more additional prescription for approval that also meets with a patient's lifestyle needs. Suppose for example that the patient is a member of a bowling team during the winter months that competes in a Saturday night league. He drinks a little more than normal while socializing. The patient and his doctor/clinician agree that a therapy regimen that removes about 20% more UF should therefore be performed on Saturday nights. Also, on bowling nights, the patient only has seven hours to perform therapy rather a standard eight hour therapy. Filtered potential prescription 34 highlighted in FIG. 7A is accordingly approved as a higher UF prescription, which uses a higher dextrose concentration to remove the extra UF and does so in the required seven hours.

Further, suppose that the patient lives in a southern state and does yard work on the weekends during the summer months (no bowling league) and accordingly loses a substantial amount of body fluid due to perspiration. The doctor/clinician and patient agree that less than 1.5 liters of UF needs to be removed on such days. Because FIG. 7A only shows regimens that remove at or over 1.5 liters of UF, further filtering is used to provide low UF regimens for possible selection as a low UF prescription.

The doctor or clinician uses an additional filtering of the twenty-four hour UF screen of FIG. 6C to restrict the prior range of daily UF that the regimes must meet. Here, the doctor/clinician looks for regimes having daily UF removals of greater than or equal to 1.1 liter and less than or equal to 1.3 liters. The Boolean "And" operator is selected such that the therapy meets all of the other clinical requirements of FIGS. 5 and 6A.

Referring now to FIG. 7B, the regimens that meet the Clinical Targets and other inputs of FIG. 5 and the additional filtering of FIGS. 6A and 6C are shown. As seen, each of the regimens is predicted to remove at or between 1.1 and 1.3 liters of UF per day, while meeting the minimum Urea Kt/V removal of greater than 1.5 and other clinical targets. The doctor/clinician and patient then decide on a tidal therapy regimen 58 (highlighted), which does not require a day exchange, and requires the shortest night therapy time. The doctor then prescribes the therapy.

Referring now to FIGS. 8A to 8C, the three agreed-upon high UF, standard UF and low UF prescriptions are illustrated, respectively. The prescriptions are named (see upper-right corner), so that they are easily recognizable by the patient 102, doctor 110 and clinician 120. While three prescriptions are shown in this example, system 10 can store other suitable numbers of prescriptions as discussed herein. System 10 downloads the prescription parameters onto a data card in one embodiment, which is then inserted in the APD machine 104, transferring the prescriptions to the non-volatile memory of the APD machine. Alternatively, the prescriptions are transferred to APD machine 104 via a wired data communications link, such as via the internet. In one embodiment, the patient is free to choose which prescription is performed on any given day. In an alternative embodiment, the data card or data link transfer of the prescriptions is entered into the memory of the dialysis instrument, such that the instrument runs a prescribed treatment each day automatically. These embodiments are discussed in detail below in connection with the prescription recall and adjustment module 26. In any case, when the patient starts any of the therapies, system 10 provides instructions on which solution bags to connect to a disposable cassette for pumping since the therapies may use different solutions.

Figure 9B:
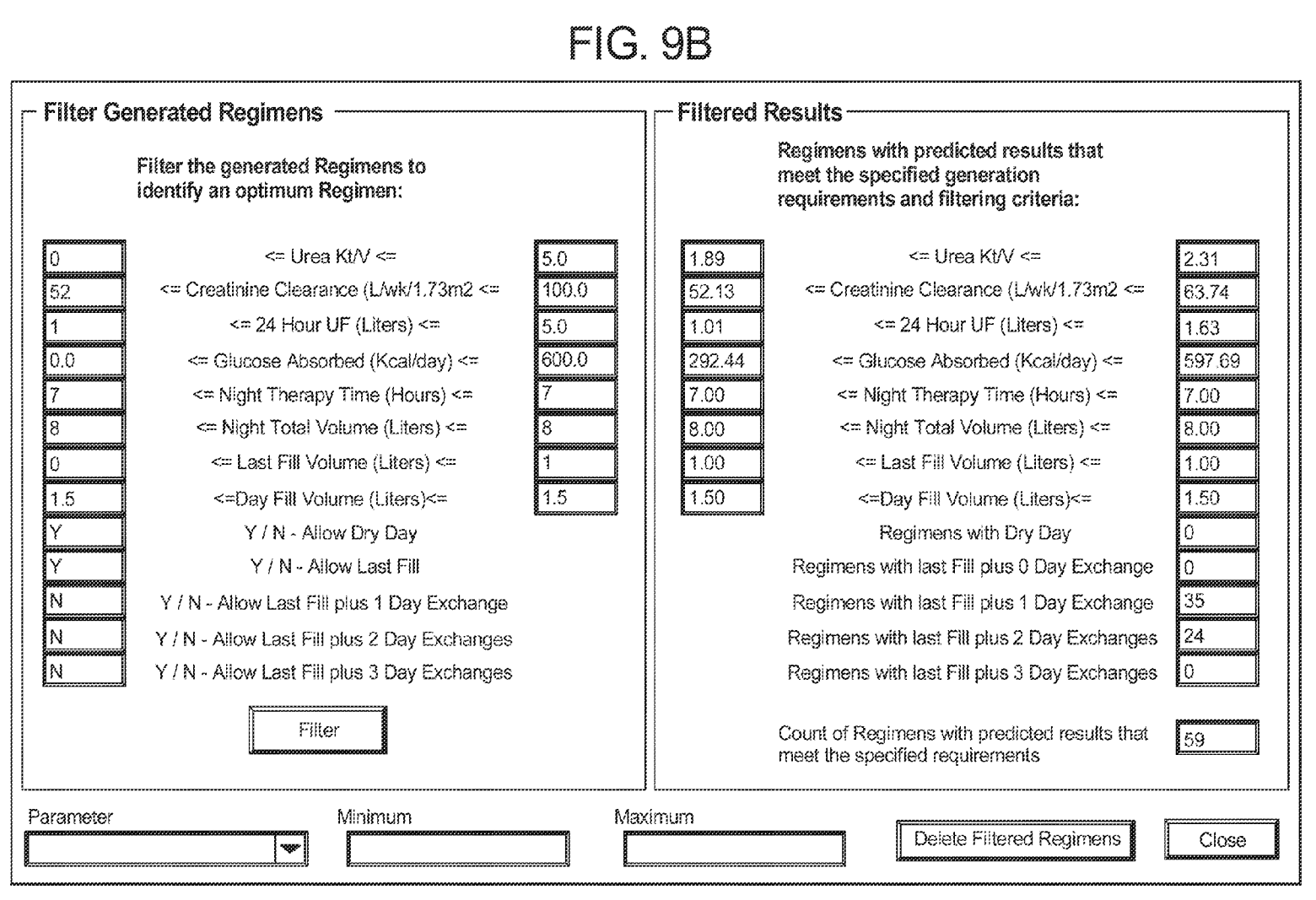
Figure 9C:
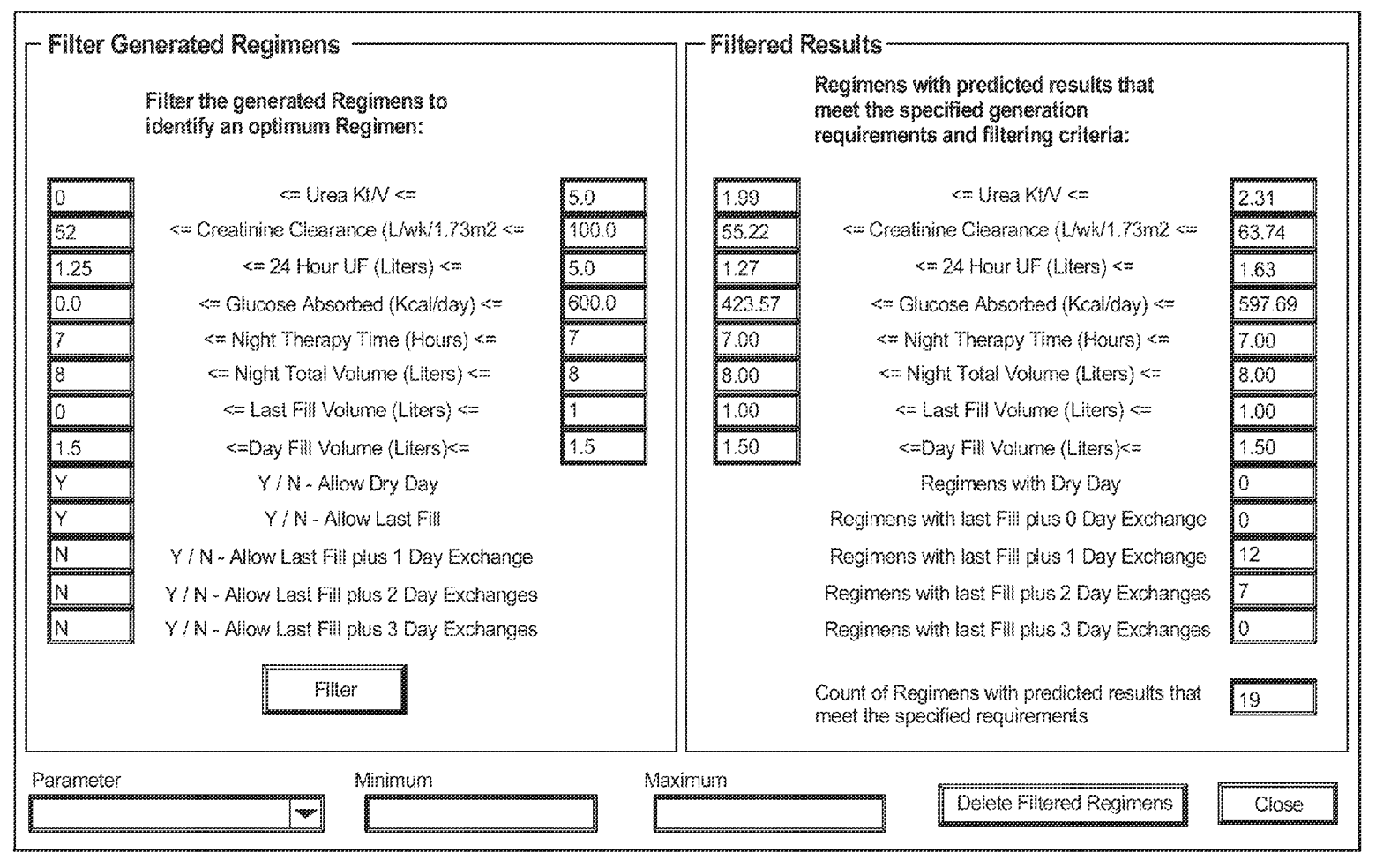

FIGS. 9A to 9E illustrate another filtering example for module 16. FIG. 9A illustrates filtered settings on the left and corresponding results on the right, which yield 223 possible regimens. In FIG. 9B, the clinician further filters to regimens by limiting the day fill volume (patient comfort) to 1.5 liters. Such filtering reduces the possible regimens to 59. In FIG. 9C, the clinical software further filters the regimens by decreasing the regimens to 19. In FIG. 9D, the clinical further filters the available regimens by reducing the glucose absorbed to 500 Kcal/day. Such action reduces the available regimens to three.

Figure 9E:
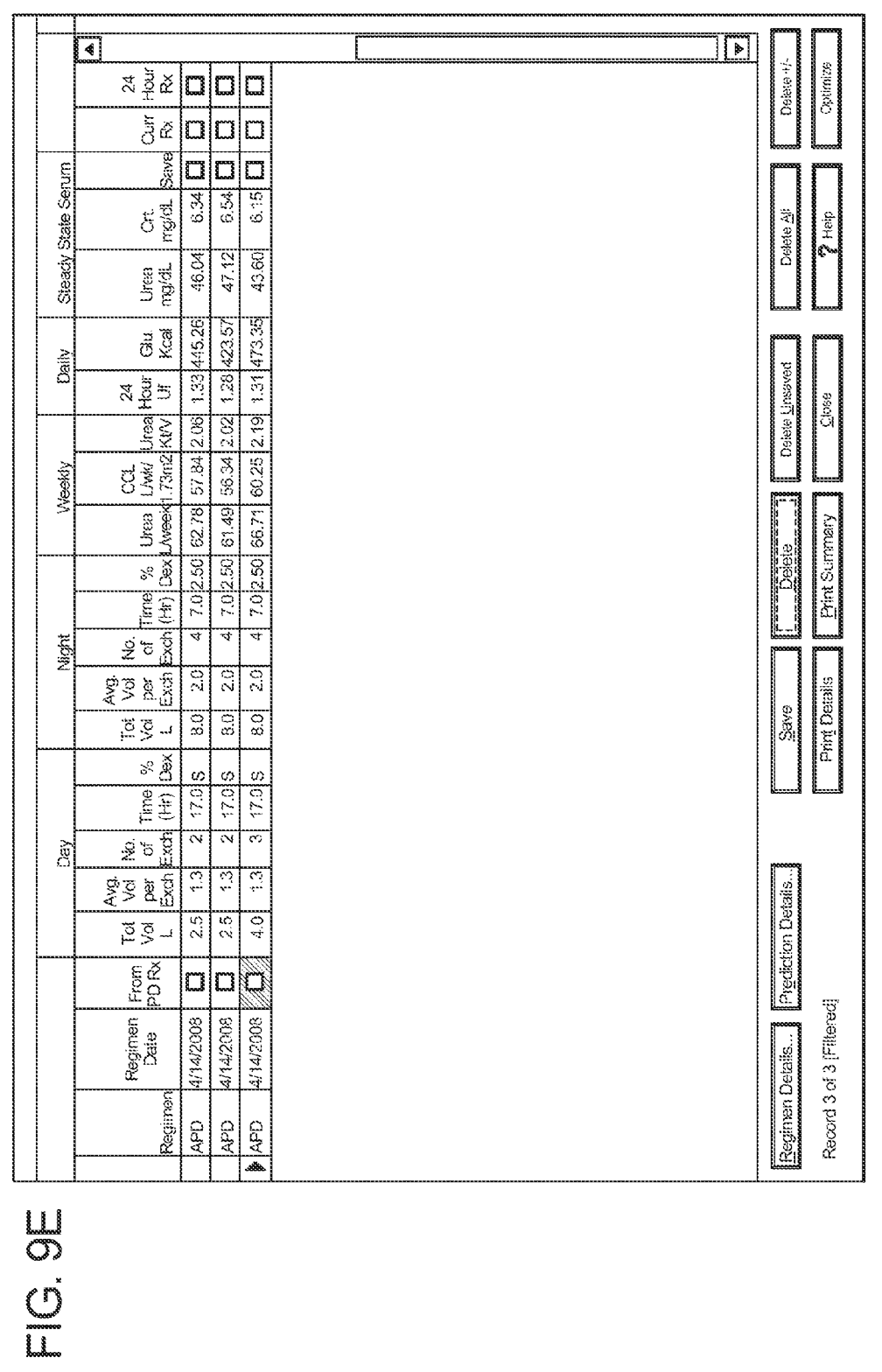

FIG. 9E shows the three filtered regimens that can either be prescribed by the physician or discarded to enable another filtering exercise to be performed. The exercise of FIGS. 9A to 9D shows that prescription optimization is made convenient once the patient's physiological characteristics are known. FIGS. 9A to 9D also show suitable lists of possible filtering criteria.

Inventory Tracking

Referring now to FIGS. 10 to 13, one embodiment for an inventory tracking subsystem or module 18 of system 10 is illustrated. As discussed herein, system 10 generates agreed-upon prescriptions, such as high UF, standard UF and low UF prescriptions as shown in connection with FIGS. 8A to 8C. The different prescriptions require different solutions as seen in FIG. 10. FIG. 10 shows that the standard UF prescription uses twelve liters of 1.5% Dianeal® dialysate and two liters of Extraneal® dialysate. The high UF prescription uses fifteen to eighteen (depending on alternate dialysis used) liters of 1.5% Dianeal® dialysate and two liters of Extraneal® dialysate. The low UF prescription uses twelve liters of 1.5% Dianeal® dialysate and three liters of 2.5% Dianeal® dialysate.

FIG. 11 shows an example screen that a server in a dialysis center 120 can display for a patient having the above three prescriptions. The screen of FIG. 11 shows the minimum base supply inventory needed for the three prescriptions over a delivery cycle. The screen of FIG. 11 shows that the patient is to be supplied the solutions needed to perform thirty-two standard UF prescription therapies. The patient is to be supplied the solutions needed to perform six high UF prescription therapies. The patient is also to be supplied the solutions needed to perform six low UF prescription therapies. The patient is further to be provided one "ultrabag" case (six 2.5 liter bags). The stem of a Y-shaped ultrabag tubing set can connect to the patient's transfer set. An empty bag is attached to the one leg of the Y and a full bag is pre-attached to the other leg of the Y. The ultrabag is used to perform CAPD exchanges if the APD machine breaks, if power is lost and the APD machine cannot operate, or if the patient is traveling and his/her supplies do not arrive on time.

Additionally, the patient is also to be provided with forty-five disposable sets (one used for each treatment), which includes a disposable pumping cassette, bag line, patient line, drain line, heater bag and associated clamps and connectors. The patient is provided with low (1.5%), medium (2.5%) and high (4.25%) dextrose concentration dialysis solutions, so that the patient can remove more or less fluid by switching which dextrose level is used. Prescription flexibility (including mixing) could increase the total number of bags needed for a given month to about forty-five days worth of solutions.

The patient is also to be provided forty-five caps or flexicaps, which are used to cap the patient's transfer set when the patient is not connected to the cycler. The flexicaps contain a small amount of povidone iodine to minimize the potential for bacterial growth due to touch contamination.

FIG. 12 shows an example screen that the dialysis center 120 can display for a patient having the above three prescriptions. The screen of FIG. 12 shows the expected actual patient inventory at the time a new delivery of inventory is to be made. That is, the screen of FIG. 12 shows what inventory the server computer thinks will be at the patient's home when the delivery person arrives. In the example, the server computer expects that when the delivery person arrives at the patient's home, the patient will already have: (i) five cases (two bags per case) of 1.5% Dianeal® dialysate containing six liter bags, (ii) one case (four bags per case) of 2.5% Dianeal® dialysate containing three liter bags, (iii) one case (six bags per case) of Extraneal® dialysate containing two liter bags, (iv) twenty-four (out of a case of thirty) disposable sets, each including the apparatuses described above, (v) two 1.5%, 2.5 liter Ultrabags of dialysate (out of a case of 6), and six caps or flexicaps (out of a case of thirty).

FIG. 13 shows an example screen that the server of dialysis center 120 can display for a patient having the above three prescriptions. The screen of FIG. 13 shows the actual inventory that will be delivered to the patient. That is, the screen of FIG. 13 shows the inventory difference between what the patient is supposed to have at the start of the inventory cycle and what the server computer thinks will be at the patient's home when the delivery person arrives. In the example, the patient needs: (i) eighty-eight, six liter bags of 1.5% Dianeal® dialysate, has ten at home, reducing the need to seventy-eight bags or thirty-nine cases (two bags per case); (ii) six, three liter bags of 2.5% Dianeal® dialysate, has four at home, reducing the need to two bags or one case (four bags per case, resulting in two extra delivered); (iii) thirty-eight, two liter bags of Extraneal® dialysate, has six at home, reducing the need to thirty-two bags or six cases (six bags per case, resulting in four extra delivered); (iv) forty-five disposable sets, has twenty-four at home, reducing the need to twenty-one or one case (thirty per case, resulting in nine extra disposable sets delivered); (v) six, 2.5 liter 1.5% Ultrabags, has two at home, reducing the need to four bags or one case (six bags per case, resulting in two extra ultrabags delivered); and (vi) forty-five flexicaps, has thirty-six at home, reducing the need to nine or one case (thirty-six per case, resulting in twenty-seven extra flexicaps delivered).

In one embodiment, the dialysis center server database of the inventory tracking module 18 maintains and knows: (a) how much of each dialysate and other supplies the patient is supposed to have at the beginning of a delivery cycle; (b) the patient's different prescriptions, solutions used with each, and the number of times each prescription is to be used over the delivery cycle; and (c) accordingly how much of each dialysate the patient is supposed to use over a delivery cycle. Knowing the above, the inventory tracking server can calculate how much of each solution and other supplies needs to be delivered at the next delivery date. Chances are the patient has consumed more or less of one or more solution or other item than expected. For example, the patient may have punctured a solution bag, which then had to be discarded. The patient may misplace a solution bag or other item. Both instances result in more inventory being consumed than expected. On the other hand, the patient may skip one or more treatment over the course of the delivery cycle, resulting in less inventory being consumed than expected.

In one embodiment, the inventory tracking module or subsystem 18 of system 10 expects that the estimated amount of solutions and other supplies is close to the actual amount needed. If too much inventory is delivered (patient used less than prescribed), the delivery person can deliver the extra inventory to the patient and scan or otherwise note the additional inventory, so that it can be saved into the inventory server memory. For the next cycle, system 10 updates (e.g., increases) (a) above, namely, how much of each dialysate and other supplies the patient is supposed to have at the beginning of a delivery cycle. Alternatively, the delivery person only delivers the needed amount of inventory, so as to make the patient's actual inventory at the beginning of the delivery cycle equal to the expected inventory at (a) above. If not enough inventory is scheduled for delivery (patient lost or damaged solution or related supplies for example), the delivery person brings extra inventory so as to make the patient's actual inventory at the beginning of the delivery cycle equal to the expected inventory at (a) above.

The inventory subsystem 18 of system 10 in one embodiment maintains additional information such as the individual cost of the supplies, the weight of the supplies, alternatives for the required supplies if the patient depletes the required supplies during the delivery cycle. As shown above in FIGS. 7A and 7B, the regimen generation software in one embodiment uses or generates the weight and cost data as a factor or potential factor in determining which regimes to be selected as prescriptions. The server of the dialysis center 120 downloads (or transfers via data card) the alternative solution data to the patient's APD Cycler. In one implementation, when a patient starts a therapy, the patient is notified of the particular solution bag(s) needed for that day's particular prescription. If the patient runs outs of one type of solution, the system can provide an alternative based upon the solutions held in current inventory.

Dextrose Mixing

As shown above in FIG. 5, system 10 contemplates using a plurality of different dextrose levels for each of the different brands or types of dialysates available, which increases the doctor/clinician's options in optimizing prescriptions for the patient. The tradeoff with dextrose is generally that higher levels of dextrose remove more UF but have higher caloric input, making weight control for the patient more difficult. The converse is also true. Dialysate (at least certain types) is provided in different standard dextrose levels including 0.5%, 1.5%, 2.5% and 4.25%. As seen in FIG. 6, night dextrose, last fill dextrose and day dextrose can be chosen to have any of the above standard percentages or to have a blended dextrose level of 2.0%, 2.88%, 3.38% or 3.81%. System 10 uses the dialysis instrument 104 to mix the standard percentages to create the blended percentages. It is believed that since each of the standard dextrose level dialysates has been approved by the Federal Drug Administration ("FDA") and that the blended dextrose levels are within approved levels, that such mixing would meet readily with FDA approval.

TABLE 4

Glucose-Based Solutions Mixing Ratios and Concentrations.

| Dextrose Concentration (%) | Mixing Ratio | Dextrose Concentration (%) after mixing | Available Solutions of Dextrose Concentration (%) |
| --- | --- | --- | --- |
| 1.5 and 2.5 | 1 to 1 | 2.00 | 1.5 |
| 1.5 and 4.25 | 1 to 1 | 2.88 | 2.0 |
| 2.5 and 4.25 | 1 to 1 | 3.38 | 2.5 |
| 2.5 and 4.25 | 1 to 3 | 3.81 | 2.88 |
| | | | 3.38 |
| | | | 3.81 |
| | | | 4.25 |

Using 1:1 or 1:3 mixing shown in Table 4 generates more dextrose solutions, providing more therapy options for clinicians. At the same time, these mixing ratios will use all the solution in a container, resulting in no waste.

Referring now to FIG. 14, dialysis instrument 104 illustrates one apparatus capable of producing the blended dextrose level dialysates. Dialysis instrument 104 is illustrated as being a HomeChoice® dialysis instrument, marketed by the assignee of the present dialysate. The operation of the HomeChoice® dialysis instrument is described in many patents including U.S. Pat. No. 5,350,357 ("the '357 patent"), the entire contents of which are incorporated herein by reference. Generally, the HomeChoice® dialysis instrument accepts a disposable fluid cassette 50, which includes pump chambers, valve chambers and fluid flow pathways that interconnect and communicate fluidly with various tubes, such as a to/from heater bag tube 52, a drain tube 54, a patient tube 56 and dialysate supply tubes 58a and 58b. While FIG. 14 shows two supply tubes 58a and 58b, dialysis instrument 104 and cassette 50 can support three or more supply tubes and thus three or more supply bags. Further, as seen in the '357 patent, one or both supply tubes 58a and 58b can Y-connect to two supply bags if more supply bags are needed.

In one embodiment, system 10 pumps fluid from a supply bag (not shown), through one of supply tubes 58a or 58b, cassette 50, to a warmer bag (not shown) located on a heater tray of APD 104. The warmer bag provides an area for the solutions to mix before being delivered to the patient. In such a case, the warmer bag can be fitted with one or more conductive strip, which allows a temperature compensated conductivity reading of the mixed solution to be taken to ensure that the solutions have been mixed properly. Alternatively, APD 104 uses inline heating in which case the mixing is done in the tubing and the patients peritoneum.

To operate with cassette 50, the cassette is compressed between a cassette actuation plate 60 and a door 62. The '357 patent describes a flow management system ("FMS"), in which the volume of fluid pumped from each pump chamber (cassette 50 includes two in one embodiment), after each pump stroke is calculated. The system adds the individual volumes determined via the FMS to calculate a total amount of fluid delivered to and removed from the patient.

System 10 contemplates proportioning the pump strokes from different standard dextrose supplies using FMS to achieve a desired blended dextrose. As seen at Table 4 above, a 1.5% standard dextrose supply bag can be connected to supply line 58a, while a 4.25% standard dextrose supply bag is connected to supply line 58b. Dialysis machine 104 and cassette 50 pump dialysate from each supply bag in a 50/50 ratio using FMS to achieve the 2.88% blended dextrose ratio. In another example, a 2.5% standard dextrose supply bag is connected to supply line 58a, while a 4.25% standard dextrose supply bag is connected to supply line 58b. Dialysis machine 104 and cassette 50 pump dialysate from each supply bag in a 50/50 ratio using FMS to achieve the 3.38% blended dextrose ratio. In a further example, a 2.5% standard dextrose supply bag (e.g. 2 L bag) is connected to supply line 58a, while a 4.25% standard dextrose supply bag (e.g. 6 L bag) is connected to supply line 58b. Dialysis machine 104 and cassette 50 pump dialysate from each supply bag in a 25/75 (2.5% to 4.25%) ratio using FMS to achieve the 3.81% blended dextrose ratio.

The first two examples can include a connection of a six liter bag of dialysate to each of lines 58a and 58b. In the third example, a three liter 2.5% standard dextrose supply bag is connected to supply line 58a, while a three liter 4.25% supply bag is Y-connected to a six liter 4.25% supply bag, which are both in turn connected to supply line 58b. Dialysis machine 104 and cassette 50 pump dialysate from each supply bag to a heater bag in one embodiment, which allows the two different dextrose dialysates to fully mix before being pumped from the heater bag to the patient. Accordingly, system 10 can achieve the blended dialysate ratios shown in FIG. 6 and others by pumping different standard dextrose levels at different ratios using FMS. Dialysis instrument 104 in one embodiment is configured to read bag identifiers to ensure that the patient connects the proper dialysates and proper amounts of the dialysate. Systems and methods for automatically identifying the type and quantity of dialysate in a supply bag are set forth in U.S. patent application Ser. No. 11/773,822 ("the '822 application"), entitled "Radio Frequency Auto-Identification System", filed Jul. 5, 2007, assigned to the assignee of the present disclosure, the entire contents of which are incorporated herein by reference. The '822 application discloses one suitable system and method for ensuring that the proper supply bags are connected to the proper ports of cassette 50. System 10 can alternatively use a barcode reader that reads a barcode placed on the bag or container for solution type/volume identification. In the case in which Y-connections are needed, APD machine 104 can prompt the patient to confirm that the Y-connection(s) to an additional bag(s) has been made.

Figure 17:
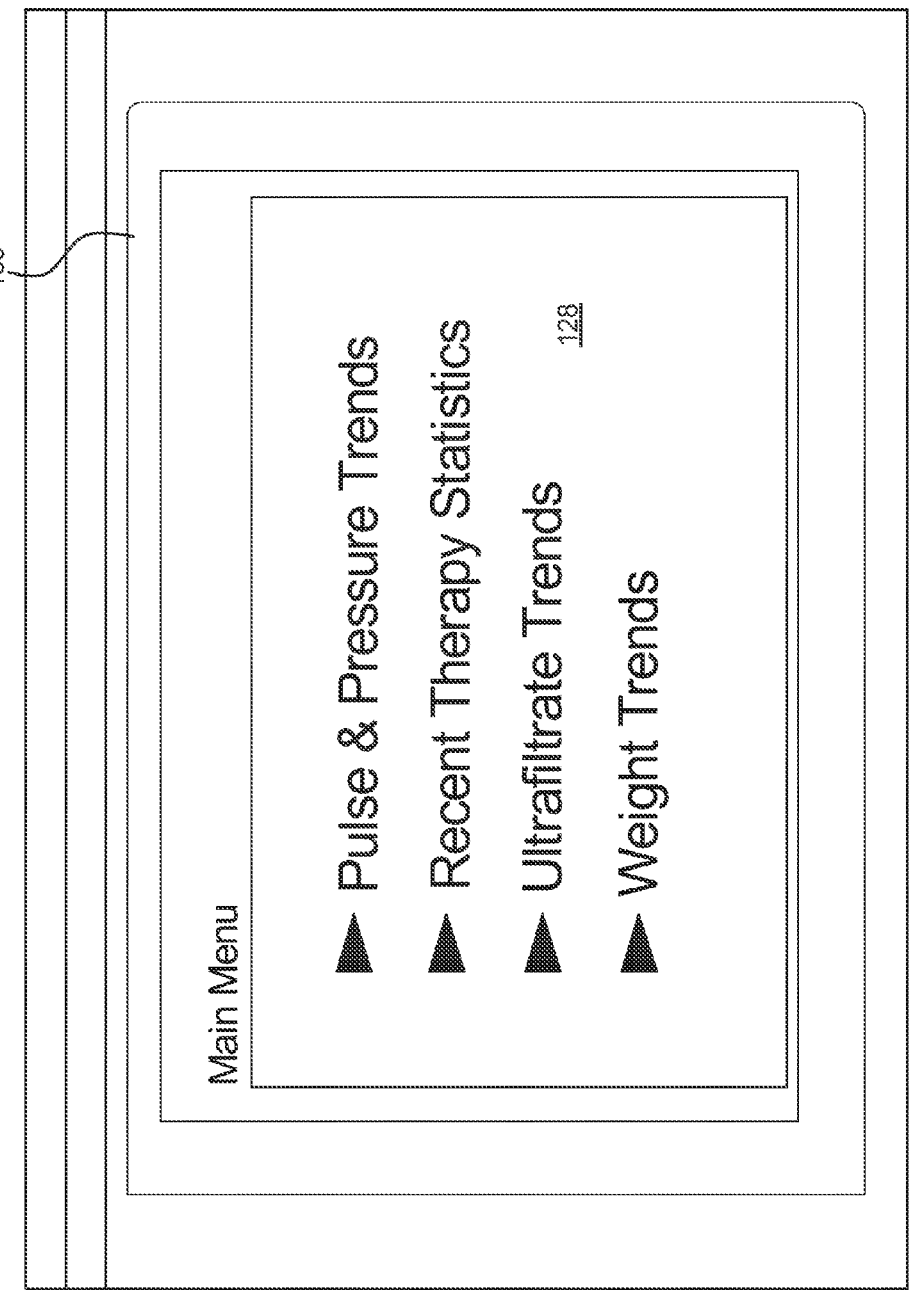
FIGS. 17 to 21 are sample screens displayed on a patient's dialysis instrument illustrating various trending data available to the patient.

U.S. Pat. No. 6,814,547 ("the '547 patent") assigned to the assignee of the present disclosure, discloses a pumping mechanism and volumetric control system in connection with FIGS. 17A and 17B and associated written description, incorporated herein by reference, which uses a combination of pneumatic and mechanical actuation. Here, volume control is based on precise control of a stepper motor actuator and a known volume pump chamber. It is contemplated to use this system instead of the FMS of the '357 patent to achieve the above blended dextrose levels.

Prescription Download and Therapy Data Upload Communication Module

Figure 15A:
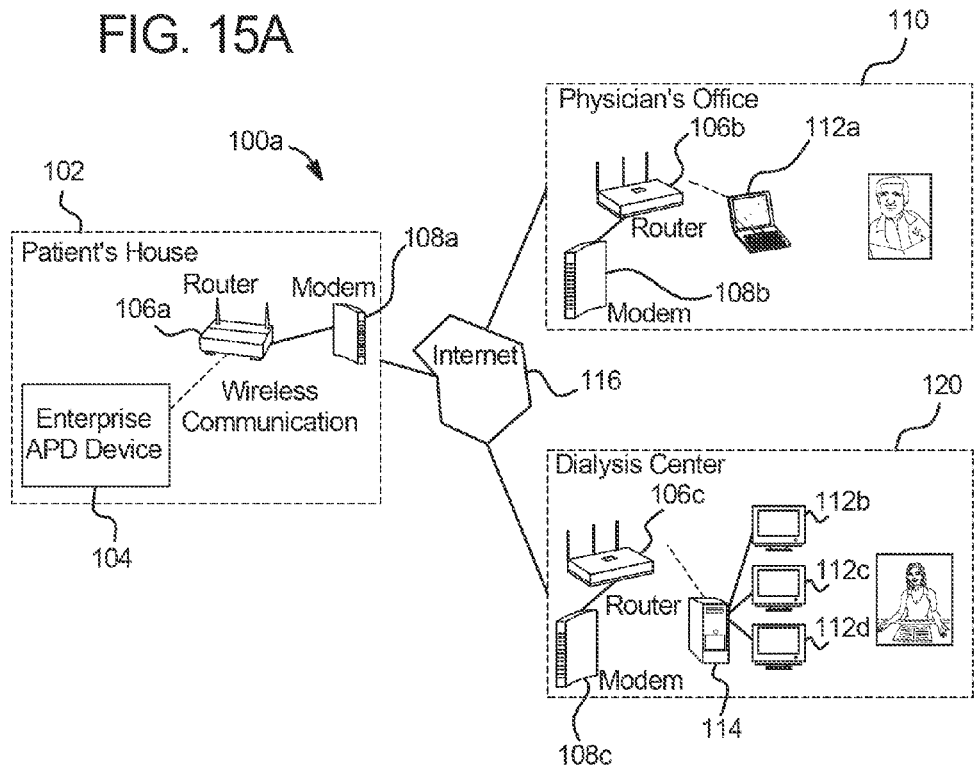
FIGS. 15A and 15B are schematic views illustrating embodiments for wireless and wired communications modules, respectively, for the prescription optimization system of the present disclosure.

Referring now to FIG. 15A, network 100a illustrates one wireless network or communication module 20 (FIG. 1) for communicating the PET, regimen generation, prescription filtering, inventory tracking, trending and prescription modification information (below) between patient 102, doctor 110 and dialysis center 120. Here, the patient 102 operates a dialysis instrument 104, which communicates wirelessly with a router 106a, which is in wired communication with a modem 108a. The doctor 110 operates the doctor's (or nurse's) computer 112a (which could also be connected to a doctor's network server), which communicates wirelessly with a router 106b, which is in wired communication with a modem 108b. The dialysis center 120 includes a plurality of clinician's computers 112b to 112d, which are connected to a clinician's network server 114, which communicates wirelessly with a router 106c, which is in wired communication with a modem 108c. Modems 108a to 108c communicate with each other via an internet 116, wide area network ("WAN") or local area network ("LAN").

Figure 15B:
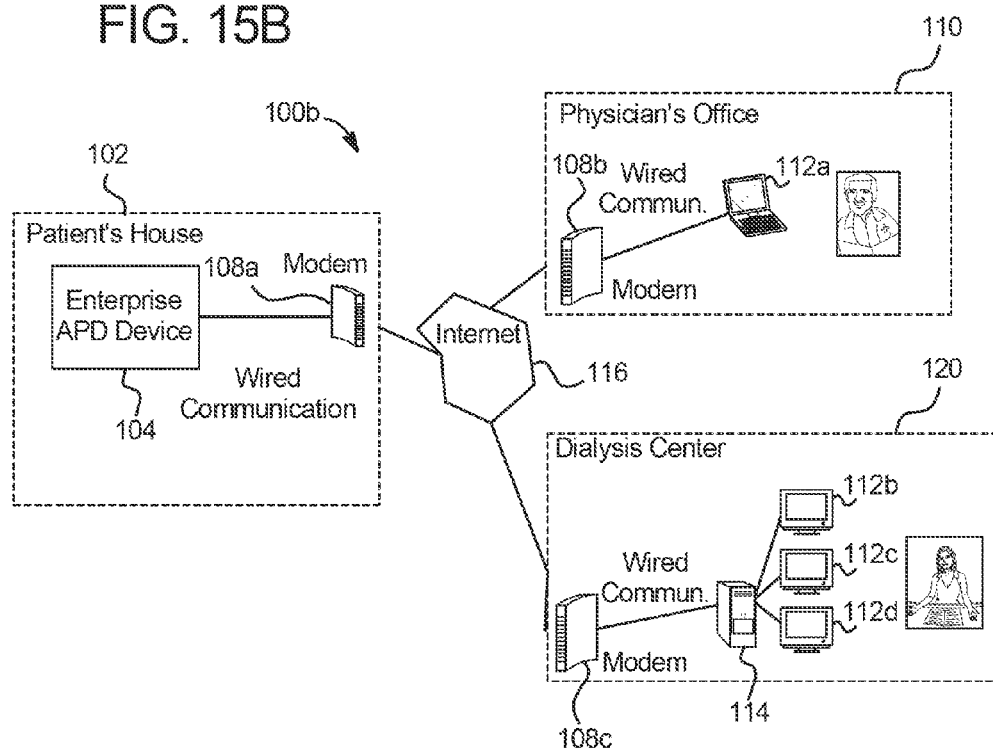

FIG. 15B illustrates an alternative wired network 100b or communication module 20 (FIG. 1) for communicating the PET, regimen generation, prescription filtering, inventory tracking, trending and prescription modification information (below) between patient 102, doctor 110 and dialysis center 120. Here, the patient 102 includes a dialysis instrument 104, which is in wired communication with modem 108a. The doctor 110 operates the doctor's (or nurse's) computer 112a (which could also be connected to a network server), which is in wired communication with a modem 108b. The dialysis center 120 includes a plurality of clinician's computers 112b to 112d, which are in wired communication with a modem 108c. Modems 108a to 108c again communicate with each other via an internet 116, WAN or LAN.

In one embodiment, the data points for curve 30 of FIG. 3 are generated at instrument 104 and sent to either the doctor 110 or the dialysis center 120 (most likely dialysis center 102), which houses the software to fit curve 30 to the data points. The patient then travels to the dialysis center 120 to have the blood work performed and to complete the PET as discussed herein. The software configured to run the PET and regimen generation screens of FIGS. 4A, 4B, 5A, 5B and 6 can be stored on clinician's server 114 (or individual computers 112b to 112d) of clinic 120 or computers 112a of doctor 110 (most likely clinic 120) of system 100a or 100b. Likewise, software configured to run the filtering and prescription optimization screens of FIGS. 6A to 6C, 7A, 7B, 8A to 8C and 9A to 9E can be stored on server 114 (or individual computers 112b to 112d) of clinic 120 or computers 112a of doctor 110 of system 100a and 100b.

In one embodiment, dialysis center 120 runs the PET, generates the regimens and filters the prescriptions. Dialysis center 120 via network 100 (referring to either or both networks 100a and 100b) sends the prescriptions to doctor 110. The filtering can be performed with input from the patient via either network 100, telephone or personal visit. The doctor reviews the prescriptions to approve or disapprove. If the doctor disapproves, the doctor can send additional or alternative filtering criteria via network 100 back to dialysis center 120 to perform additional filtering to optimize a new set of prescriptions. Eventually, either dialysis center 120 or doctor 110 sends approved prescriptions to instrument 104 of patient 102 via network 100. Alternatively, dialysis center 120 or doctor 110 stores the approved prescriptions and instrument 104 and on a given day queries dialysis center 120 or doctor 110 over network 100 to determine which prescription to run. The prescriptions can further alternatively be transferred via a data card.

In an alternative embodiment, dialysis center 120 runs the PET and generates the regimens. Dialysis center 120 via network 100 sends the regimens to doctor 110. The doctor reviews the regimens and filters same until arriving at a set of prescriptions to approve or disapprove. The filtering can again be performed with input from the patient via either network 100, telephone or personal visit. If the doctor disapproves, the doctor can perform additional filtering to optimize a new set of prescriptions. Here, doctor 110 sends approved prescriptions to instrument 104 and of patient 102 via network 100. Alternatively, doctor 110 stores the approved prescriptions and instrument 104 on a given day queries doctor 110 over network 100 to determine which prescription to run. Further alternatively, doctor 110 sends the approved prescriptions to dialysis center 120 over network 100, the dialysis center stores the approved prescriptions, and instrument 104 on a given day queries dialysis center 120 over network 100 to determine which prescription to run.

As discussed above, dialysis center 120 is likely in a better position to handle the inventory tracking module or software 18 than is doctor 110. In one embodiment therefore, dialysis center 120 stores the software configured to run the inventory tracking screens of FIGS. 10 to 13. Dialysis center 120 communicates with dialysis instrument 104 and patient 102 via network 100 to control the inventory for the patient's approved prescriptions.

Figure 16A:
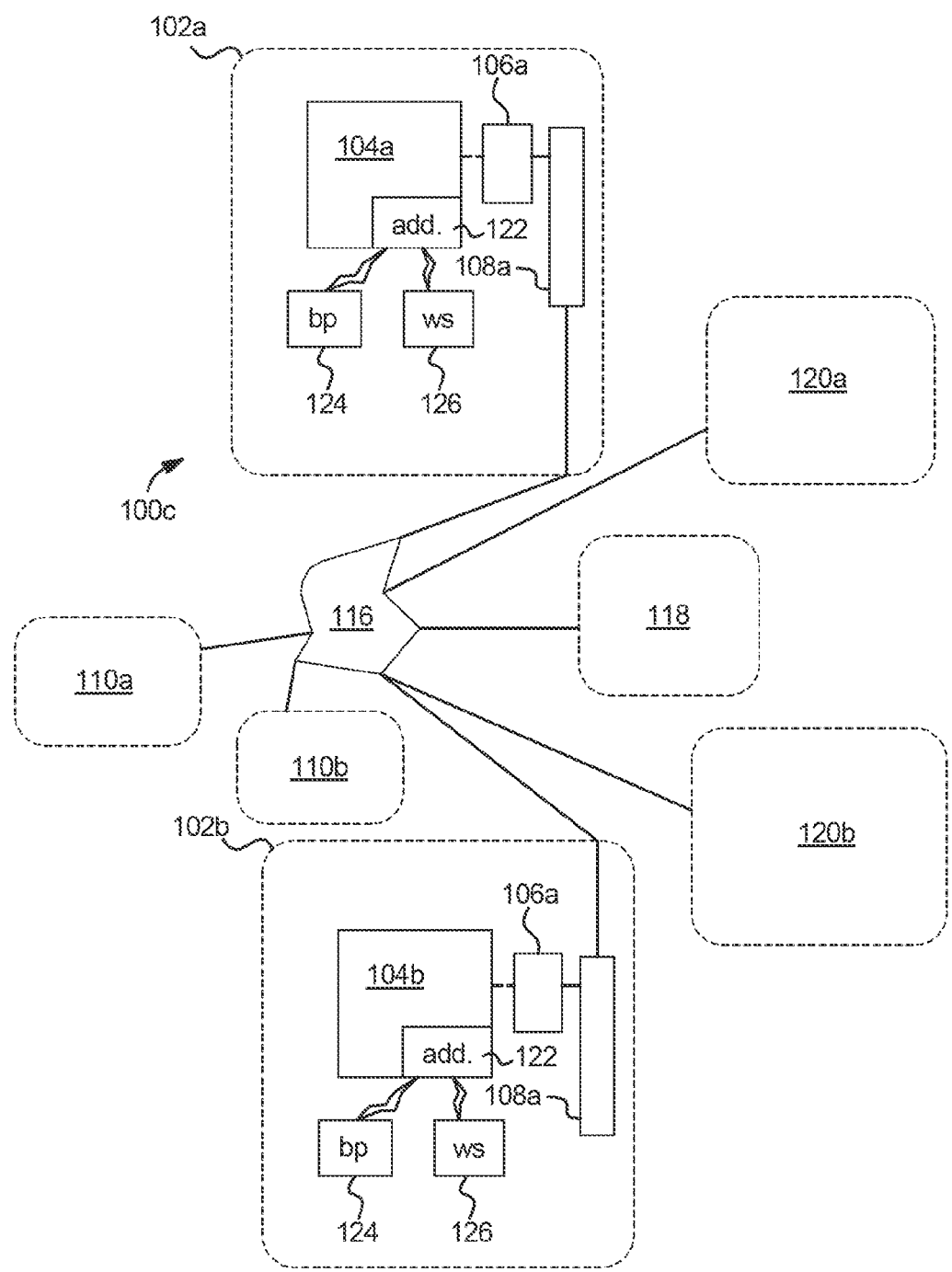
FIG. 16A is a schematic view illustrating another embodiment for a communications module and an embodiment of the data collection module, which includes wireless weight and blood pressure data entry for the prescription optimization system of the present disclosure.

Referring now to FIG. 16A, network 100c illustrates a further alternative network or communication module 20 (FIG. 1). Network 100c also illustrates the patient data collection module 22 of FIG. 1. It should be appreciated that the patient data collection principles discussed in connection with network 100c are also applicable to networks 100a and 100b. Network 100c includes a central clinical server 118, which could be stored in one of the dialysis centers 120, one of the doctor's offices 110 or at a separate location, such as at a facility run by the provider of system 10. Each of patients 102a and 102b, doctors 110a and 110b and dialysis centers 120a and 120b communicates with clinical server 118, e.g., via internet 116. Clinical server 118 stores and runs the software associated with any of the PET, regimen generation, prescription filtering, inventory tracking, trending and prescription modification (below) modules and facilitates communication between patients 102a/102b, doctors 110a/110b and dialysis centers 120a/120b.

Clinical server 118 in one embodiment receives the PET data from one of the dialysis centers 120 (referring to either of centers 120a or 120b) and sends it to clinical server 118. The UF data points of FIG. 3 can be sent to clinical server 118 either directly from patient 102 (referring to either of patients 102a or 102b) or from dialysis center 120 via patient 102. Clinical server 118 fits curve 30 (FIG. 3) to the data points and generates the regimens and either (i) filters the regimens (perhaps with patient input) into optimized prescriptions for the doctor 110 (referring to either of doctors 110a or 110b) to approve or disapprove or (ii) sends the regimens to doctor 110 to filter into optimized prescriptions (perhaps with patient input).

In either case, the approved prescriptions may or may not be sent to an associated dialysis center 120. For example, if the associated dialysis center 120 runs inventory tracking module 18 of system 10, the dialysis center 120 needs to know the prescriptions to know which solutions and supplies are needed. Also, if system 10 is operated such that the patient's dialysis instrument 104 (referring to either instrument 104a or 104b) queries the dialysis center 120 on a given day for which prescription to run, the dialysis center 120 needs to know the prescriptions. Alternatively, the patient's dialysis instrument 104 queries clinical server 118 daily for which prescription to run. It is also possible for clinical server 118 to run inventory tracking module 18 of system 10, in which case the associated dialysis center 120 can be relegated to obtaining the PET data.

Clinical server 118 can be a single server, e.g., a national server, which is a logical geographical boundary because different countries have different sets of approved dialysis solutions. If two or more countries have the same approved set of dialysis solutions and a common language, however, clinical server 118 could service the two or more countries. Clinical server 118 can be a single server or have spoke and hub links between multiple servers.

Figure 16B:
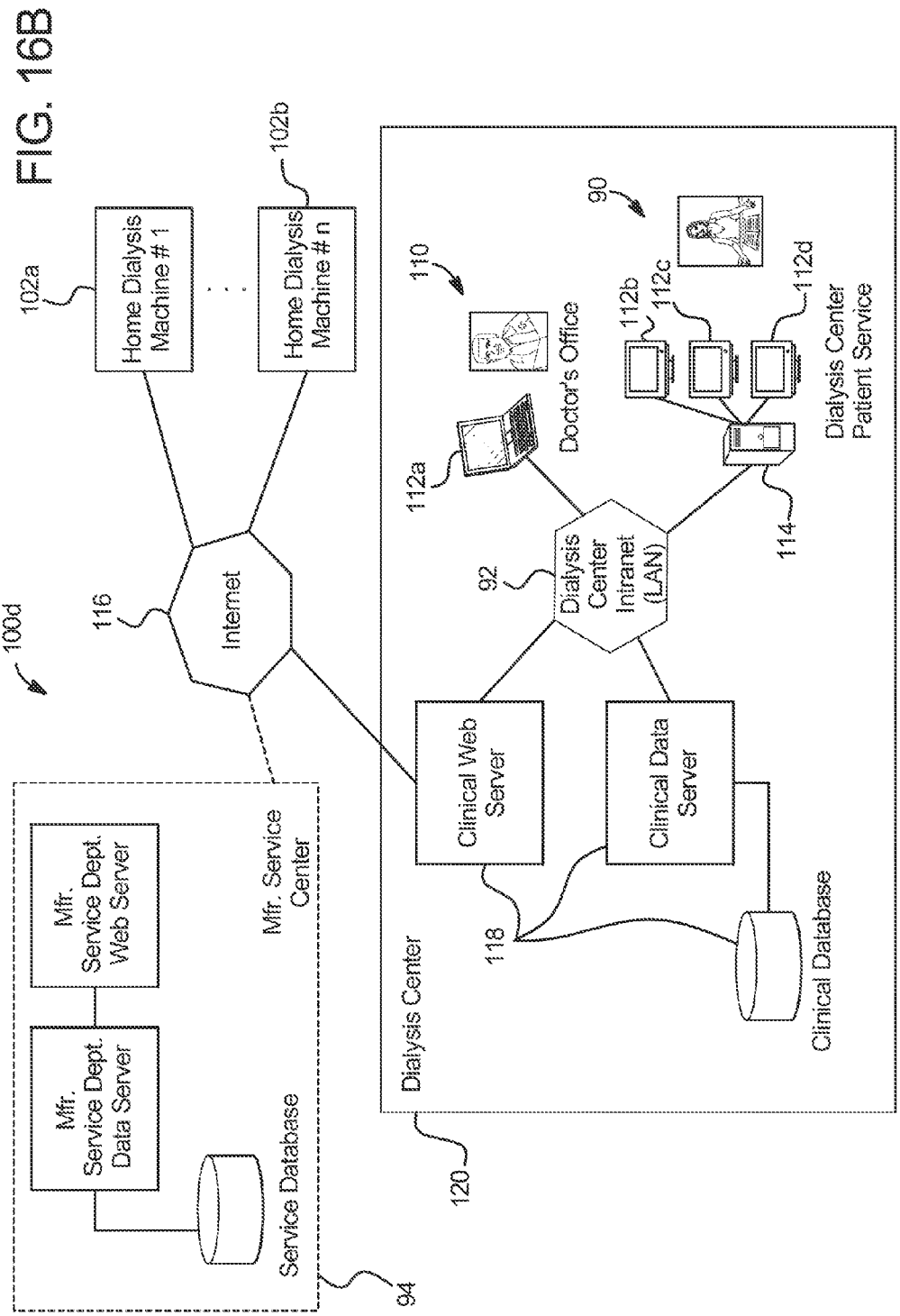
FIG. 16B is a schematic view illustrating a further embodiment for a communications module, in which a central clinical server is located at or associated with a particular dialysis center.

Referring now to FIG. 16B, network 100d includes a central clinical server 118, which is housed at or close to one of the dialysis centers 120. The dialysis center 120 houses a doctor's office 110 and a patient service area 90, each including one or more computer 112a to 112d. Patient service area 90 includes a server computer 114, which communicates with clinical server 118 in one embodiment via a local area network ("LAN") 92 for the dialysis center 120. Clinical server 118 in turn includes a clinical web server that communicates with internet 116 and LAN 92, a clinical data server that communicates with LAN 92 and a clinical database that interfaces with the clinical data server.

Each of patients 102a and 102b communicates with clinical server 118, e.g., via internet 116. Clinical server 118 stores and runs the software associated with any of the PET, regimen generation, prescription filtering, inventory tracking, trending and prescription modification (below) modules and facilitates communication between patients 102a/102b, doctors 110 and dialysis centers 120. Other dialysis centers 120 can communicate with center-based clinical server 118 with internet 116. Any of systems 100a to 100d can also communicate with an APD machine manufacturer's service center 94, which can include for example a service database, a database server and a web server. Manufacturer's service center 94 tracks machine problems, delivers new equipment, and the like.

Data Collection Feature

PET module 12, regimen generation module 14 and prescription optimization or filtering module 16 output data that networks 100 (referring now additionally to networks 100c and 100d) use to run dialysis therapies. In this regard, the networks 114 and 118 of system 10 use results from analysis that have already been performed. As seen with network 100c, system 10 also generates real-time daily patient data, which is fed to a server 114 (of a center 120) or 118 for tracking and analysis. This real-time data, along with therapy parameter inputs and therapy target inputs make up the data collection module 22 (FIG. 1) of system 10.

Each dialysis machine 104 (referring to either or both machines 104a and 104b) includes a receiver 122 as illustrated in FIG. 16A. Each receiver 122 is coded with an address and a personal identification number ("PIN"). The patient is equipped with a blood pressure monitor 124 and a weigh scale 126. Blood pressure monitor 124 and weigh scale 126 are each provided with a transmitter, which sends patient blood pressure data and patient weight data, respectively, wirelessly to receiver 122 of dialysis machine 104.

The address and PIN ensure that the information from blood pressure monitor 124 and weigh scale 126 reaches the proper dialysis machine 104. That is, if machines 104a and 104b and associated blood pressure monitors 124 and weigh scales 126 are within range of each other, the addresses and PIN's ensure that the dialysis machine 104a receives information from the blood pressure monitor 124 and weigh scale 126 associated with dialysis machine 104a, while dialysis machine 104b receives information from the blood pressure monitor 124 and weigh scale 126 associated with dialysis machine 104b. The address and PIN also ensure that dialysis machines 104 do not receive extraneous data from unwanted sources. That is, if data from an unwanted source is somehow transmitted using the same frequency, data rate, and communication protocol of receiver 122, but the data cannot supply the correct device address and/or PIN, receiver 122 will not accept the data.

The wireless link between blood pressure monitor 124, weigh scale 126 and dialysis machine 104 allows the devices to be located conveniently with respect to each other in the patient's room or house. That is, they are not tied to each other via cords or cables. Or, blood pressure and weight data are entered into instrument 104 manually. The wireless link however also ensures that the blood pressure data and weight data, when taken, are transferred automatically to the dialysis machine 104. It is contemplated that the patient takes his/her blood pressure and weighs himself/herself before (during or directly after) each treatment to provide a blood pressure and weight data point for each treatment. Data collection module 22 is configured alternatively to have a wired connection between one or more of blood pressure monitor 124 and instrument 104 and weight scale 126 and instrument 104.

Another data point that is generated for each treatment is the amount of ultrafiltration ("UF") removed from the patient. All three data points, blood pressure, patient weight and UF removed, for each treatment can be stored in the memory of the dialysis machine 104, on a data card and/or be sent to a remote server 114 or 118. The data points are used to produce performance trends as described next.

Any one or combination of the processing and memory associated with any of the dialysis instrument 104, doctor's (or nurse's) computer 112, clinician's server 114, clinical web server 118 or manufacturer's service center 94 may be termed a "logic implementer".

Trending And Alert Generation

The trending analysis and statistics module 24 (FIG. 1) of system 10 as seen herein calculates short term and long term moving averages of daily UF and other patient data shown below. Monitoring actual measured daily UF, only, produces too much noise due to residual volume and measurement error of the dialysis instrument 104. The trending regimes of module or feature 24 therefore look at and trend daily data as well as data that is averaged over one or more period of time. Trending and Alert Generation Using Multiple Patient Parameters Trending module 24 in one embodiment uses the following equation to form the short term and long term moving averages: $UF_{ma}(n)=1/k*(UF(n)+UF(n-1)+UF(n-2) \ldots + UF(n-k))$. For the short term moving average, typical values for k can be, e.g., three to fourteen days, such as seven days. For the long term moving average, typical values for k can be, e.g., fifteen to forty-five days, such as twenty-eight days.

The difference between target UF and actual measured UF is set forth as:

$$\Delta UF = UF_{target} - UF_{ma}.$$

$UF_{target}$ is the physician prescribed UF, and $UF_{ma}$ is the moving average value of actual daily UF measured (either daily measured value or two to three days for short term moving average). $\Delta UF$ can be either positive or negative. When the absolute value of $\Delta UF/UF_{target}$ exceeds the alert threshold preset by physician, system 10 (either at the machine 104 level or via server 114/118) alerts the patient and the physician 110 and/or clinician 120, which can trigger prescription adjustment or other response as discussed below.

The alert threshold can account for UF anomalies so as not to make system 10 false trigger or be oversensitive to daily UF fluctuations, which can inherently be significant (e.g., due to measurement error and residual volume). The following equation illustrates an example in which system 10 requires a number of days of a certain UF deviation:

$$\delta(\text{alert generated}) = |\Delta UF/UF_{target}| > X\% \text{ for } Y \text{ days}.$$

X % can be preset by the physician or clinician, and a typical value may be thirty to fifty percent. Y can also be preset by either the physician or clinician, and a typical value may be three to seven days.

The next equation addresses the possibility of a patient skipping dialysis or the patient's UF being consistently much lower than the target UF:

$$\text{If } \delta = \sum_{i=1}^{q} \delta_i = \sum_{i=1}^{q} |\Delta UF/UF_{target}| \rangle P \% \text{ for } Q \text{ days}$$

P % can be preset by the physician or clinician, and a typical value may be 150% to 250%. Q can also be preset by the physician or clinician, and a typical value can be two to three days. The above equation calculates a difference between the daily measured UF and the target UF and expresses the difference as a percentage of the target UF to determine an error in the percentage. Then the error percentage is accumulated over several days, e.g., two to three (Q) days. If the accumulated errors exceeds the threshold (P %), system 10 will generate UF alerts. The following examples illustrate the above algorithm:

Example #1

P=150%, Q=3 Days

Day #1, patient skipped therapy, UF error=100%; Day #2, patient skipped therapy, UF error=100%; Day #3, patient performed therapy, UF error=10%; accumulated UF error=210%>150%, then it will generate alarm.

Example #2

P=150%, Q=3 Days

Day #1, patient skipped therapy, UF error=100%; Day #2, patient performed therapy, UF error=20%; Day #3, patient performed therapy, UF error=10%; accumulated UF error=130%<150%, no alarm will be generated.

FIGS. 17 to 21 show trending screens 128, 132, 134, 136 and 138, respectively, which can be displayed to the patient on a display device 130 of the dialysis instrument 104 and/or on a computer monitor at doctor 110 or dialysis center 120. It is contemplated to generate the trends at any of these locations as needed. The main trending screen 128 of FIG. 17 allows the patient for example to select to see: (i) pulse and pressure trends; (ii) recent therapy statistics; (iii) UF trends; and (iv) weight trends. The patient can access any of the screens via a touch screen input, via a membrane or other type of switch associated with each selection, or via knob or other selector that allows one of the selections to be highlighted, after which the patient presses a "select" button.

Figure 18:
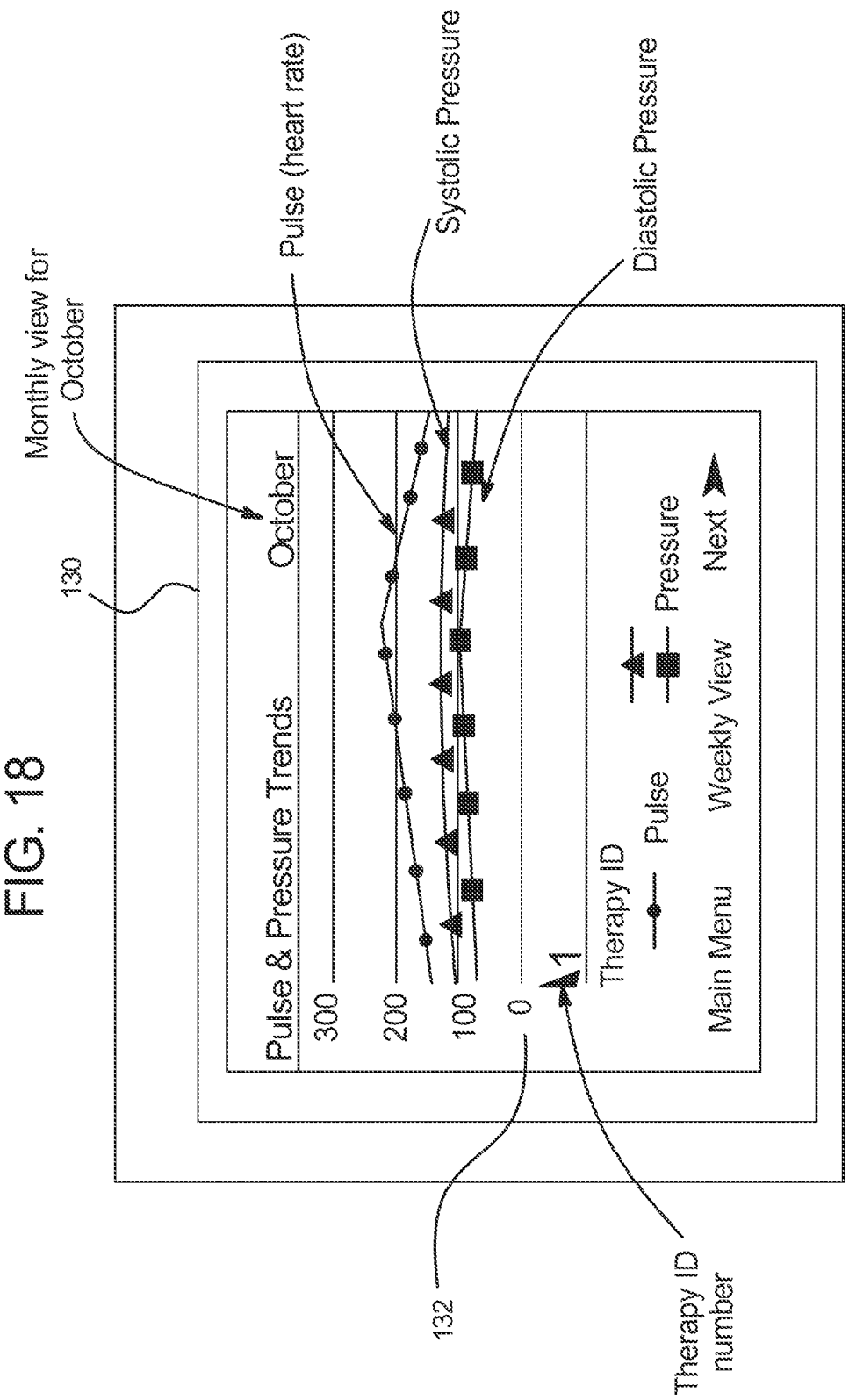

When the patient selects the pulse and pressure trends selection of the main trending screen 128, display device 130 displays the pulse and pressure trends screen 132 of FIG. 18. Pulse (heart rate, line with •'s), systolic pressure (line with ▲'s), and diastolic pressure (line with ■'s) are shown for a one month time period in units of mmHg Selection options on the pulse and pressure trends screen 132 include (i) returning to the main trending screen 128, (ii) seeing weekly trends for pulse, systolic pressure, and diastolic pressure instead and (iii) advancing to the next trending screen 134. The one or more therapy performed during the trend period, namely, therapy number 1 (e.g., standard UF), is also shown.

Figure 19:
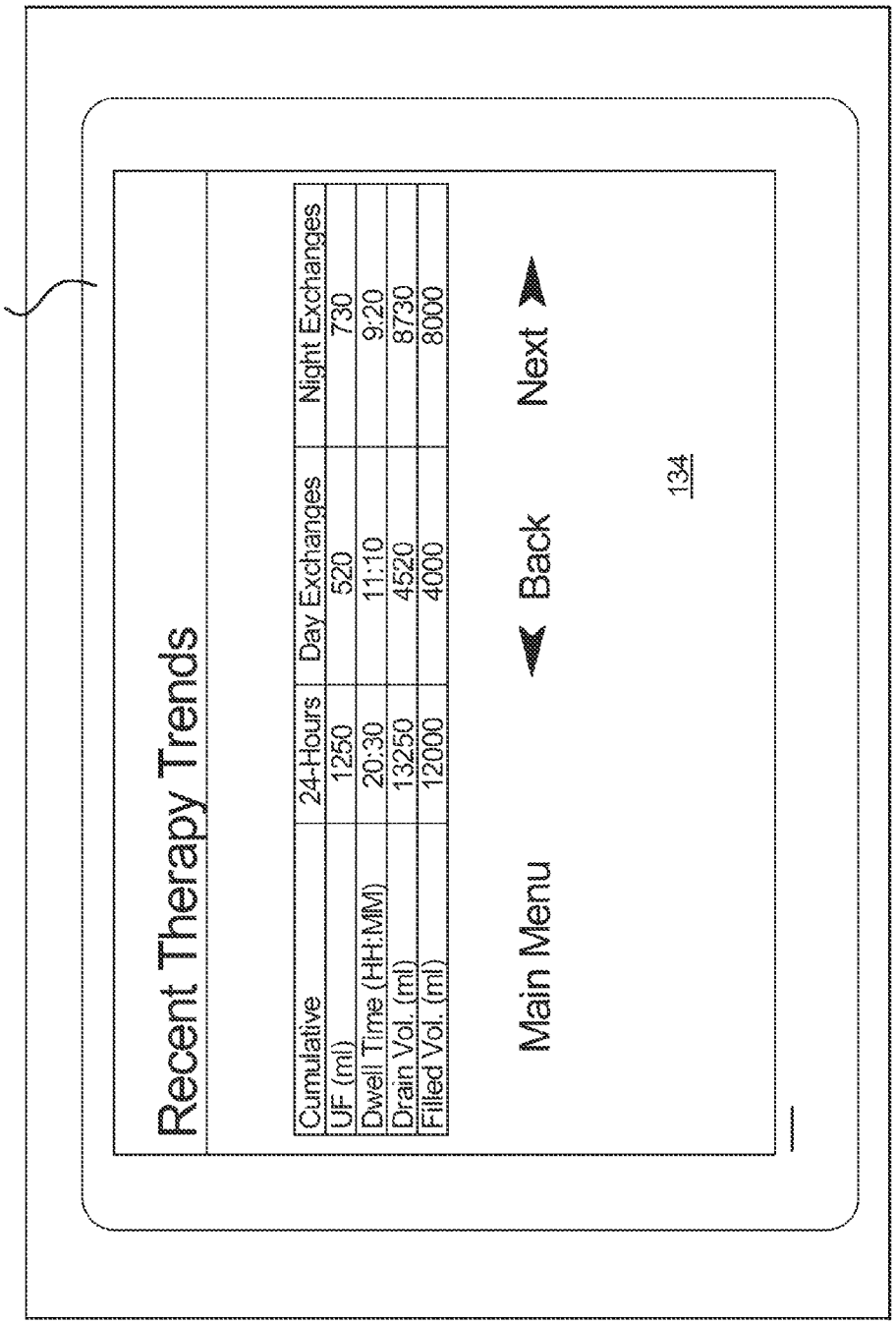

When the patient selects the next trending selection of the pulse and pressure trends screen 132, display device 130 displays a recent therapy trends or statistics screen 134 as seen in FIG. 19. FIG. 19 shows actual values for UF removed (in milliliters, including total UF and breakout UF's for day and night exchanges), cumulative dwell time (in hours, seconds, including total dwell and breakout dwells for day and night exchanges), drain volume (in milliliters, including total volume and breakout volumes for day and night exchanges), and filled volume (in milliliters, including total volume and breakout volumes for day and night exchanges). The recent therapy trends or statistics screen 134 as seen in FIG. 19 in one embodiment shows statistics from the previous therapy. Screen 134 alternatively includes a logs option that enables the patient to view the same information for prior therapies, e.g., therapies up to a month ago or since the download of the last set of prescriptions. Selection options displayed on the recent therapy trends or statistics screen 134 include (i) returning to the main trending screen 128, (ii) returning to the previous trending screen 132 and (iii) advancing to the next trending screen 136.

Figure 20:
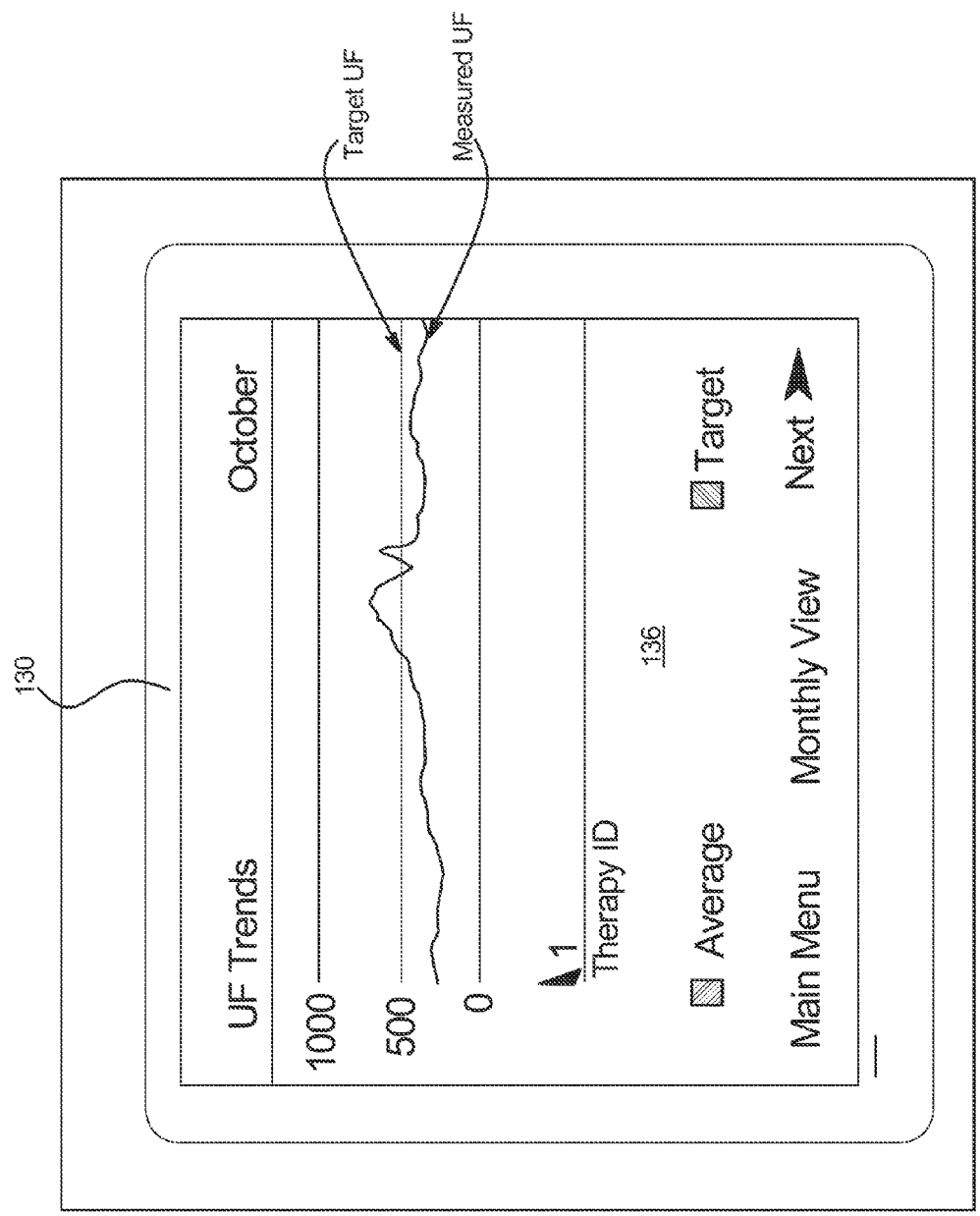

When the patient selects the next trending selection of the recent therapy trends or statistics screen 134, display device 130 displays a UF trends screen 136 as seen in FIG. 20. UF trends screen 136 shows a target UF line and a measured UF line for a one month time period in units of milliliters. Selection options on the UF trend screen include (i) returning to the main trending screen 128, (ii) seeing weekly trends for UF, monthly trends for UF or even three month trends for UF as long as the data is available, and (iii) advancing to the next trending screen 138. The therapy performed during the UF trending period is also shown.

Figure 21:
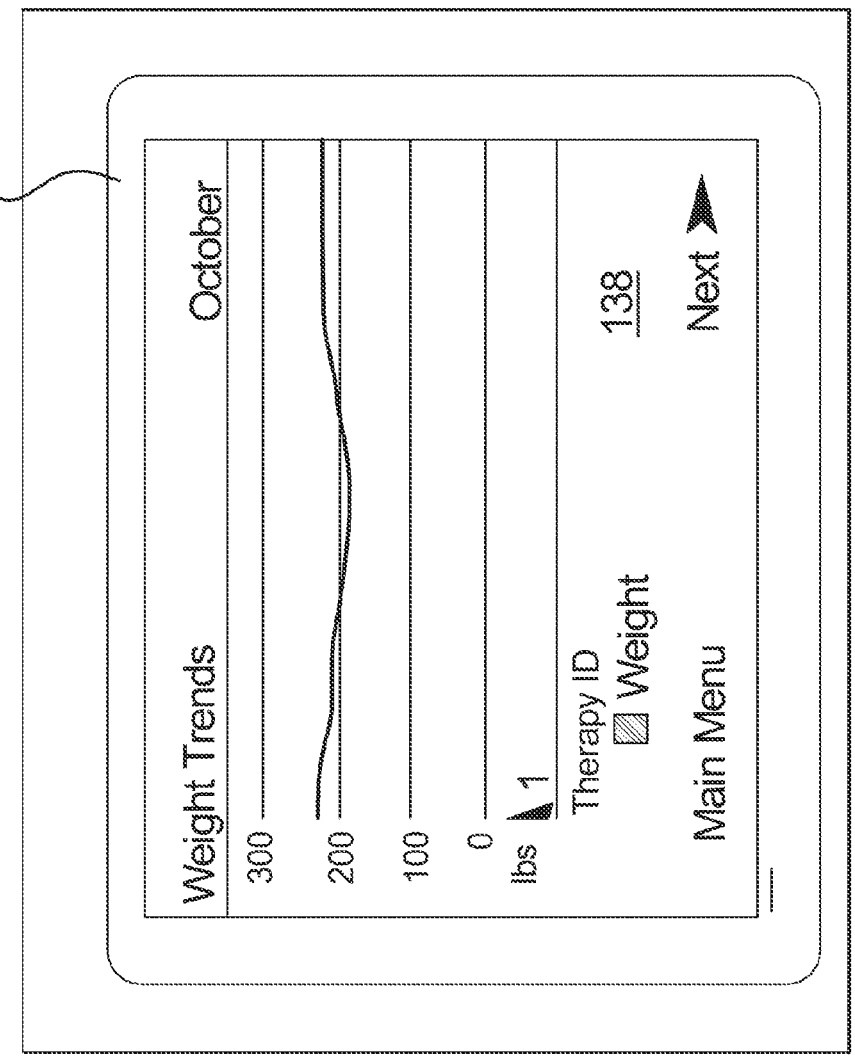

When the patient selects the next trending selection of the recent UF trends screen 136, display device 130 displays a patient weight trends screen 138 as seen in FIG. 21. Patient weight trends screen 138 shows a measured body weight ("BW") line for a one month time period in units of pounds. Selection options on the patient weight trend screen 138 include (i) returning to the main trending screen 128 and (ii) advancing to a next screen. The therapy performed during the BW trending period is also shown.

Figure 22:
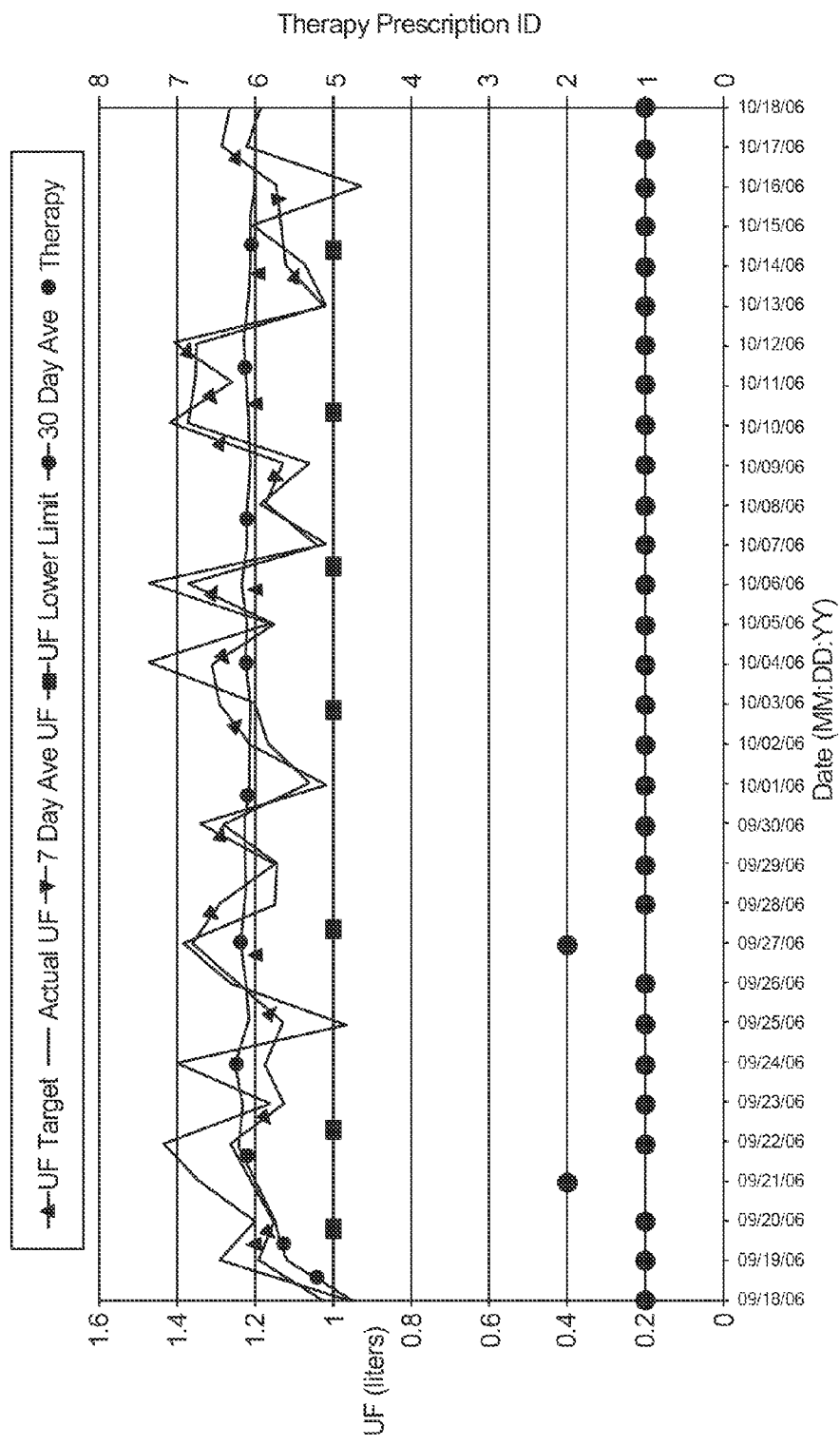
FIGS. 22 and 23 are sample screens displayed on a patient's dialysis instrument or a clinician's and/or doctor's computer as part of the trending module of the present disclosure, illustrating various trending data including moving UF averages, target UF, daily UF, UF limits and prescription used.
Figure 23:
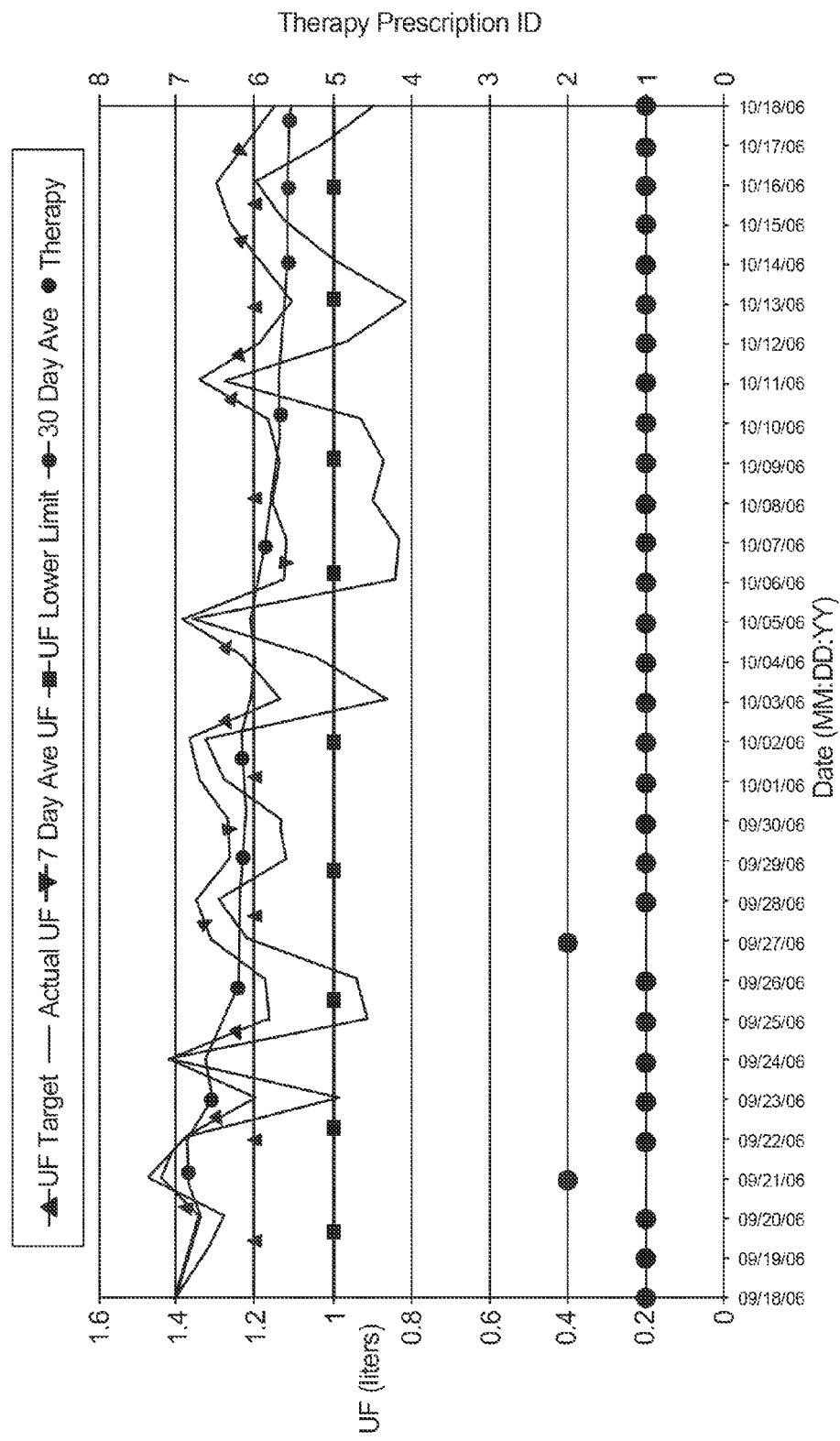

Alternative trending charts of FIGS. 22 and 23 display actual days on the x-axis. These trends could be reserved for the doctor 110 and/or dialysis center 120 or be accessible additionally by the patient, meaning that the alerts can be generated from the APD device 104 to the doctor and/or clinician or from a server computer to the doctor, clinician and/or patient. The trending charts of FIGS. 22 and 23 show the expected UF value or UF target for the patient based upon the patient's last PET results. If the difference between expected PET UF and the actual UF increases beyond a value that the doctor or clinician determines is significant, the clinician can order a new PET with or without lab work. That is, the patient can perform the UF portion of the PET as described in connection with FIGS. 2 and 3 and bring the drain volumes to the dialysis center 120. U.S. patent application Ser. No. 12/128,385, entitled "Dialysis System Having Automated Effluent Sampling And Peritoneal Equilibration Test", filed May 28, 2008, the entire contents of which are incorporated herein by reference, discloses an automated PET, which results in effluent samples that the patient can bring to the dialysis center 120 so that the samples can be analyzed for urea clearance, creatinine clearance, etc.

The trending charts of FIGS. 22 and 23 also show which therapy prescription was used on a given day, as seen at the right side of the figures (assuming for example that therapy prescription Zero is low UF, therapy prescription One is standard UF and therapy prescription Two is high UF). As seen in FIGS. 22 and 23, the standard UF prescription is performed on all but two days in which the high UF prescription is performed. In FIG. 22, the thirty day moving average (line with •'s) in particular shows that, generally, the patient's treatment is meeting the UF goal. In FIG. 23, the thirty day moving average (line with •'s) shows that after about Oct. 2, 2006, the patient's treatment started to not meet the UF goal and became progressively worse. Moreover, the entire thirty day trend line for October, 2006 slopes towards less and less UF removal. A skilled clinician here will see such trend as potentially being due to a loss of the patient's renal function and either (in conjunction with a doctor) order a new PET, provide new prescriptions or put the patient's UF performance on a close watch to see if the trend continues. The clinician/doctor could alternatively prescribe that the high UF prescription be performed more frequently in an attempt to reverse the negative-going UF trend.

As alluded to above, the doctor or clinician likely does not want to be notified when a single day falls below the lower limit. The UF data therefore needs to be filtered. The filter for example considers all three of daily UF values, the seven day rolling average UF (line with ▼'s) and the thirty day rolling average (line with •'s) in an algorithm to determine if the patient's prescription needs to be modified. The filter can also consider which therapies are being performed. For example, alert notification can occur sooner if the patient runs a high percentage of High UF therapies and is still failing to meet standard therapy UF targets.

One specific example of an alert algorithm is: the thirty day rolling average UF (line with •'s) has fallen by ten percent, and the actual UF (base line) has been below the lower limit for three of the past seven days while performing either the standard UF prescription or the high UF prescription. Another specific example of an alert algorithm is: the thirty day rolling average UF (line with •'s) has fallen by ten percent and the seven day rolling average UF (line with ▼'s) has fallen below the lower limit LCL, while performing either the standard UF of the high UF therapies.

The alert algorithm can also take into account daily weight and blood pressure data. For example, when the UF deviation, daily blood pressure and body weight each exceed a respective safety threshold, an alert is triggered. In one specific example, system 10 alerts if (i) UF deviates from the target UF; and (ii) short term moving average (e.g., three to seven days) body weight ("BW") is greater than a threshold; and (iii) short term moving average (e.g., three to seven days) systolic/diastolic blood pressure ("BP") is greater than a threshold. BP and BW thresholds are preset by physician 110.

Further, body weight data alone can trigger an alarm when for example the patient is gaining weight at a certain rate or gains a certain amount of weight. Here, system 10 can notify the doctor 110 and/or clinician 120, prompting a call or electronic mail to the patient asking for an explanation for the weight gain. If the weight gain is not due to diet, it could be due to an excessive amount of dextrose in the patient's prescription, such that a new lower dextrose prescription or set of such prescriptions may need to be prescribed. For example, clinician 120 can set the patient's target body weight, and if the daily measured body weight is off by Xw pounds for Yw days in a seven day period, body weight gain is considered excessive and an alert is triggered:

$$\Delta BW = BW_m - BW_{target} > Xw \text{ for } Yw \text{ days,}$$

where
$BW_m$ is the measured daily body weight, $BW_{target}$ is the target body weight (set by doctor 110 or clinician 120), Xw is a limit of body weight exceeding the target (set by doctor 110 or clinician 120), and Yw is the number of days (set by doctor 110 or clinician 120).

Likewise, an increase in blood pressure alone could prompt a communication from the doctor 110 and/or clinician 120 for an explanation from the patient. It is further contemplated to trend the patient's daily bio-impedance, especially as such sensing comes of age. A bio-impedance sensor can for example be integrated into a blood pressure cuff (for wired or wireless communication with dialysis instrument 104), so that such sensing does not inconvenience the patient. System 10 uses bio-impedance in one embodiment to monitor the dialysate patient hydration state by estimating the patient's intra and extra-cellular water. Such data aids the patient and clinician in selecting a therapy (e.g., high UF when patient is over hydrated and low UF patient is dehydrated). Bio-impedance can thereby help to control the patient's fluid balance and blood pressure.

The clinician in the main is concerned about two factors: therapy effectiveness and patient compliance. Patients whose UF is below target because they are running a low UF therapy too often, or are skipping therapies, need to be told in a timely manner to change their behavior. Patients whose UF is below target but who are fully compliant and may even be performing high UF therapies to obtain their target UF may need to have their prescription(s) changed in a timely manner. The trends of FIGS. 22 and 23 provide all such information to the clinician.

System 10 knows accordingly if the lower than expected UF is due to compliance issues or potential therapy prescription issues. In an embodiment in which the patient chooses to pick which prescription to run on a given day, the dialysis instrument 104 can be programmed to provide a warning to the patient when the patient runs the low UF prescription too often (low UF prescription may be less demanding than standard UF prescription). The programming can be configured to escalate the warnings if the patient continues with this behavior, let the patient know that the dialysis center 120 is being notified, and notify the dialysis center accordingly. The instrument 104 can likewise be programmed to warn the patient if the patient skips too many treatments and notify the dialysis center 120 if the missed treatments continue. Here, the warning and notification can be made regardless of whether the patient picks the prescription to run or the machine 104/clinic 120 chooses the prescriptions on a given day.

Figure 24:
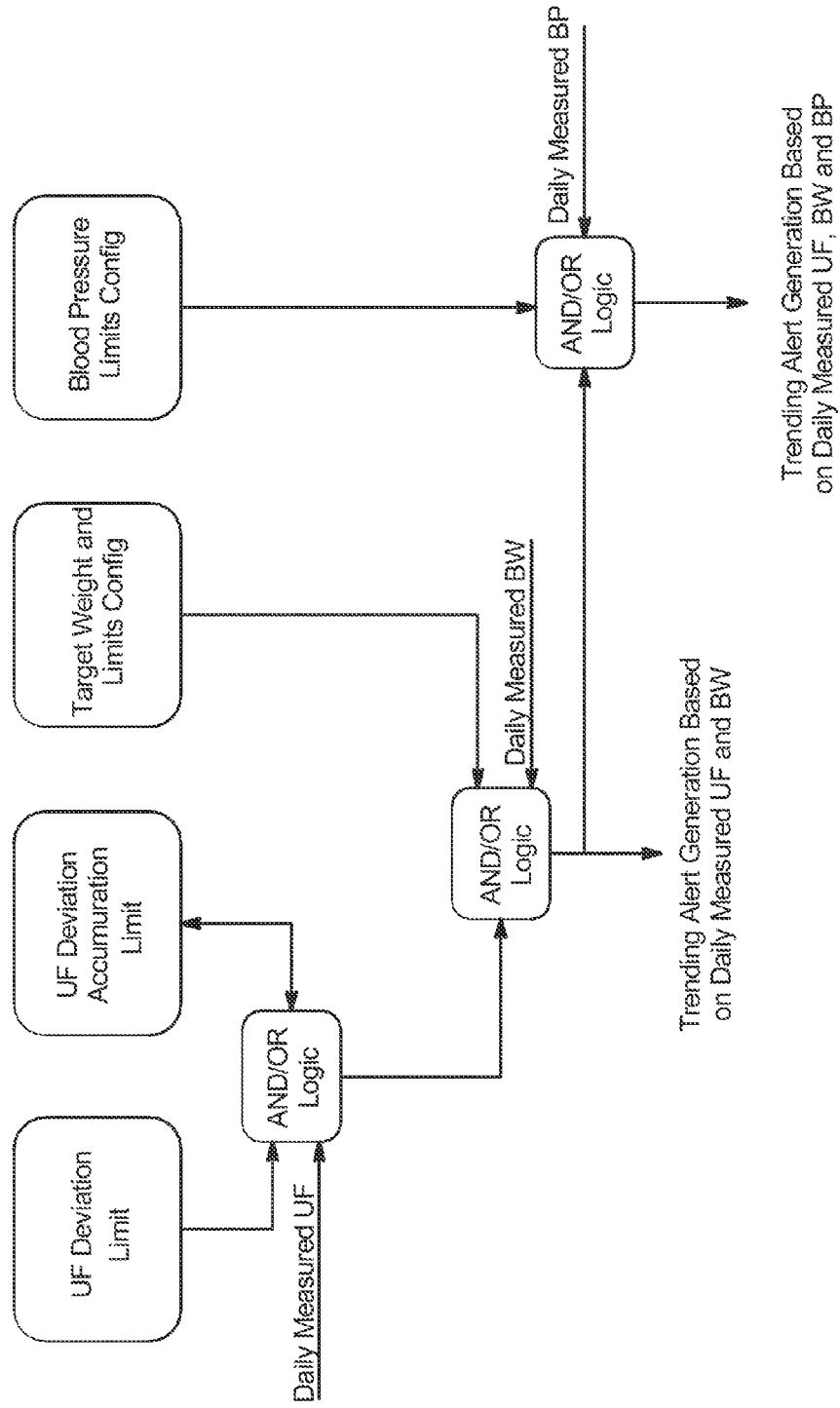
FIG. 24 is a schematic diagram illustrating one possible alert generation algorithm for the trending and alert generation module of the prescription optimization system of the present disclosure.

FIG. 24 summarizes the options available for setting simple or complex alert generation logics. The parameters that could be monitored include (on the top row): (i) daily UF deviation limit, (ii) UF deviation accumulation limit, (iii) body weight target and (iv) blood pressure limit. The middle logic operators show that using one or more of (a) measured daily UF, (b) measured daily body weight, and (c) measured daily blood pressure, the limits of the top row can be combined in different combinations using "AND" logic "OR" Boolean logic to determine when to send an alert to the patient, doctor or clinician. The illustrated, alerts are based on (i) UF and BW or (ii) UF, BW and BP. An alert can be based on UF alone, however.

Figure 25:
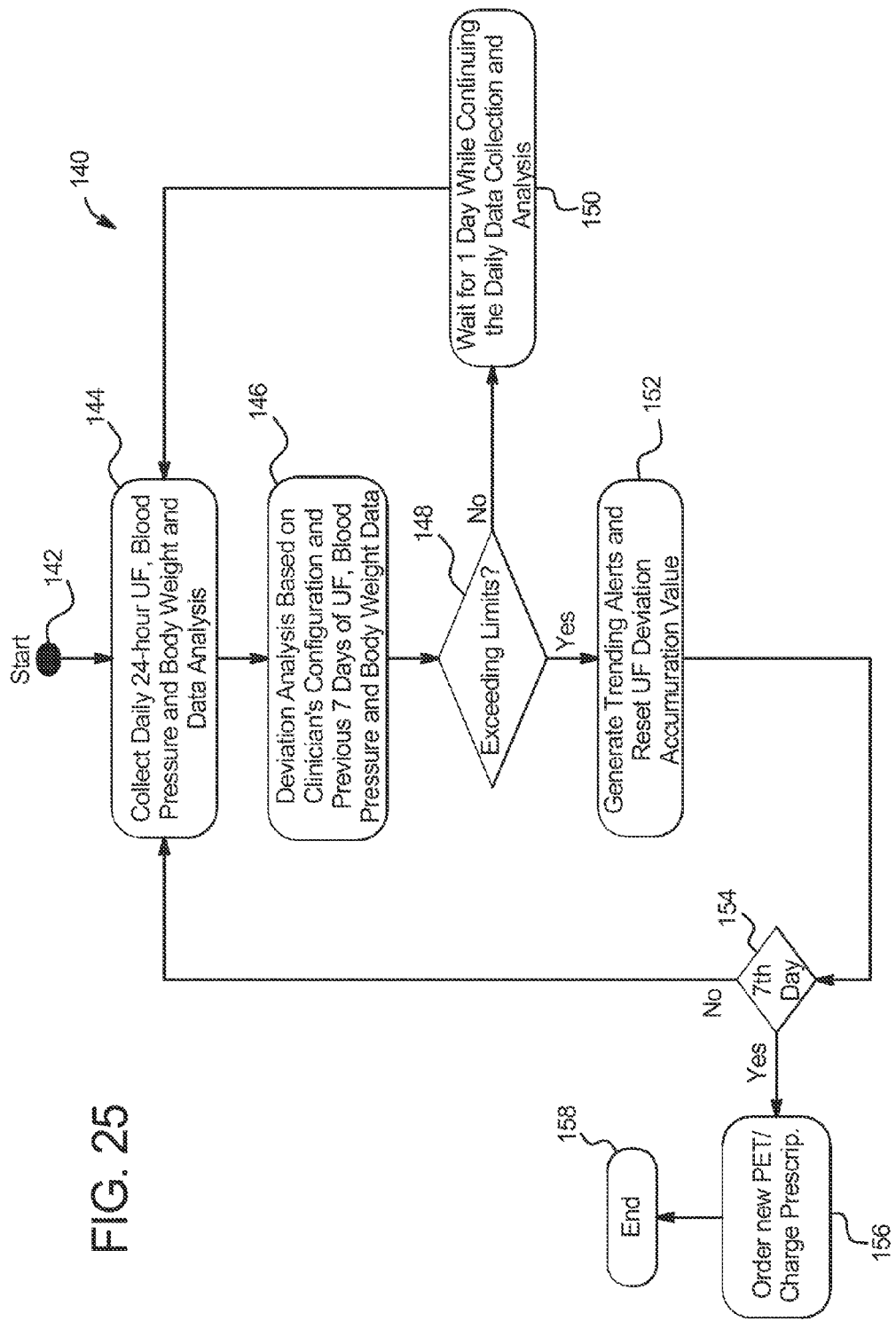
FIG. 25 is a logic flow diagram illustrating another possible alert generation/prescription modification algorithm for the trending and alert generation module of the prescription optimization system of the present disclosure.

Referring now to FIG. 25, algorithm or action flow diagram 140 shows one alternative alert sequence for system 10. Upon starting at oval 142, system 10 collects daily UF, BP, and BW data at block 144. At block 146, deviation analysis is performed, e.g., based on doctor/clinician settings and rolling averages for UF, BP and BW. At diamond 148, method or algorithm 140 of system 10 determines whether any of UF, BP, and BW is exceeding limits. If not, method or algorithm 140 waits for another day, as seen at block 150, and then returns to the collection step of block 144. If one or a combination of limits is exceeded at diamond 148, an alert is sent to the patient, clinician and/or doctor, as seen at block 152. Deviation and accumulated values are reset.

A hold or watch period is then started at diamond 154, e.g., for seven days, to see if the alert condition persists. During this period, it is contemplated that system 10 communicates between patient 104, doctor 110 and/or clinician 120 daily or otherwise regularly until the low UF trend is reversed. The clinician may make suggestions during this period, e.g., to try the high UF prescription or modify the patient's diet. As discussed, dialysis center 120 also receives trending data for patient weight and blood pressure in addition to the UF trending data. The mean arterial pressure ("MAP") may be the most appropriate value to trend relative to blood pressure. The clinicians evaluate the weight and MAP data concurrently during the low UF periods.

If the alert condition persists for a period, e.g., seven days as seen at diamond 154, method 140 and system 10 order a new PET and/or change the patient's prescription, as seen at block 156. Afterwards, method 140 ends as seen at oval 158.

Patient Case Studies

Patient A started peritoneal dialysis treatment just two months ago and still has residual renal function ("RRF"). His UF target is 800 mL/per day. The doctor set the alert watch to look at daily UF deviation, UF deviation accumulation and target body weight. Here, a deviation limit X was chosen to be 30%, for a period Y equal to four out of seven days. A three-day UF deviation accumulated error was chosen to be 150%. Target body weight was selected to be 240 pounds with a safety limit delta of +five pounds in seven days. The following table is an example of the measured daily twenty-four hour UF, BP and BW for a seven day period.

TABLE 5

| Patient A measured parameters | | | | | | | |
|---|---|---|---|---|---|---|---|
| Parameters | Sun | Mon | Tue | Wed | Thur | Fri | Sat |
| Daily UF (mL) | 600 | 650 | 700 | 600 | 550 | 750 | 730 |
| Daily Systolic/Diastolic Pressure (mmHg) | 150/90 | 148/95 | 160/97 | 153/88 | 165/98 | 170/95 | 160/92 |
| Daily Body Weight (LB) | 242.5 | 243.3 | 243.5 | 244.7 | 243.1 | 245.4 | 245.8 |
| Daily UF Deviation From Target UF | 25% | 19% | 13% | 25% | 31% | 6% | 9% |
| Daily UF Deviation Accumulated Error | — | — | 57% | 57% | 69% | 62% | 46% |
| Daily Body Weight Deviation from Target (LB) | 2.5 | 3.3 | 3.5 | 4.7 | 3.1 | 5.4 | 5.8 |

In the week of therapy shown above for Patient A, only Thursday's daily UF falls below the 30% lower limit threshold. The three-day accumulated UF deviation does not exceed 150%. The patient's body weight stays under limit (+five pounds) in all but the last two days. Here, system 10 does not generate an alert.

Patient B has been on PD for over two years. She is very compliant with her therapy and follows clinician's instructions strictly. She does not have any RRF and her daily UF target is 1.0 L. Here, the doctor 110 and/or clinician 120 set alert conditions as follows. A deviation limit X was chosen to be 20%, for a period Y equal to four out of seven days. A three-day UF deviation accumulated error was chosen to be 150%. Target body weight was selected to be 140 pounds with a safety limit delta of +five pounds in seven days. The following table is an example of the measured daily twenty-four hour UF, BP and BW for a seven day period.

TABLE 6

| Patient B measured parameters | | | | | | | |
|---|---|---|---|---|---|---|---|
| | Sun | Mon | Tue | Wed | Thur | Fri | Sat |
| Daily UF (mL) | 880 | 850 | 920 | 870 | 910 | 950 | 930 |
| Daily Systolic/Diastolic Pressure (mmHg) | 150/93 | 142/86 | 147/92 | 153/86 | 155/90 | 173/90 | 166/87 |
| Daily Body Weight (LB) | 143.5 | 144.3 | 143.8 | 144.3 | 143.1 | 144.6 | 144.8 |
| Daily UF Deviation From Target UF | 12% | 15% | 8% | 13% | 9% | 5% | 7% |
| Daily UF Deviation Accumulated Error | — | — | 35% | 36% | 30% | 27% | 21% |
| Daily Body Weight Deviation from Target (LB) | 3.5 | 3.3 | 3.8 | 4.3 | 3.1 | 4.6 | 4.8 |

In the week of therapy shown above for Patient B, none of the daily 24-hour UF values falls below the 20% lower limit threshold. The 3-day accumulated UF deviation does not exceed 150% on any day. The patient's weight never exceeds the threshold of +five pounds. Accordingly, system 10 does not generate a trending alert this week.

Patient C has been on PD for over a year. The patient sometimes over-eats/drinks and skips a therapy from time to time. He does not have any RRF and his daily UF target is 1.0 L. Here, the doctor 110 and/or clinician 120 set alert conditions as follows. A deviation limit X was chosen to be 25%, for a period Y equal to four out of seven days. A three-day UF deviation accumulated error was chosen to be 150%. Target body weight was selected to be 220 pounds with a safety limit delta of +five pounds in seven days. The following table is an example of his measured daily 24-hour UF, BP and WE for a seven day period.

TABLE 7

| Patient C measured parameters | | | | | | | |
|---|---|---|---|---|---|---|---|
| | Sun | Mon | Tue | Wed | Thur | Fri | Sat |
| Daily UF (mL) | 880 | 700 | 840 | 900 | 0 | 700 | 500 |
| Daily Systolic/Diastolic Pressure (mmHg) | 167/97 | 156/88 | 177/96 | 163/96 | 165/90 | 166/90 | 178/89 |
| Daily Body Weight (LB) | 223.5 | 225.3 | 223.8 | 224.3 | 225.1 | 225.6 | 225.8 |
| Daily UF Deviation From Target UF | 12% | *30%* | 16% | 10% | *100%* | *30%* | *50%* |
| Daily UF Deviation Accumulated Error | — | — | 58% | 56% | 126% | 140% | *180%* |
| Daily Body Weight Deviation from Target (LB) | 3.5 | *5.3* | 3.8 | 4.3 | *5.1* | *5.6* | *5.8* |

In the week of therapy shown above for Patient C, the patient's daily UF fell below the 25% threshold on Monday, Thursday, Friday and Saturday, as highlighted. The three-day accumulated UF deviation exceeded the 150% limit after Saturday's therapy. The patient also exceeds his+five pound weight limit four times, namely, on Monday, Thursday, Friday and Saturday. System 10 accordingly sends a trending alert after this week.

Trending and Alert Generation Using Statistical Process Control

Figure 26:
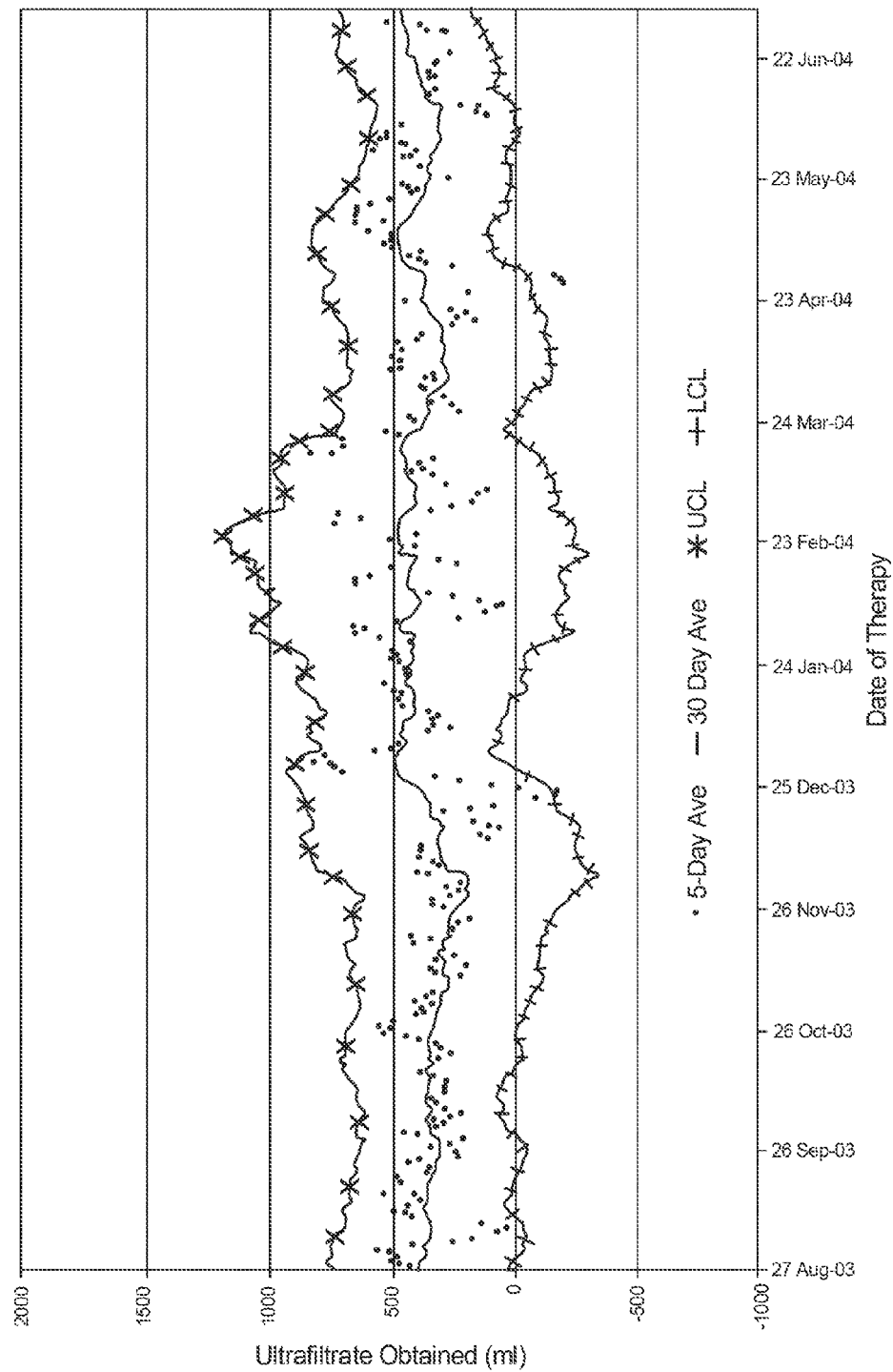
FIG. 26 is a sample screen displayed on a patient's dialysis instrument or a clinician's and/or doctor's computer as part of the system of the present disclosure, illustrating various trending data including moving UF averages and UF limits determined via statistical process control.

It is also contemplated to use statistical process control ("SPC") to identify instability and unusual circumstances. Referring now to FIG. 26, one example moving average or trend is shown, which shows a five-day average UF (dots) and an average UF for the previous thirty days (base middle line). A range is calculated to be the difference between the lowest and the highest UF values over the past thirty days. An upper control limit ("UCL", line with X's through it) for a given day is calculated to be:

$$UCL = \text{(the moving average for the given day)} + \text{(a constant, e.g., 0.577,*the range for the given day)}$$

and the lower control limit ("LCL", line with /'s through it) is calculated to be $$LCL = \text{(the moving average for the given day)} - \text{(the constant, e.g., 0.577,*the range for the given day)}.$$

FIG. 26 shows a UF trend created for a patient, e.g., from August 2003 through June 2004 using SPC. In December of 2003 and in April of 2004, the five day moving average UF (dots) fell below the LCL. System 10 could be configured to monitor the five day average and alert the patient, clinic and/or doctor when the five day moving average UF (dots) falls below the LCL (or falls below the LCL for a number of days in a row). The software configured to generate the trends can be located at the dialysis instrument 104 or at either server computer 114 or 118. In various embodiments, any one or more or all of the patient 102, dialysis center 120 or doctor 110 can access and view the trends. The trend data is generated whether or not the trend is actually viewed by anyone. The alerts are auto-generated in one embodiment, enabling system 10 to monitor patient 102 automatically for the dialysis center 120 and doctor 110.

Figure 27:
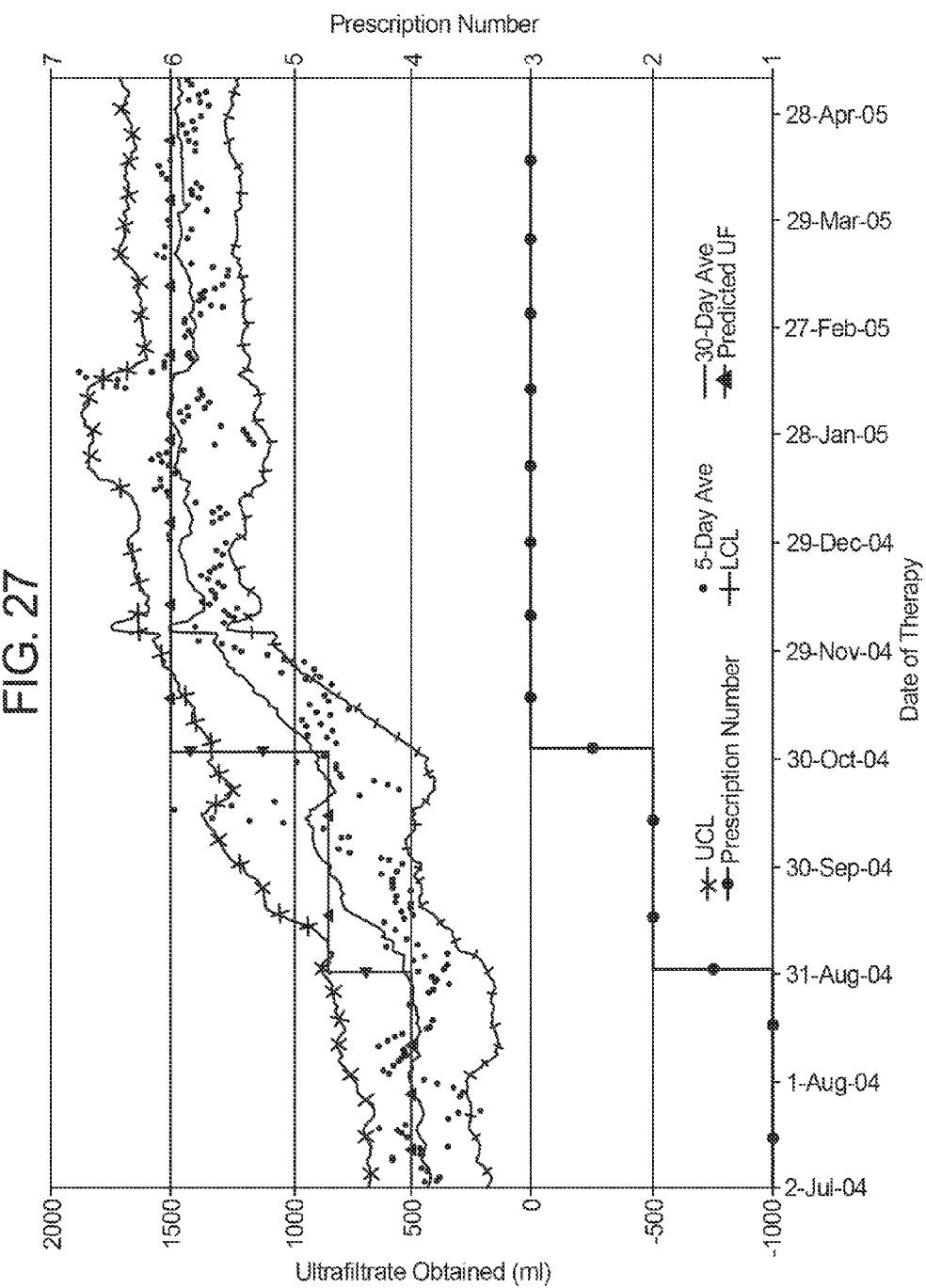
FIG. 27 is a sample screen displayed on a patient's dialysis instrument or a clinician's and/or doctor's computer as part of the system of the present disclosure, illustrating various trending data including moving UF averages, target UF, prescription used and UF limits determined via statistical process control.

FIG. 27 shows a second trend for the same patient after changes have been made to the patient's prescription (line with •'s). Here, the patient's daytime exchange has been changed from Nutrineal® dialysate to Extraneal® dialysate. FIG. 27 shows the difference a new prescription (line with •'s) had on the patient's UF starting in September of 2004 and again in November of 2004 when the patient's residual renal function tapered off.

The statistical process control alert algorithm can also take into account body weight ("BW") and/or blood pressure ("BP"). If UF has a normal distribution having a mean value of $\mu$ and standard deviation of $\sigma$ calculated based on time and population, and wherein C is an empirically determined constant. In most processes that are controlled using Statistical Process Control (SPC), at each time point, multiple measurements or observations are made (e.g. measure the room temperature multiple times at 8:00 AM), however in one embodiment of system 10, the SPC only one measurement is made at each time point, e.g., one UF measurement, one pressure and weight reading per day. System 10 could then alert if: (i) short term moving average (e.g., three to seven days) UF is outside the upper control limit ($UCL_{UF} = UF_{target}\square + C\sigma$) or lower control limit ($LCL_{UF} = UF_{target}\square - C\sigma$); or (ii) short term moving average (three to seven days) body weight>BW threshold; and/or (iii) short term moving average (three to seven days) systolic/diastolic BP>BP threshold.

FIG. 27 shows that the SPC trending charts can also display the expected UF value (line with ▲'s) for the patient based upon his/her last PET results. The thirty-day average line shows that actual UF, while lagging slightly behind expected UF (which is to be expected for a thirty day average) eventually aligns itself with the expected UF results. Here, the patient is not underperforming, he/she is able to meet target. The patient may be losing RRF, however, meaning the patient's prescription needs to be more aggressive for UF because the patient has increasing less ability to remove waste and excess water himself/herself. On the other hand, if the difference between expected UF and the actual UF increases beyond a value that the doctor/clinician determines is significant, e.g., below LCL for one or more day, the clinician/doctor can order a new PET as discussed above.

Prescription Recall and Modification

Figure 28:
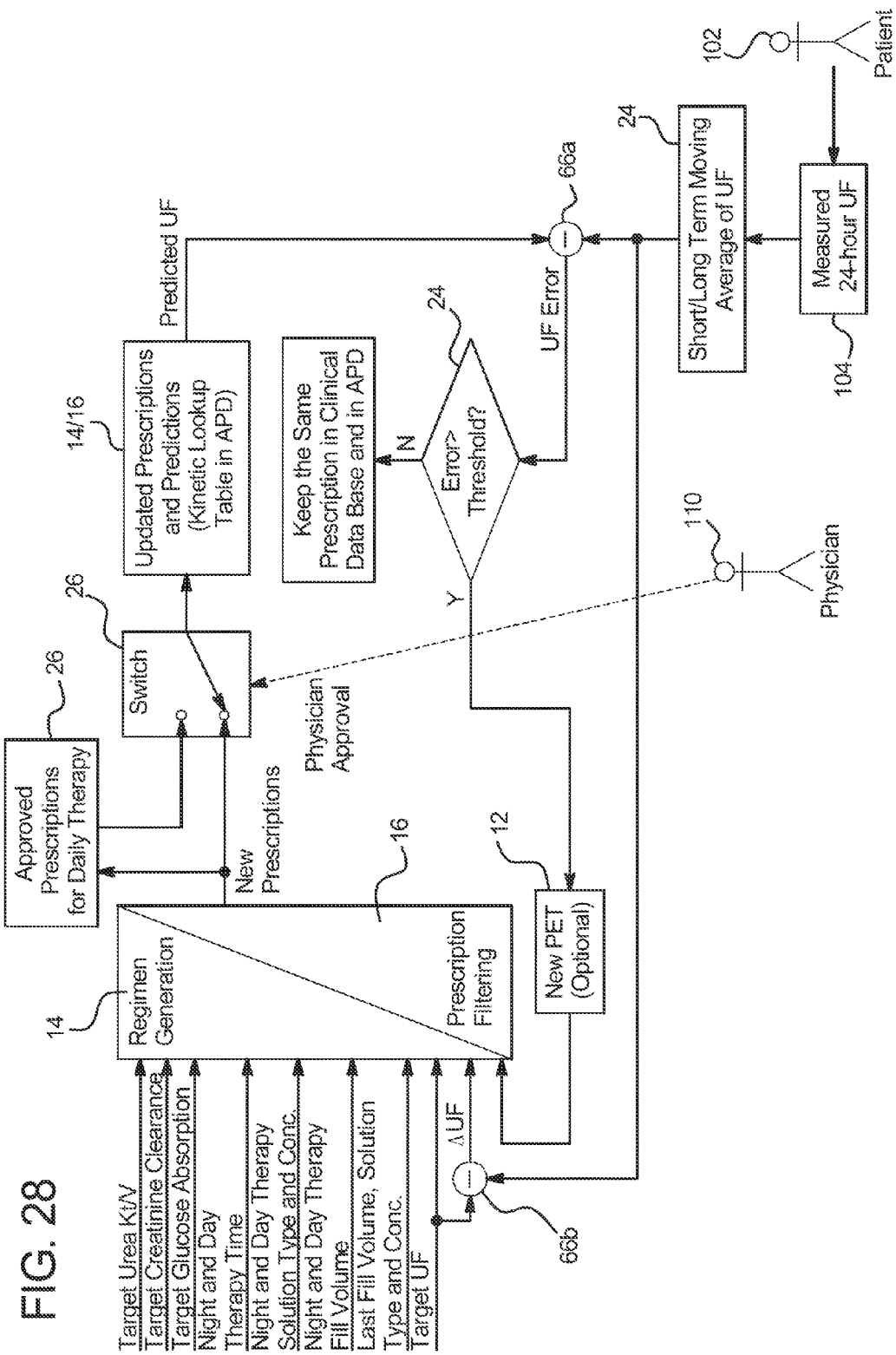
FIG. 28 is a schematic view of one embodiment of a transfer function used for the prescription recall and adjustment module of the prescription optimization system of the present disclosure.

System 10 also includes a prescription recall and modification feature 26 shown and described above in connection with FIG. 1. Referring now to FIG. 28, prescription recall and adjustment feature or module 26 is illustrated in more detail. Prescription recall and adjustment feature or module 26 relies on and interfaces with other features of system 10, such as the improved PET feature 12, regimen generation feature 14, prescription filtering feature 16, and trending an alert generation feature 24. As seen in FIG. 28, one aspect of prescription recall and adjustment feature or module 26 is the selection of one of the approved prescriptions for treatment.

Referring now to FIG. 29, a screen 160 of display device 130 of dialysis machine 104 illustrates one patient selection screen that allows the patient to select one of the approved prescriptions (standard, high and low UF) for the day's treatment. The type of input can be via membrane keys or here via a touch screen overlay, for which areas 162, 164 and 166 have been mapped into memory as standard UF prescription, high UF prescription and low UF prescription selections, respectively. System 10 in the illustrated embodiment allows the patient to select a prescription for each day's treatment. For example, if the patient has consumed more fluids than normal on a given day, the patient can run the high UF prescription. If the patient has worked out, been in the sun, or for whatever reason perspired a great deal during the day, the patient may choose to run the low UF prescription.

If the patient, e.g., patient viewing the therapy trend screens 134 and 136 above notices a drop in UF running the standard UF prescription, the patient may be empowered to choose to run the high UF prescription for a few days to see how the patient reacts to the prescription change. Presumably, daily UF will increase. But it should also be appreciated that the patient, clinician or doctor should check to see if the actual increased UF meets the increased expected UF due to the use of the high UF prescription. If the patient is underperforming for both prescriptions, it may be time for a new PET and possibly a new set of prescriptions.

Allowing the patient to adjust his/her therapy as described above is likely done only when the doctor or clinician has a comfort level with the patient that the patient is compliant in terms of lifestyle and adherence to treatment. Also, the doctor/clinician may wish to make sure that the patient has enough experience with the treatment and the dialysis instrument 104 to be able to accurately gauge when the patient needs a high, versus a low, versus a standard UF treatment. Even though the patient is making the prescription decisions in this embodiment, the data for trending as shown above is being sent to the dialysis center 120 and/or doctor 110, so that if the patient is making poor decisions as to which prescriptions to run, the dialysis center 120 and/or doctor 110 can detect the situation in short order and correct it. For example, system 10 enables the dialysis center 120 and/or doctor 110 to remove prescriptions from possible selection or to set the dialysis instrument 104 such that it automatically selects a prescription set at either machine 104 or a server computer 114 or 118.

It is believed, given the importance of a dialysis treatment, that most people will be responsible and that a conscientious and thoughtful patient will best be able to gauge when the patient may need a more aggressive or less aggressive prescription, knowing that even the less aggressive prescriptions have been approved and will remove a certain amount of UF. It is contemplated to provide more than three prescriptions. For example, the patient can have two high UF prescriptions, one that requires a longer night therapy and the other that requires a higher dextrose level. Assuming the patient knows that he/she needs to run a high UF prescription after a relatively large liquid intake day, the patient may choose the longer night therapy high UF prescription knowing that he/she has gained weight of late and is better off staying away from the higher caloric intake of the higher dextrose prescription. System 10 attempts to accommodate the patient's lifestyle, while ensuring that a proper therapy is performed, while also gathering therapy data over time to establish a thorough patient history that enables physiologic changes of the patient to be detected relatively quickly and accurately.

In another embodiment, dialysis instrument 104 selects which prescription the patient is to run based on the patient's daily body weight and possibly the patient's blood pressure. The patient weighs himself/herself, a weight signal is transmitted, e.g., wirelessly to dialysis instrument 104, which uses the weight signal to determine how much UF the patient has accumulated and accordingly which prescription to run. In one embodiment, the patient weighs himself/herself just prior to the last nighttime fill or just prior to a mid-day fill to establish a localized "dry weight". The patient then weighs himself/herself at night, just after the last fill drain, to establish a localized "wet weight". The difference between the localized "wet weight" and the localized "dry weight" determines a UF amount. The UF amount is fitted into one of a low UF range, standard UF range and high UF range. Dialysis instrument 104 then picks a corresponding low UF prescription, standard UF prescription or a high UF prescription to run. Alternatively, dialysis instrument 104 provides alternative prescriptions for a particular range, e.g., two high UF prescriptions, allowing the patient to pick one of the two high UF prescriptions. As discussed above, dialysis instrument 104 is configured in one embodiment to read bag identifiers to ensure that the patient connects the proper dialysate(s) and proper amount(s) of dialysate(s).

In a further alternative embodiment, the doctor 110 or dialysis center 120 chooses or pre-approves the prescriptions to be run on a given day, such that the patient does not have the ability to run a different prescription. Here, fill, dwell, and/or drain times can be preset, and the dialysis instrument 104 can also be configured to read bag identifiers to ensure that the patient connects the proper dialysate(s) and proper amount(s) of dialysate(s).

It is further contemplated to allow the patient to have input into which prescriptions are run, but wherein the doctor 110 or dialysis center 120 ultimately approves of a prescription selection or selection plan before the prescriptions are downloaded into dialysis instrument 104. For example, it is contemplated that the dialysis center 120 send an auto-generated email to the patient 102, e.g., each month one week prior to the start of the next month. The email includes a calendar, each day of the calendar shows all available prescriptions, e.g., (i) lowUF, (ii) midUFlowDEX, (iii) midUFhighDEX, (iv) highUFlowDEX and (v) highUFhighDEX. The patient clicks on one of the prescriptions for each day and sends the completed calendar to clinician 120 for approval. For example, the patient may choose to run one of the high UF prescriptions on the weekends and one of the middle or standard prescriptions during the week. Perhaps the patient attends physically demanding workout classes after work on Mondays and Wednesdays and selects the low UF prescription for those days.

It is contemplated to allow the patient to type notes in the days to explain why a particular prescription has been proposed. For example, the patient could select the lowUF prescription and type "spin class" in that calendar day. Or the patient could select the highUFhighDEX prescription and type "birthday party, up early next day" in that calendar day.

When the clinician receives the completed, proposed calendar from the patient, the clinician can either approve of the proposed calendar, call or email the patient with questions as to why one or more prescription was chosen for a particular day, forward the calendar to the doctor's office 110 if the clinician is concerned or has questions regarding the proposed calendar, or modify the selections in the calendar and send the modified calendar back to the patient. The clinician can review the patient's trend data when evaluating the proposed prescription calendar. For example, if the patient has been gaining weight and has selected the high dextrose standard UF for many or all of the days of the month, the clinician can call or email the patient and suggest switching to the low dextrose standard UF prescription in an attempt to control the patient's weight gain.

Eventually, the clinician and the patient reach a consensus. The doctor may or may not need to be consulted. It is expected that the patient's calendars will look similar from month to month and may change naturally based on season, vacations, and holidays. When a more radical change is presented, e.g., the patient intends to start a vigorous workout or training routine and wants to introduce more low UF days, the clinician can seek doctor approval.

In one embodiment, dialysis instrument 104 confirms that the patient wants to run a non-standard treatment on a particular day. The dialysis instrument 104 also enables the patient to switch to a standard therapy if the patient desires. For example, if the patient has Mondays and Wednesdays approved for a low UF prescription because the patient expects to have vigorous workouts those days, but the patient skips a workout, the patient can choose to run a standard UF prescription instead. Or, if the patient is slated to run a high UF prescription because he/she is supposed to attend a party on a given day, but misses the party, the patient can choose to run a standard UF prescription instead.

Dialysis instrument 104 could also be configured to provide the patient with a limited amount of prescription changes from a standard UF prescription to a low or high UF prescription. For example, if the patient decides to workout Thursday instead of Wednesday, the patient could switch the prescription from standard UF to low UF on Thursday. System 10 could be configured to allow for one such standard to non-standard prescription change per week, for example.

In another example, dialysis instrument 104 allows the patient to increase the UF removal at any time, that is, switch from low UF prescription to a standard or high UF prescription, or switch from a standard UF prescription to a high UF prescription at any time. If the patient chooses this option a certain number of times during the month, dialysis instrument 104 can be configured to send an alert to the doctor 110 or clinician 120.

The approved calendar in one embodiment is integrated with the inventory tracking feature 18. The approved calendar tells the inventory tracking feature 18 what is needed for the next delivery cycle, which can be a month to month cycle. If the patient can plan and gain approval for multiple months, the delivery cycle can be for the multiple months. In any case, the patient can be delivered extra solution if needed to allow for switches from the planned prescriptions.

In a further alternative embodiment, the patient and clinician and/or doctor agree that for each week the patient will run a certain number of standard, low and high prescriptions, e.g., five standard, one low and one high. The patient then chooses which days during the week to run the various prescriptions. The weekly allotment does not have to include any low UF or high UF allotments. The patient could have seven standard UF allotments with four low dextrose standard and three high dextrose standard prescriptions, for example. Here too, dialysis instrument 104 can be configured to let the patient change prescriptions in certain instances as described above.

In still a further alternative embodiment, dialysis instrument 104 or one of the server computers 114 or 118 picks one of the approved prescriptions for the patient for each therapy. The pick can be based on any of the trending data above and/or based on a series of questions answered by the patient such as: (i) Was your fluid intake today low, moderate, average, high or very high? (ii) Was your food intake today low, moderate, average, high or very high? (iii) Was your carbohydrate intake today low, moderate, average, high or very high? (iv) Was your sugar intake today low, moderate, average, high or very high? (v) Was your activity level today low, moderate, average, high or very high? System 10 then picks one of the approved prescriptions for the patient. Inventory management for this embodiment can be based on average usages over the past X number of delivery cycles. In any of the above regimes, dialysis instrument 104 can also read bag identifiers to ensure that the patient connects the proper dialysate(s) and proper amount(s) of dialysate(s).

As seen in FIG. 28, the selected daily prescriptions are fed into a switch mechanism for prescription recall and modification feature 26. The switch mechanism is activated when the applied alert generation algorithm of feature 24 computes an error that is greater than the threshold(s) of the applied alert generation algorithm. As seen in FIG. 28, when the applied alert generation algorithm of feature 24 computes an error that is not greater than the threshold, feature 26 maintains the current set of prescriptions and whichever prescription recall regime is being employed. Accordingly, the switch mechanism does not switch to a new prescription or set of prescriptions.

When a prescription is used for a treatment, the prescription carries with it a predicted UF, which is generated via regimen generation feature 14 and selected via prescription filtering feature 16.

Actual UF data is obtained from the short term and long term moving averages as discussed above in connection with trending and alert generation feature 24, which are in turn developed from measured UF data generated at dialysis instrument 104. Actual UF values area function of the patient's transport characteristics as has been described herein but also account for environmental factors, such as regimen deviation by the patient. Actual UF values are subtracted from the predicted UF values at difference generator 66a and fed into the alert generation algorithm at diamond 24. The actual UF values are also fed into a difference generator 66b, which are used to adjust target UF values used to generate the regimens in connection with feature 14. Other target values include target urea removal, target creatinine removal and target glucose absorption as discussed above.

As seen at diamond 24, once system 10 determines an alarm condition, system 10 triggers prescription adjustment switch mechanism. That does not necessarily mean that the patient's prescriptions will be adjusted. The doctor 110 ultimately makes the call based on the data of UF, patient daily weight, daily blood pressure, or estimated dry weight using a bio-impedance sensor. When it appears prescription adjustment is needed, system 10 via communications module 20 communicates with the patient, e.g., via wireless communication between APD system to modem through a router. Based on the received data, the nephrologist 110 at switch mechanism 26 could make following decisions: (i) continue with current prescriptions and come to office visit as previously planned; (ii) continue with current prescriptions but visit office sooner for possible prescription adjustment; (iii) switch to a different routine using current prescriptions, visit office soon, e.g., within two weeks, receive trending data on new routine; (iv) warn the patient that he/she is not being compliant with treatment and maintain current prescription(s); (v) warn the patient that he/she is running a low UF prescription(s) too often and maintain current prescription(s); (vi) continue with the current therapy and monitoring, but lower the UF target to A and lower the UF limit to B; and (vii) perform a new APD PET to evaluate the change of PD membrane transport characteristics and provide the center with updated therapy suggestions based upon this PET.

If the patient is fully compliant and the low UF is as a result of transport characteristic changes as verified by the new PET, doctor 110 can order a new one or prescription be generated, including a change in one or more standard UF prescription. To do so, regimen generation module 14 and prescription filtering module 16 are used again to develop the new prescription(s). The doctor agrees to the new prescriptions and switch mechanism 26 changes to the new prescription(s) as seen in FIG. 28.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
   a first home dialysis machine located at a first patient's home;
   a second home dialysis machine located at a second patient's home;
   a first modem in data communication with the first home dialysis machine;
   a second modem in data communication with the second home dialysis machine;
   a clinician server associated with a dialysis center, the dialysis center located remotely from the first and second home dialysis machines;
   a first clinician computer in data communication with the clinician server;
   a second clinician computer in data communication with the clinician server, the first and second clinician computers each configured to participate in the optimization and selection of at least one machine operating prescription;
   a dialysis center modem in data communication with the clinician server; and
   a network in data communication with the first modem, the second modem and the dialysis center modem, such that the machine operating prescription for a patient by either clinician computer can be delivered over the network to and operated on the first or second home dialysis machine, whichever is associated with the patient.

2. The dialysis system of claim 1, wherein the network is an internet, wide area network, or local area network.

3. The dialysis system of claim 1, wherein at least one of the first or second clinician computers is located within the dialysis center.

4. The dialysis system of claim 1, wherein at least one of the first home dialysis machine, the second home dialysis machine, or the clinician server is in wireless communication with the respective first modem, second modem or third modem.

5. The dialysis system of claim 1, wherein at least one of the first home dialysis machine, the second home dialysis machine, or the clinician server is in wired communication with the respective first modem, second modem or third modem.

6. The dialysis system of claim 1, wherein at least one of the first or second home dialysis machines is a home peritoneal dialysis machine.

7. The dialysis system of claim 1, which includes a doctor's computer in data communication with a doctor's office modem, and wherein the network is in further data communication with the doctor's office modem.

8. The dialysis system of claim 7, which includes two-way communication between the home dialysis machines, the clinician computers and the doctor's computer.

9. The dialysis system of claim 1, which includes inventory tracking software stored at the dialysis center.

10. The dialysis system of claim 1, which includes a service center connected to the network that tracks problems associated with the first and second home dialysis machines and/or provides new equipment for the first and second home dialysis machines.

11. The dialysis system of claim 1, wherein at least one of the first or second home dialysis machines is in data communication with at least one of a blood pressure monitor or a weight scale.

12. The dialysis system of claim 1, which is configured to require the machine operating prescription to be accepted by the patient.

13. A dialysis system comprising:
    a first home dialysis machine located at a first patient's home;
    a second home dialysis machine located at a second patient's home;
    a first network connection apparatus in data communication with the first home dialysis machine;
    a second network connection apparatus in data communication with the second home dialysis machine;
    a clinician server located remotely from the first and second home dialysis machines;
    a first clinician computer in data communication with the clinician server;
    a second clinician computer in data communication with the clinician server, the first and second clinician computers each configured to participate in the optimization and selection of at least one machine operating prescription;
    a dialysis center network connection apparatus in data communication with the clinician server; and
    a network in data communication with the first network connection apparatus, the second network connection apparatus and the dialysis center network connection apparatus, such that the machine operating prescription for a patient by either clinician computer can be delivered over the network to and operated on the first or second home dialysis machine, whichever is associated with the patient.

14. The dialysis system of claim 13, wherein at least one of the first dialysis center network connection apparatus, the second dialysis center network connection apparatus, or the dialysis center network connection apparatuses includes a modem.

15. The dialysis system of claim 13, which is configured to require the machine operating prescription to be accepted by the patient.

16. A dialysis system comprising:
    a first home dialysis machine located at a first patient's home;
    a second home dialysis machine located at a second patient's home;
    a first clinician server associated with a first dialysis center, the first clinician server located remotely from the first and second home dialysis machines;
    a first clinician computer in data communication with the first clinician server;
    a second clinician computer in data communication with the first clinician server, the first and second clinician computers communicating with the first clinician server each configured to participate in the optimization and selection of at least one machine operating prescription;
    a second clinician server associated with a second dialysis center, the second dialysis center located remotely from the first and second home dialysis machines;
    a first clinician computer in data communication with the second clinician server;
    a second clinician computer in data communication with the second clinician server, the first and second clinician computers communicating with the second clinician computer each configured to participate in the optimization and selection of at least one machine operating prescription; and a network in data communication with the first home dialysis machine, the second home dialysis machine, the first clinician server and the second clinician server, such that any of the machine operating prescriptions for a patient by any of the clinician computers can be delivered over the network to and operated on the first or second home dialysis machine, whichever is associated with the patient.

17. The dialysis system of claim 16, wherein at least one of the first clinician server, the first clinician computer in data communication with the first clinician server, or second clinician computer in data communication with the first clinician server is located at the first dialysis center.

18. The dialysis system of claim 16, which includes a central server, the first and second home dialysis machines and the first and second clinician servers in data flow communication with the central server.

19. The dialysis system of claim 18, wherein the central server stores software useable by at least one of the first or second home dialysis machines, the first or second clinician computers in data communication with the first clinician server, or the first or second clinician computers in data communication with the second clinician server.

20. The dialysis system of claim 16, which is configured to require the machine operating prescription to be accepted by the patient.

21. A dialysis system comprising:
a first home dialysis machine located at a first patient's home;
a second home dialysis machine located at a second patient's home;
a first clinician computer associated with a first dialysis center;
a second clinician computer associated with a second dialysis center, the first and second clinician computers each configured to participate in the optimization and selection of at least one machine operating prescription; and
a central server in data communication with the first home dialysis machine, the second home dialysis machine, the first clinician computer and the second clinician computer, such that the machine operating prescription for a patient by the first or second clinician computers can be delivered via the central server to and operated on the first or second home dialysis machine, whichever is associated with the patient.

22. The dialysis system of claim 21, which includes a first clinician server associated with the first dialysis center, the first clinician server in data communication with the first clinician computer and the central server.

23. The dialysis system of claim 21, wherein the central server is located at one of the first or second dialysis centers.

24. The dialysis method of claim 21, wherein the central server is located separately from the first and second dialysis centers.

25. The dialysis method of claim 21, wherein the central server includes multiple servers linked together.

26. The dialysis system of claim 21, wherein the central server stores software accessible via at least one of the first home dialysis machine, the second home dialysis machine, the first clinician computer, or the second clinician computer.

27. The dialysis system of claim 21, which includes a network, and wherein the first home dialysis machine, the second home dialysis machine, the first clinician computer and the second clinician computer are in data communication via the network.

28. The dialysis system of claim 21, which is configured to require the machine operating prescription to be accepted by the patient.

* * * * *